United States Patent
Xu et al.

(10) Patent No.: US 8,481,752 B2
(45) Date of Patent: Jul. 9, 2013

(54) FLUORESCENT IMAGING WITH SUBSTITUTED CYANINE DYES

(75) Inventors: Xinshe Xu, Lincoln, NE (US); Daniel R. Draney, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 46 days.

(21) Appl. No.: 12/820,077

(22) Filed: Jun. 21, 2010

(65) Prior Publication Data

US 2010/0323389 A1  Dec. 23, 2010

Related U.S. Application Data

(63) Continuation of application No. PCT/US2010/031434, filed on Apr. 16, 2010.

(60) Provisional application No. 61/170,579, filed on Apr. 17, 2009, provisional application No. 61/184,750, filed on Jun. 5, 2009.

(51) Int. Cl.
*C12Q 1/04*  (2006.01)
*C07K 16/00*  (2006.01)
*C07D 209/56*  (2006.01)
*C07D 209/02*  (2006.01)

(52) U.S. Cl.
USPC ........ 548/427; 548/455; 530/409; 530/391.5; 435/34

(58) Field of Classification Search
None
See application file for complete search history.

(56) References Cited

U.S. PATENT DOCUMENTS

| | | | |
|---|---|---|---|
| 4,264,694 A | 4/1981 | Pu et al. | |
| 4,871,656 A | 10/1989 | Parton et al. | |
| 6,136,612 A | 10/2000 | Della Ciana et al. | |
| 6,180,085 B1 | 1/2001 | Achileful et al. | |
| 6,258,340 B1 | 7/2001 | Licha et al. | |
| 6,287,662 B1 | 9/2001 | Takagishi et al. | |
| 6,534,041 B1 | 3/2003 | Licha et al. | |
| 6,673,334 B1 | 1/2004 | Achilefu et al. | |
| 6,716,994 B1 | 4/2004 | Menchen et al. | |
| 6,747,159 B2 | 6/2004 | Caputo et al. | |
| 6,761,878 B2 | 7/2004 | Achilefu et al. | |
| 6,949,635 B1 | 9/2005 | Kumar et al. | |
| 7,172,907 B2 | 2/2007 | Chen et al. | |
| 2002/0022004 A1 | 2/2002 | Licha et al. | |
| 2005/0226815 A1 | 10/2005 | Kawakami et al. | |
| 2005/0281741 A1 | 12/2005 | Achilefu et al. | |
| 2006/0223076 A1 | 10/2006 | Diwu et al. | |
| 2007/0021621 A1 | 1/2007 | Reddington | |
| 2007/0090331 A1 | 4/2007 | Seo et al. | |
| 2007/0232805 A1 | 10/2007 | Leung et al. | |

FOREIGN PATENT DOCUMENTS

| | | |
|---|---|---|
| EP | 1221465 A1 * | 7/2002 |
| FR | 2921838 A1 * | 4/2009 |
| WO | WO 02/24815 A1 | 3/2002 |
| WO | WO 2007/028118 A2 | 3/2007 |
| WO | WO 2007/088129 A2 | 8/2007 |

OTHER PUBLICATIONS

Lee et al. JOC (2008), 73(2), 723-725.*
Lee et al., JOC (2006), 71(20), 7862-7865.*
Berezin et al. Biophysical Journal (2007) 93, 2892-2899.*
Berezin, M.Y. et al., "Ratiometric Analysis of Fluorescence Lifetime for Probing Binding Sites in Albumin with Near-Infrared Fluorescent Molecular Probes," *Photochemistry and Photobiology*, 2007, vol. 83, pp. 1371-1378.
International Search Report mailed on Nov. 11, 2010, for International Application No. PCT/US2010/031434 filed on Apr. 16, 2010, 4 pages.

* cited by examiner

*Primary Examiner* — Nyeemah A Grazier
(74) *Attorney, Agent, or Firm* — Kilpatrick Townsend & Stockton LLP

(57) ABSTRACT

Compounds and methods are disclosed that are useful for noninvasive imaging in the near-infrared spectral range. The cyanine compounds of Formula I are presented:

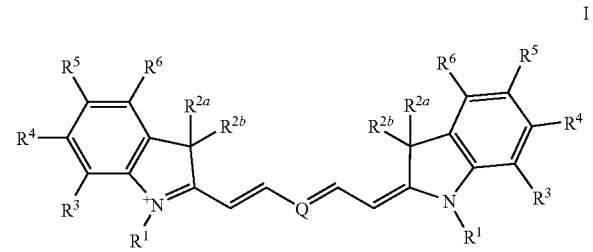

wherein Q is a portion of a polymethine bridge selected from the group consisting of:

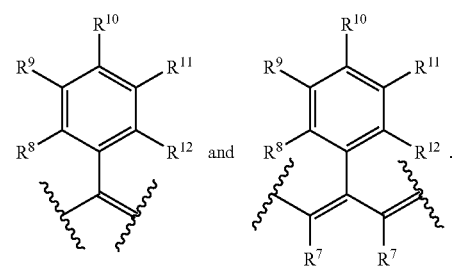

Also included are bioconjugates of the compounds of Formula I, methods of labeling biomolecules with the compounds, and methods of imaging.

29 Claims, 16 Drawing Sheets

FIG. 1A
FIG. 1B
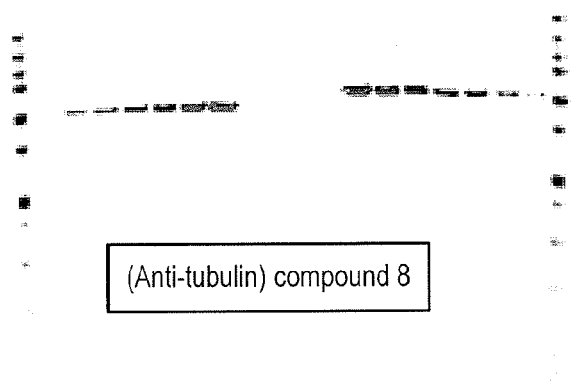
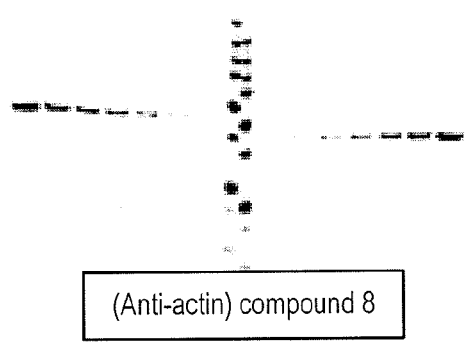
(Anti-tubulin) compound 8
(Anti-actin) compound 8
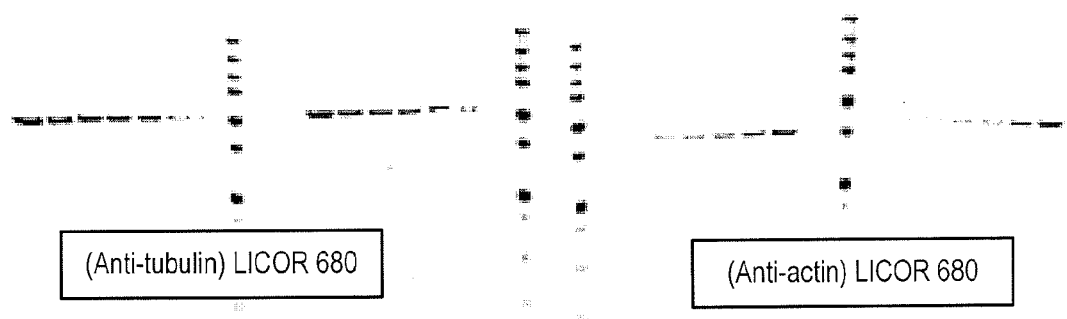
(Anti-tubulin) LICOR 680
(Anti-actin) LICOR 680
FIG. 1C
FIG. 1D

D/P 1.1 (diluted to 0.4 ug/ml)

D/P 1.3 (diluted to 0.4 ug/ml)

D/P 2.0 (diluted to 0.4 ug/ml)

LICOR Streptavidin 680
(diluted to 0.4 ug/ml)

Compound 8 in Methanol

Compound 8 in 1X PBS

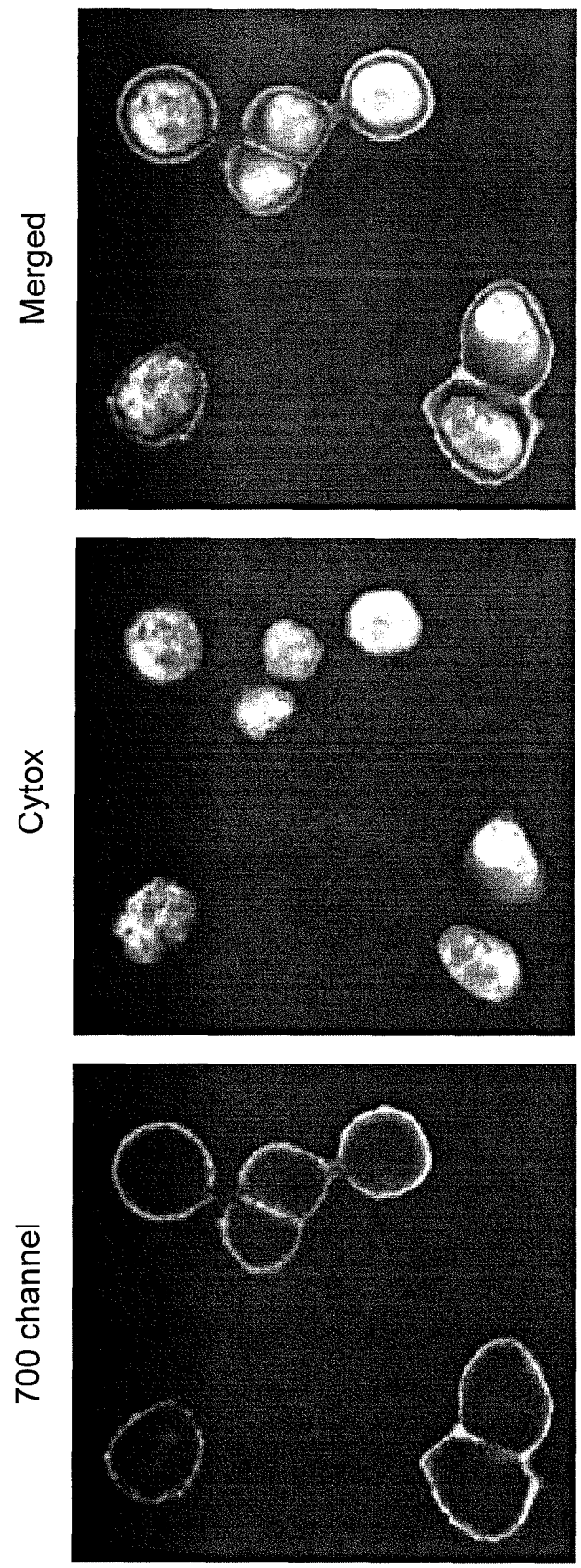

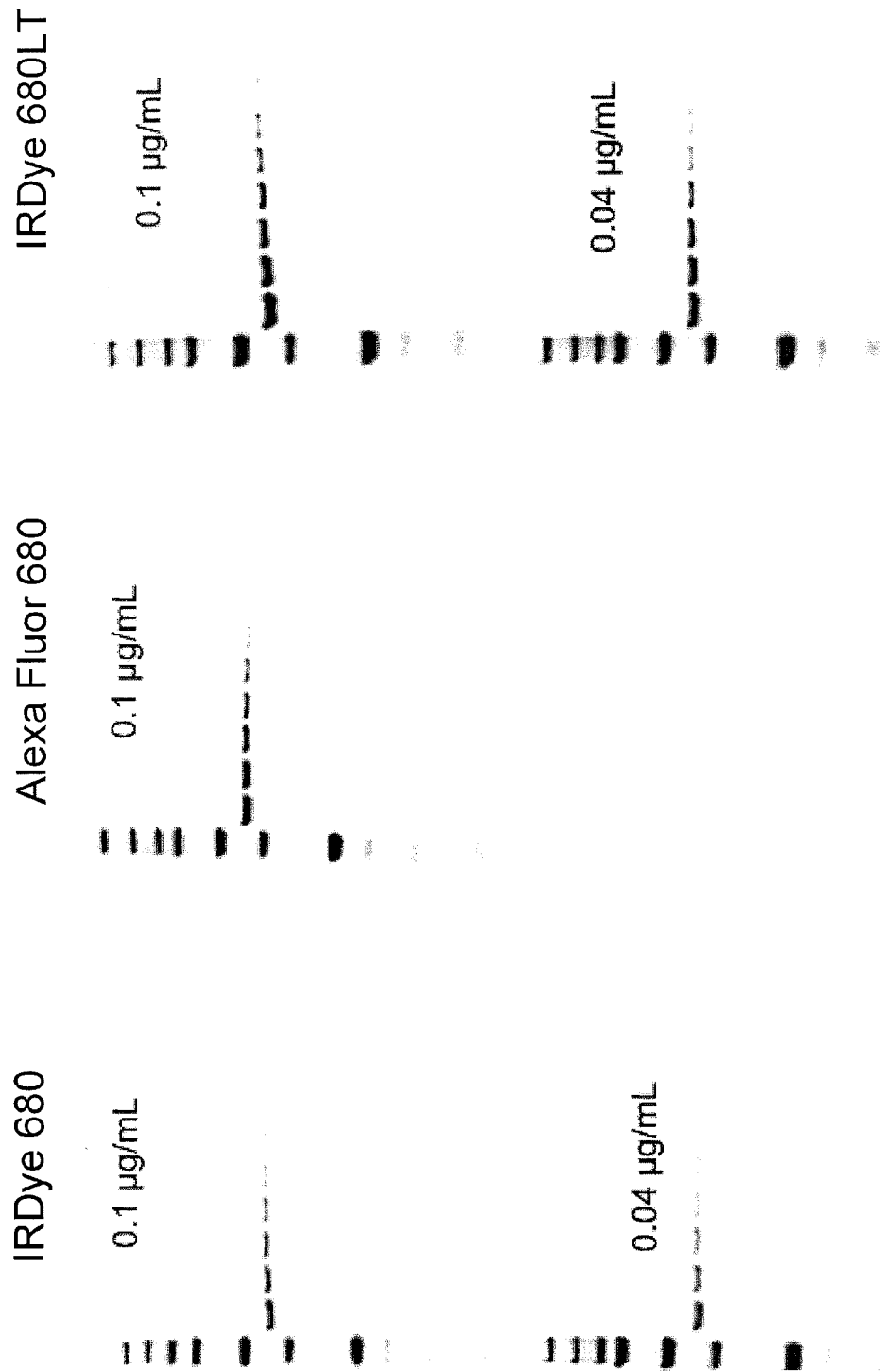

FLUORESCENT IMAGING WITH SUBSTITUTED CYANINE DYES

This application is a continuation application of Application No. PCT/US10/31434, filed on Apr. 16, 2010, which application claims priority to U.S. Provisional Patent Application No. 61/170,579, which was filed Apr. 17, 2009, and to U.S. Provisional Patent Application No. 61/184,750, which was filed Jun. 5, 2009. The disclosures of these applications are incorporated herein by reference for all purposes.

BACKGROUND OF THE INVENTION

Cyanine dyes have been widely used for labeling ligands or biomolecules for a variety of applications such as DNA sequencing. (See, for example, U.S. Pat. No. 5,571,388 for exemplary methods of identifying strands of DNA by means of cyanine dyes.) Scientists favor using cyanine dyes in biological applications because, among other reasons, many of these dyes fluoresce in the near-infrared (NIR) region of the spectrum (600-1000 nm). This makes cyanine dyes less susceptible to interference from autofluorescence of biomolecules.

Other advantages of cyanine dyes include, for example: 1) cyanine dyes strongly absorb and fluoresce light; 2) many cyanine dyes do not rapidly bleach under a fluorescence microscope; 3) cyanine dye derivatives can be made that are effective coupling reagents; 4) many structures and synthetic procedures are available, and the class of dyes is versatile; and 5) cyanine dyes are relatively small (a typical molecular weight is about 1,000 daltons), so they do not cause appreciable steric interference in a way that might reduce the ability of a labeled biomolecule to reach its binding site or carry out its function.

Despite their advantages, many of the known cyanine dyes have a number of disadvantages. Some known cyanine dyes are not stable in the presence of certain reagents that are commonly found in bioassays. Such reagents include ammonium hydroxide, dithiothreitol (DTT), primary and secondary amines, and ammonium persulfate (APS). Further, some known cyanine dyes lack the thermal stability and photostability that is necessary for biological applications such as DNA sequencing, Western blotting, in-cell Western immunofluorescence assays, in vitro or in vivo optical imaging, microscopy, and genotyping, while other dyes are not symmetric, making them more difficult to synthesize in high purity and yield. (See U.S. Pat. No. 6,747,159 for some advantages of symmetric dyes.)

For these reasons, stable and symmetric cyanine dyes are needed for use in labeling biomolecules as well as in vivo imaging for the diagnosis and prognosis of diseases such as cancer. Such compositions and methods would aid in the analysis of responses to various therapies. The present invention satisfies these and other needs.

BRIEF SUMMARY OF THE INVENTION

The present invention provides compounds, bioconjugates, methods of labeling, and methods of measuring or detecting target molecules non-invasively, thus solving the problems of the above-described art.

As such, in one embodiment, the present invention provides a compound of Formula I:

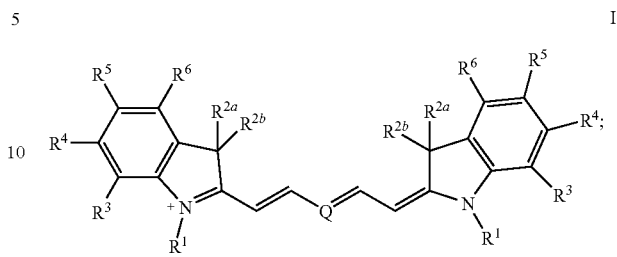

I wherein Q is a portion of a polymethine bridge selected from the group of:

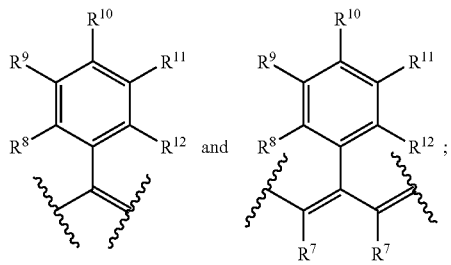

wherein Q is the central portion of either a five- or a seven-polymethine-carbon polymethine bridge;

$R^1$ is an alkyl group that is additionally substituted with from 0 to 1 $R^{13}$; wherein the alkyl is optionally interrupted by at least one heteroatom;

$R^{2a}$ and $R^{2b}$ are each a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; or, alternatively, $R^{2a}$ and $R^{2b}$, together with the ring carbon to which $R^{2a}$ and $R^{2b}$ are bonded, join to faun either a spirocycloalkyl ring, wherein the spirocycloalkyl ring is additionally substituted with from 0 to 6 $R^{14}$, or an exocyclic alkene, wherein the exocyclic alkene is additionally substituted with from 0 to 2 $R^{14}$;

$R^3$, $R^4$, $R^5$, and $R^6$ are each a member independently selected from the group of hydrogen, alkyl, alkenyl, halo, hydroxyl, alkoxy, cyano, carboxyl, alkoxycarbonyl, amido, sulfonato, alkoxyalkyl, carboxyalkyl, alkoxycarbonylalkyl, and sulfonatoalkyl; or, alternatively, a pair of members that is selected from the group of $R^3$ and $R^4$, $R^4$ and $R^5$, and $R^5$ and $R^6$, together with the pair of atoms to which the pair of members is bonded, joins to form an aryl ring, wherein each aryl ring is additionally substituted with from 0 to 2 $R^{14}$;

$R^7$ is a member selected from the group of hydrogen and alkyl; or, alternatively, both $R^7$, together with the intervening segment of the polyene to which both $R^7$ are bonded, join to form a ring, wherein the ring is selected from the group of a cycloalkyl and a heterocyclyl ring; and wherein the ring is additionally substituted with from 0 to 3 $R^{14}$, or an exocyclic alkene, wherein the alkene is additionally substituted with from 0 to 2 $R^{14}$;

$R^8$ and $R^9$ are each a member independently selected from the group of hydrogen, alkyl, alkenyl, halo, alkoxy, sulfonato, and -L-Y—Z; wherein exactly one member selected from the group of $R^8$ and $R^9$ is -L-Y—Z;

$R^{10}$, $R^{11}$, and $R^{12}$ are each a member independently selected from the group of hydrogen, alkyl, alkenyl, halo, alkoxy, and sulfonato;

each $R^{13}$ is a member independently selected from the group of hydroxyl, amino, cyano, carboxyl, alkoxycarbonyl, amido, sulfonato, and thioacetyl;

each $R^{14}$ is a member independently selected from the group of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the $R^{14}$ alkyl or alkenyl is additionally substituted with from 0 to 1 $R^{13}$;

L is an optional member selected from the group of a bond, a $C_1$-$C_{10}$ alkylene, and a $C_1$-$C_{10}$ alkenylene; wherein the alkylene or alkenylene is optionally interrupted by at least one heteroatom;

Y is an optional member selected from the group of a bond, —O—, —S—, —NH—, —NHC(O)—, —C(O)NH—, —NR$^{15}$—, —NR$^{15}$C(O)—, —C(O)NR$^{15}$—, —NZ—, —NZC(O)—, and —C(O)NZ—;

each Z is an independently selected $C_1$-$C_{10}$ alkyl that is additionally substituted with one member from the group of $R^{13}$ and $R^{16}$; wherein the alkyl is optionally interrupted by at least one heteroatom;

$R^{15}$ is a member selected from the group of alkyl and alkoxycarbonylalkyl; wherein the alkyl is optionally interrupted by at least one heteroatom;

each $R^{16}$ is independently a member selected from the group of activated acyl, azido, alkynyl, formyl, glycidyl, halo, haloalkyl, hydrazidyl, isothiocyanato, iodoacetamidyl, maleimidyl, mercapto, phosphoramidityl, and vinyl sulfonyl; and wherein the compound has a balanced charge.

In another embodiment, the present invention provides a bioconjugate of the Formula II:

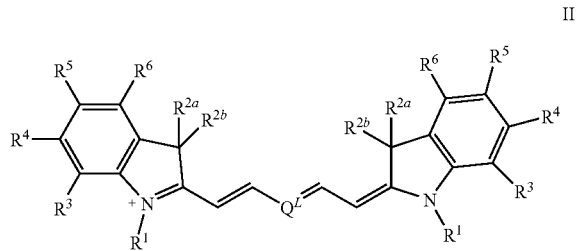

II wherein $Q^L$ is a portion of a polymethine bridge selected from the group of:

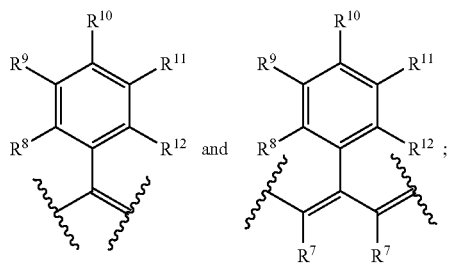

wherein $Q^L$ is the central portion of either a five- or a seven-polymethine-carbon polymethine bridge;

wherein $R^1$, $R^{2a}$, $R^{2b}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, L, and Y are as previously defined for the compound of Formula I;

each Z is an independently selected $C_1$-$C_{10}$ alkyl that is additionally substituted with one member from the group of $R^{13}$ and $R^L$; and wherein the alkyl is optionally interrupted by at least one heteroatom;

each $R^L$ comprises a linking group and the biomolecule connected thereby, wherein the compound comprises at least one $R^L$, and wherein the compound has a balanced charge.

In yet another embodiment, the present invention provides a method or process for labeling a ligand or biomolecule with a compound of Formula I, the method comprising contacting a ligand or biomolecule with a compound having Formula I to generate the corresponding bioconjugate compound of Formula II.

In still yet another embodiment, the compounds of Formula I or II can be used as in vitro or in vivo optical imaging agents of tissues and organs in various biomedical applications. In one aspect, the present invention provides a method for imaging, the method comprising administering a compound of Formula I or Formula II.

Further aspects, objects, and advantages of the invention will become apparent upon consideration of the detailed description and figures that follow.

BRIEF DESCRIPTION OF THE DRAWINGS

FIGS. 1A-D illustrate a Western blot total fluorescence comparison between a goat anti-mouse (GAM) antibody conjugate of inventive dye 8 (Panels A-B) and a commercially available GAM antibody conjugate of IRDye® 680 dye ("LI-COR 680") (Panels C-D).

FIGS. 11A-C illustrate the immunofluorescene staining of HER2 protein with GAR antibodies labeled with compound 8. Panel A ("700 Channel"): Cells were incubated with rabbit anti-HER2 mAb, followed by the GAR secondary antibody. Panel B: Sytox green was used to stain the nuclei. A merged image is illustrated in Panel C. Microscope setting for the Sytox green detection had an excitation filter centered at 488 nm with a spectral width of 20 nm. The dichroic was set at 495 nm, and the emission filter was centered at 525 with a spectral width of 50 rim. The detection setting for the "700 channel"

had an excitation filter centered at 620 nm with a spectral width of 60 nm. The dichroic was set at 660 nm, and the emission filter was centered at 700 with a spectral width of 75 nm.

FIGS. 12A-C illustrate a Western blot total fluorescence comparison of β-actin GAM antibody conjugates with compound 8 (Panel A); IRDye 680 (Panel B); and Alexa Fluor 680 (Panel C).

Figure 13:
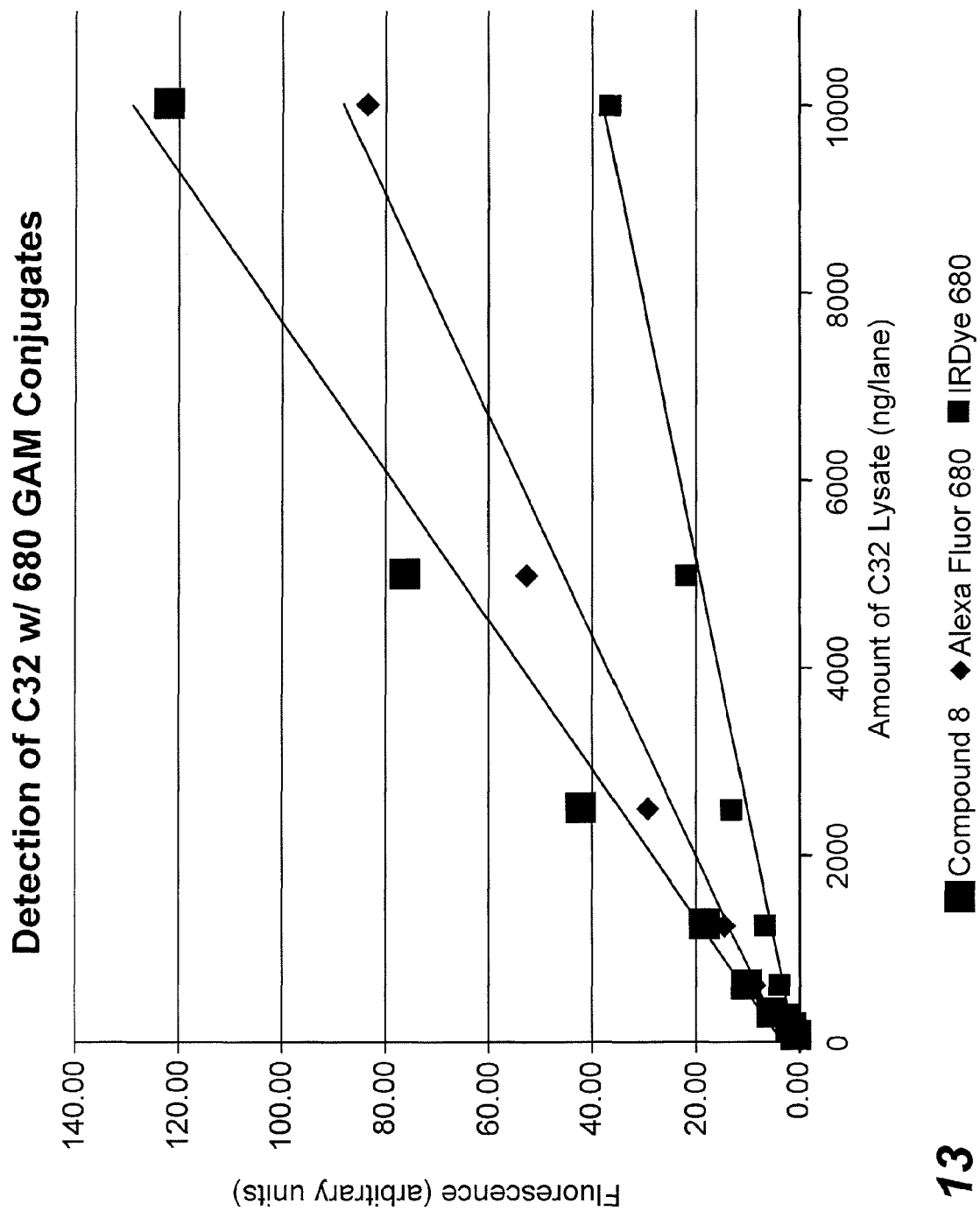

FIG. 13 illustrates the linearity of the β-actin GAM antibody conjugates' fluorescence intensity at increasing concentrations of cell lysate.

Figures 14A, 14B, 14C:
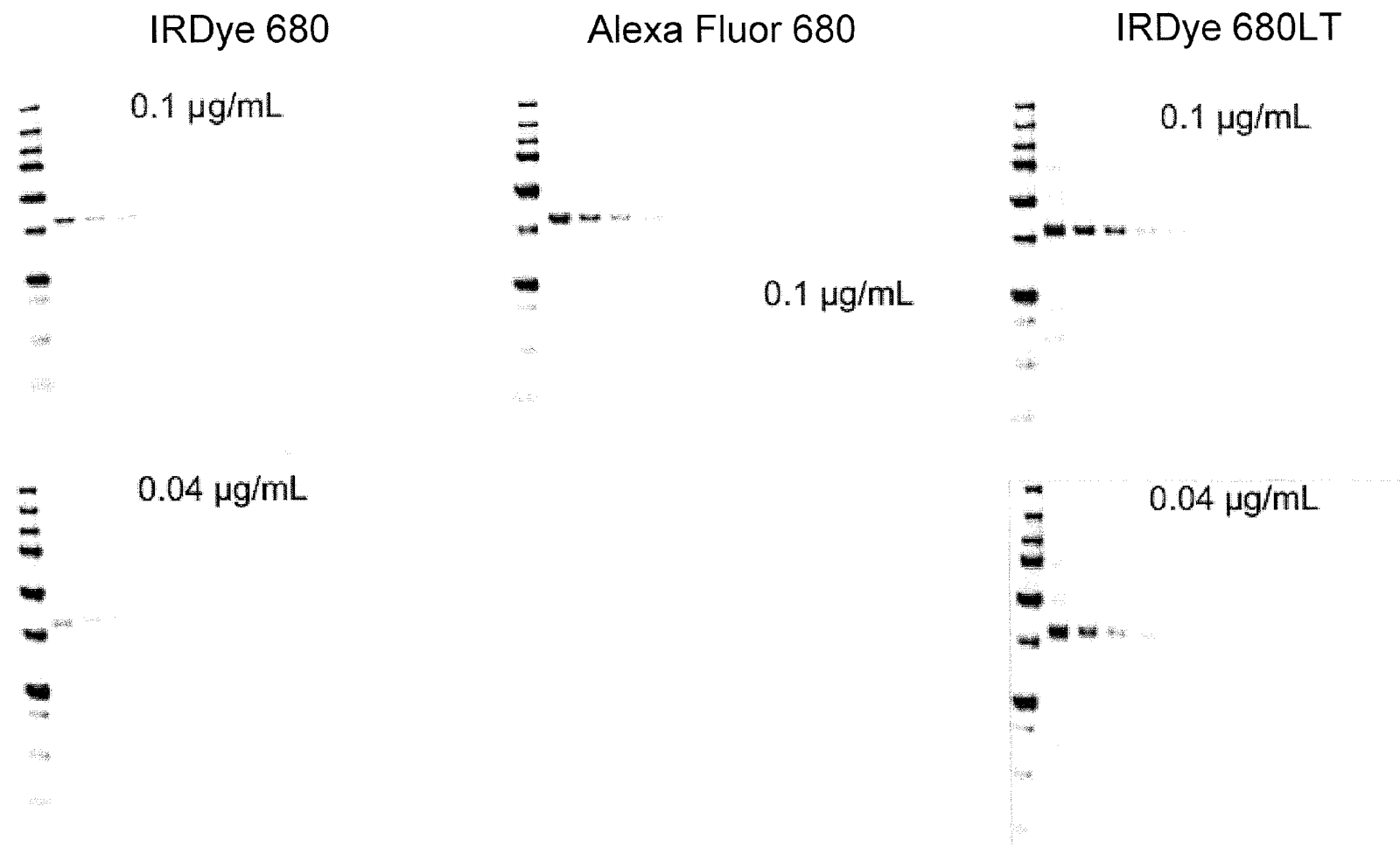

FIGS. 14A-C illustrate a Western blot total fluorescence comparison of p38 GAR antibody conjugates with compound 8, IRDye 680, and Alexa Fluor 680.

Figures 15A, 15B, 15C:
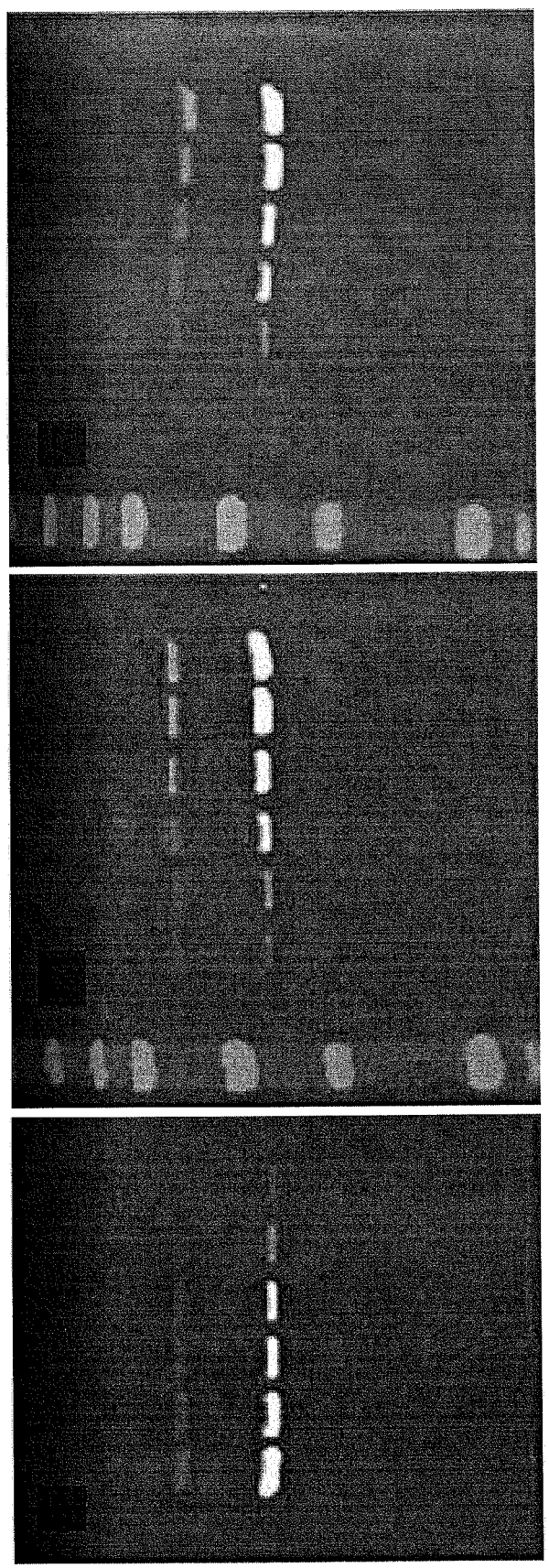

FIGS. 15A-C illustrate a two-color Western blot total fluorescence comparison of Akt GAM antibody conjugates with IRDye 680 (Panel A); compound 8 (Panel B); and Alexa Fluor 680 (Panel C). In each case, rabbit mAb for actin (bottom series) was detected with an IRDye 800CW GAR antibody conjugate.

Figure 16A:
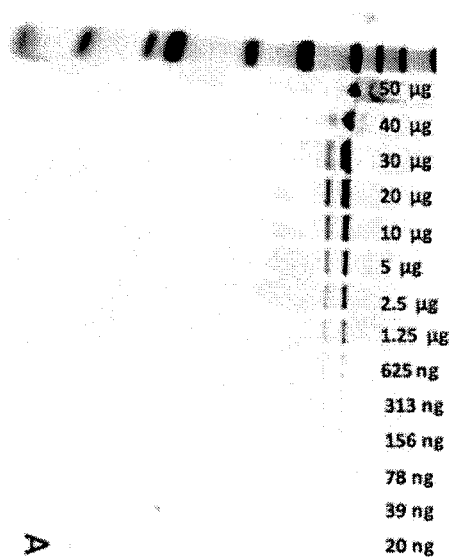
Figure 16B:
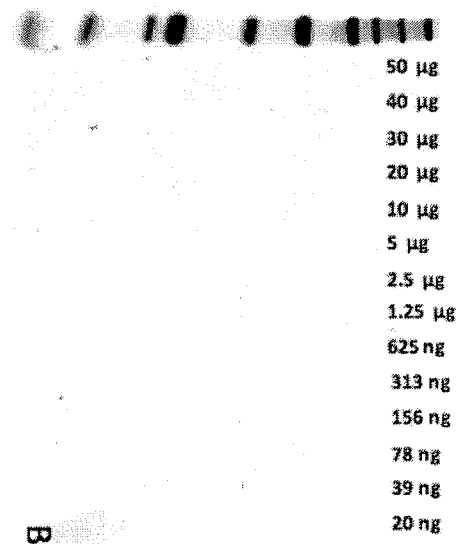

FIGS. 16A-B illustrate a Western blot total fluorescence comparison of Akt GAR antibody conjugates with compound 8, IRDye 680, and Alexa Fluor 680 (Panel A). A control experiment without primary antibody is illustrated in Panel B.

DETAILED DESCRIPTION OF THE INVENTION

I. Definitions

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. A activated acyl group may also be an activated ester as defined herein or a carboxylic acid activated by a carbodiimide to form an anhydride or mixed anhydride —OC(O)R$^a$ or —OC(NR$^a$)NHR$^b$, wherein R$^a$ and R$^b$ are members independently selected from the group consisting of $C_1$-$C_6$ alkyl, $C_1$-$C_6$perfluoroalkyl, $C_1$-$C_6$alkoxy, cyclohexyl, 3-dimethylaminopropyl, or N-morpholinoethyl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—$OC_4H_4NO_2$), sulfosuccinimidyloxy (—$OC_4H_3NO_2SO_3H$), -1-oxybenzotriazolyl (—$OC_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy). Preferred activated esters include succinimidyloxy and sulfosuccinimidyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double or triple bond. Preferred alkenyl groups have 2 to about 12 carbon atoms. More preferred alkenyl groups contain 2 to about 6 carbon atoms. In one aspect, hydrocarbon groups that contain a carbon-carbon double bond are preferred. In a second aspect, hydrocarbon groups that contain a carbon-carbon triple bond are preferred (i.e., alkynyl). "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, propynyl, 2-butynyl, 3-methylbutynyl, n-pentynyl, heptynyl, and the like.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH═CH—, —CH$_2$—CH═CH—, —C(CH$_3$)═CH—, —CH$_2$CH═CHCH$_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" as used herein includes an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene- group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 6 carbon atoms in the chain. "Branched-chain" as used herein includes that one or more lower alkyl groups such as methyl, ethyl or propyl are attached to a linear alkyl chain. "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthio-alkylene- group wherein alkylthio and alkylene are defined herein. Representative alkylthioalkyl groups include methylthiomethyl, ethylthiopropyl, isopropylthioethyl, and the like.

"Amido" as used herein includes a group of formula $Y_1Y_2N$—C(O)— wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2N$—C(O)—), methylamido, dimethylamido, diethylamido, and the like. Preferably, "amido" is an —C(O)NRR' group where R and R' are members independently selected from the group consisting of H and alkyl. More preferably, at least one of R and R' is H.

"Amidoalkyl" as used herein includes an amido-alkylene- group wherein amido and alkylene are defined herein. Representative amidoalkyl groups include amidomethyl, amidoethyl, dimethylamidomethyl, and the like.

"Amino" as used herein includes a group of formula $Y_1Y_2N$— wherein $Y_1$ and $Y_2$ are independently hydrogen, acyl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, and the like. Preferably, "amino" is an —NRR' group where R and R' are members independently selected from the group consisting of H and alkyl. Preferably, at least one of R and R' is H.

"Aminoalkyl" as used herein includes an amino-alkylene- group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Balanced charge" as used herein includes that the net charge for a compound and its associated counterions is zero under standard physiological conditions. In order to achieve a balanced charge, a skilled person will understand that after the first additional sulfonato group that balances the +1 charge of the indolinium ring of the compounds herein, a cationic counterion (e.g., the cation of a Group I metal such as sodium) must be added to balance the negative charge from additional sulfonato groups. Similarly, anionic counterions must be added to balance any additional cationic groups (e.g., most amino groups under physiological conditions).

"Biomolecule" as used herein includes a natural or synthetic molecule for use in biological systems. Preferred biomolecules include a protein, a peptide, an enzyme substrate, a hormone, an antibody, an antigen, a hapten, an avidin, a streptavidin, a carbohydrate, a carbohydrate derivative, an oligosaccharide, a polysaccharide, a nucleic acid, a deoxynucleic acid, a fragment of DNA, a fragment of RNA, nucleotide triphosphates, acyclo terminator triphosphates, PNA, and the like. More preferred biomolecules include a protein, a peptide, an antibody, an avidin, a streptavidin, and the like. Even more preferred biomolecules include an antibody, an avidin, and a streptavidin.

"Carboxy" and "carboxyl" as used herein include a HOC(O)— group (i.e., a carboxylic acid) or a salt thereof.

"Carboxyalkyl" as used herein includes a HOC(O)-alkylene- group wherein alkylene is defined herein. Representative carboxyalkyls include carboxymethyl (i.e., HOC(O)$CH_2$—) and carboxyethyl (i.e., HOC(O)$CH_2CH_2$—).

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one $sp^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Cyanine dye" as used herein includes a compound having two substituted or unsubstituted nitrogen-containing heterocyclic rings joined by an unsaturated bridge.

"Exocyclic alkene" or "exocyclic olefin" as used interchangeably herein includes an alkene having one alkene carbon that is part of a ring and the other alkene carbon not part of the same ring, though it may be included within a second ring. The second alkene carbon can be unsubstituted or substituted. If the second alkene carbon is disubstituted, the substituents can be the same (e.g., 1,1-dimethyl substitution) or different (e.g., 1-methyl-1-(2-ethoxyethyl) substitution). Examples of compounds with exocyclic alkenes include methylenecyclohexane; (E)-1-ethylidene-2,3-dihydro-1H-indene; pentan-3-ylidenecycloheptane; 2-cyclobutylidenepropan-1-ol; and (3-methoxycyclopent-2-enylidene) cyclohexane.

"Halo" or "halogen" as used herein includes fluoro, chloro, bromo, or iodo.

"Heptamethine" as used herein includes a polymethine containing seven polymethine carbons. In a preferred embodiment, the heptamethine is substituted at the 4-position.

"Heteroatom" as used herein includes an atom other than carbon or hydrogen. Representative heteroatoms include O, S, and N. The nitrogen or sulphur atom of the heteroatom is optionally oxidized to the corresponding N-oxide, S-oxide (sulfoxide), or S,S-dioxide(sulfone). In a preferred aspect, a heteroatom has at least two bonds to alkylene carbon atoms (e.g., —$C_1$-$C_9$ alkylene-O—$C_1$-$C_9$ alkylene-). In some embodiments, a heteroatom is further substituted with an acyl, alkyl, aryl, cycloalkyl, heterocyclyl, or heteroaryl group (e.g., —N(Me)—; —N(Ac)—).

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Heterocyclyl" as used herein includes a non-aromatic saturated monocyclic or multicyclic ring system of about 3 to about 10 ring atoms, preferably about 5 to about 10 ring atoms, in which one or more of the atoms in the ring system is an element or elements other than carbon, e.g., nitrogen, oxygen or sulfur. Preferred heterocyclyl groups contain about 5 to about 6 ring atoms. A heterocyclyl group optionally comprises at least one $sp^2$-hybridized atom (e.g., a ring incorporating an carbonyl, endocyclic olefin, or exocyclic olefin). The prefix "aza," "oxa," or "thia" before heterocyclyl means that at least a nitrogen, oxygen or sulfur atom respectively is present as a ring atom. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Heterocyclylene" as used herein includes a bivalent heterocyclyl group. Representative cycloalkylenyl groups include 1,2-, 1,3-, or 1,4-piperdinylene as well as 2,3- or 2,4-cis- or trans-piperidinylene.

"Heteroaryl" as used herein includes an aromatic monocyclic or multicyclic ring system of about 5 to about 14 ring atoms, preferably about 5 to about 10 ring atoms, in which at least one of the atoms in the ring system is an element other than carbon, i.e., nitrogen, oxygen or sulfur. Preferred heteroaryls contain about 5 to about 6 ring atoms. The prefix "aza," "oxa," or "thia" before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

"Linking group" as used herein includes the atoms joining a compound of Formula I with a biomolecule. Table 1 includes a list of preferred bonds for linking groups (i.e., Column C); the linking group comprises the resulting bond and optionally can include additional atoms. See also R. Haugland, Molecular Probes Handbook of Fluorescent Probes and Research Chemicals, Molecular Probes, Inc. (1992). In one embodiment, $R^{16}$ represents a linking group precursor before the attachment reaction with a biomolecule, and $R^L$ represents the resultant attachment between the compound of Formula I and the biomolecule (i.e., $R^L$ comprises the linking group and the biomolecule linked thereby). Preferred reactive functionalities include phosphoramidite groups, an activated ester (e.g., an NHS ester), thiocyanate, isothiocyanate, maleimide and iodoacetamide.

"Methine carbon" or "polymethine carbon" as used herein includes a carbon that is directly connecting the two heterocyclic rings by means of the polymethine bridge. In a preferred embodiment, at least one polymethine carbon of a polymethine bridge is additionally substituted with another group such as alkyl, cycloalkyl, or aryl (e.g., —CH═CH—C(Ar)═CH—CH═ or ═CH—CH═C(Ar)—(CH═CH)$_2$—).

"Oxo" as used herein includes a group of formula >C═O (i.e., a carbonyl group —C(O)—).

"Pentamethine" as used herein includes a polymethine containing five polymethine carbons. In a preferred embodiment, the pentamethine is substituted at the 3-position.

"Polyene" as used herein includes a straight or branched bivalent hydrocarbon chain containing at least two "alkenylene" groups as defined herein that are in conjugation. The polyene is optionally substituted with one or more "alkylene group substituents" as defined herein. A portion of the polyene may be incorporated into a ring (i.e., ═C(R)—, wherein R and the terminal bond are linked in a larger ring; or —C($R^1$)═C($R^2$)—, wherein $R^1$ and $R^2$ are linked in a larger ring). Representative polyenes include —CH═CH—CH═CH—, —CH═CH—C(Ar)═CH—CH═C(R)—, —C(R)═CH—CH═C(Ar)—(CH═CH)$_2$—, and the like.

"Polymethine" or "polymethine bridge" as used herein includes the series of conjugated, $sp^2$-hybridized carbons that form the unsaturated bridge directly connecting the two nitrogen-containing heterocyclic rings of a compound of Formula I. In a preferred embodiment, the polymethine has five or seven carbons directly connecting the heterocyclic rings (i.e., pentamethine or heptamethine).

"Phosphoramidityl" as used herein includes a trivalent phosphorous atom bonded to two alkoxy groups and an amino group.

"Spirocycloalkyl" as used herein includes a cycloalkyl in which geminal substituents on a carbon atom are replaced to form a 1,1-substituted ring.

"Sulfonato" as used herein includes an —SO$_3^-$ group, preferably balanced by a cation such as H$^+$, Na$^+$, K$^+$, and the like.

"Sulfonatoalkyl" as used herein includes an sulfonatoalkylene- group wherein sulfonato and alkylene are as defined herein. A more preferred embodiment includes alkylene groups having from 2 to 6 carbon atoms, and a most preferred embodiment includes alkylene groups having 2, 3, or 4 carbons. Representative sulfonatoalkyls include sulfonatomethyl, 3-sulfonatopropyl, 4-sulfonatobutyl, 5-sulfonatopentyl, 6-sulfonatohexyl, and the like.

II. Cyanine Dye Compounds

In one embodiment, the present invention provides a compound of Formula I:

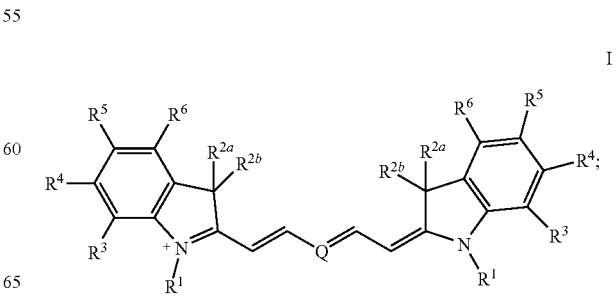

wherein Q is a member selected from the group of a one-methine-carbon segment and a three-methine-carbon segment:

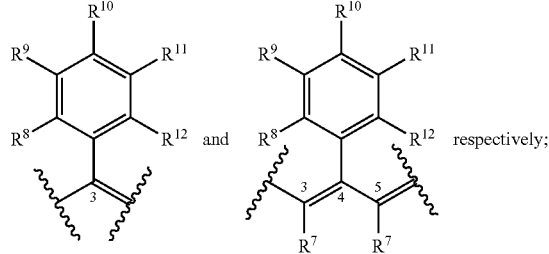

and respectively;

wherein the segment is the central portion of either a five- or a seven-methine-carbon polymethine bridge.

In a preferred aspect, Q is a portion of a polymethine bridge that is a pentamethine:

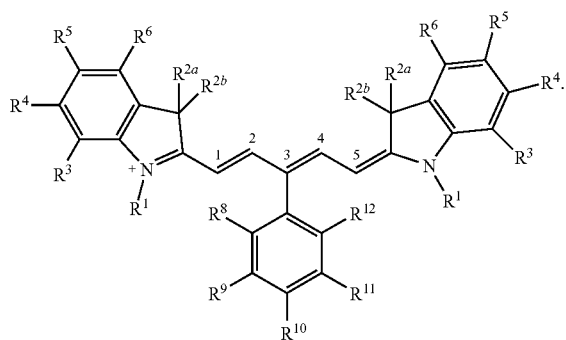

In a second preferred aspect, Q is a portion of a polymethine bridge that is a heptamethine:

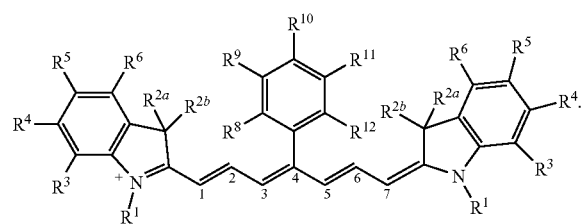

In an alternative preferred aspect, the polymethine bridge is a substituted heptamethine:

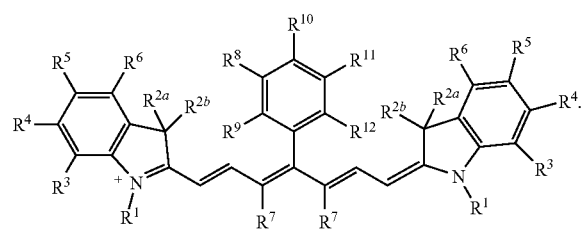

More preferably, the substituted heptamethine includes a cycloalkyl ring:

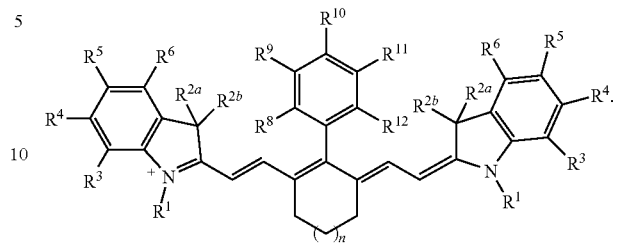

$R^1$ is an alkyl group that is additionally substituted with from 0 to 1 $R^{13}$; wherein the alkyl is optionally interrupted by at least one heteroatom. In a preferred aspect, $R^1$ is $C_2$-$C_{12}$ alkyl. In a more preferred aspect, $R^1$ is $C_2$-$C_8$ alkyl. In a still more preferred aspect, $R^1$ is $C_2$-$C_6$ alkyl. In a yet still more preferred aspect, $R^1$ is ethyl, propyl, butyl, or pentyl, and $R^1$ is additionally substituted with 1 $R^{13}$.

In a preferred aspect, $R^1$ is $(CH_2)_rSO_3H$ or $(CH_2)_rSO_3^-$; and r is an integer from 1 to 20. In a more preferred aspect, r is 2, 3, or 4.

In an alternative preferred aspect, $R^1$ is an alkyl group that is additionally substituted with 1 $R^{13}$ that is selected from the group of hydroxyl, amino, carboxy, and sulfonato. In a more preferred aspect, the $R^{13}$ substituent of $R^1$ is carboxy or sulfonato. In a still more preferred aspect, the $R^{13}$ substituent of $R^1$ is sulfonato. In a yet still more preferred aspect, $R^1$ is sulfonatoethyl, sulfonatopropyl, sulfonatobutyl, or sulfonatopentyl.

In another alternative preferred aspect, $R^1$ is an unbranched alkyl group that is additionally substituted with 1 $R^{13}$. In a more preferred aspect, $R^1$ is an unbranched alkyl group that is substituted with $R^{13}$ at the end of the alkyl group opposite to its attachment point to the cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl.

$R^{2a}$ and $R^{2b}$ are each a member independently selected from the group of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; or, alternatively, $R^{2a}$ and $R^{2b}$, together with the atom to which $R^{2a}$ and $R^{2b}$ are bonded, join to or a spirocycloalkyl ring, wherein the spirocycloalkyl ring is additionally substituted with from 0 to 6 $R^{14}$.

In a preferred aspect, $R^{2a}$ and $R^{2b}$ are the same. In a more preferred aspect, $R^{2a}$ and $R^{2b}$ are alkyl, alkenyl, aminoalkyl, carboxyalkyl, or sulfonatoalkyl. In a still more preferred aspect, $R^{2a}$ and $R^{2b}$ are alkyl, carboxyalkyl, or sulfonatoalkyl. In a yet still more preferred aspect, $R^{2a}$ and $R^{2b}$ are methyl.

In an alternative preferred aspect, $R^{2a}$ and $R^{2b}$ are different. In a more preferred aspect, $R^{2a}$ is alkyl, and $R^{2b}$ is selected from the group of alkyl, alkenyl, aminoalkyl, carboxyalkyl, or sulfonatoalkyl. In a still more preferred aspect, $R^{2a}$ is alkyl, and $R^{2b}$ is selected from the group of alkyl, carboxyalkyl, or sulfonatoalkyl.

In another alternative preferred aspect, $R^{2a}$ and $R^{2b}$, together with the ring carbon to which $R^{2a}$ and $R^{2b}$ are bonded, join to form a spirocycloalkyl ring, wherein the spirocycloalkyl ring is additionally substituted with from 0 to 6 $R^{14}$. In a more preferred aspect, $R^{2a}$ and $R^{2b}$ form a cyclopentyl or cyclohexyl ring. In an alternative more preferred aspect, $R^{2a}$ and $R^{2b}$ form a cyclopentyl or cyclohexyl ring additionally substituted with from 0 to 6 $R^{14}$. In a still more preferred aspect, $R^{14}$ is alkyl. In a yet still more preferred aspect, $R^{14}$ is methyl (e.g., 3,3- or 4,4-dimethyl substitution).

In yet another alternative preferred aspect, $R^{2a}$ and $R^{2b}$, together with the ring carbon to which $R^{2a}$ and $R^{2b}$ are bonded, join to form an exocyclic alkene, wherein the exocyclic alkene is additionally substituted with from 0 to 2 $R^{14}$. In a more preferred aspect, the exocyclic alkene is symmetrically substituted (e.g., unsubstituted; dialkyl; dicyano). Alternatively, the exocyclic alkene is substituted with two $R^{14}$ groups. Still more preferably, the exocyclic alkene's $R^{14}$ substituent is cyano.

$R^3$, $R^4$, $R^5$, and $R^6$ are each a member independently selected from the group of hydrogen, alkyl, alkenyl, halo, hydroxyl, alkoxy, cyano, carboxyl, alkoxycarbonyl, amido, amino, sulfonato, alkoxyalkyl, carboxyalkyl, alkoxycarbonylalkyl, and sulfonatoalkyl; or, alternatively, a pair of members that is selected from the group of $R^3$ and $R^4$, $R^4$ and $R^5$, and $R^5$ and $R^6$, together with the pair of atoms to which the pair of members is bonded, joins to form an aryl ring, wherein each aryl ring is additionally substituted with from 0 to 2 $R^{14}$.

In a first aspect, $R^3$, $R^4$, $R^5$, and $R^6$ are each a member independently selected from the group of hydrogen, alkyl, alkenyl, halo, alkoxy, cyano, carboxyl, alkoxycarbonyl, amido, amino, sulfonato, alkoxyalkyl, carboxyalkyl, alkoxycarbonylalkyl, and sulfonatoalkyl. In a preferred aspect, $R^3$, $R^4$, $R^5$, and $R^6$ are each a member independently selected from the group of hydrogen, alkyl, carboxy, carboxyalkyl, sulfanato, and sulfanatoalkyl. In a more preferred embodiment, $R^3$, $R^4$, $R^5$, and $R^6$ are each a member independently selected from the group of hydrogen and sulfanato.

In an alternative aspect, at least one member of the group $R^3$, $R^4$, $R^5$, and $R^6$ is hydrogen. Alternatively, exactly one member of the group $R^3$, $R^4$, $R^5$, and $R^6$ is hydrogen. In a preferred aspect, at least one pair of substituents selected from the pairs $R^3$ and $R^4$; $R^3$ and $R^5$; $R^3$ and $R^6$; $R^4$ and $R^5$; $R^4$ and $R^6$; $R^5$ and $R^6$ is hydrogen. Alternatively, exactly two members of the group $R^3$, $R^4$, $R^5$, and $R^6$ are hydrogen. In a more preferred aspect, exactly three members of the group $R^3$, $R^4$, $R^5$, and $R^6$ are hydrogen. In a still more preferred aspect, $R^3$, $R^4$, and $R^6$ are hydrogen.

In another alternative aspect, at least one member of the group $R^3$, $R^4$, $R^5$, and $R^6$ is sulfonato or sulfonatoalkyl. Alternatively, exactly one substituent selected from the group $R^3$, $R^4$, $R^5$, and $R^6$ is sulfonato or sulfonatoalkyl. In a preferred aspect, $R^5$ is sulfonato. In still another aspect, each member of a pair of substituents selected from the pairs $R^3$ and $R^4$; $R^3$ and $R^5$; $R^3$ and $R^6$; $R^4$ and $R^5$; $R^4$ and $R^6$; $R^5$ and $R^6$ is selected independently from the group of sulfonato or sulfonatoalkyl. Alternatively, exactly two members of the group $R^3$, $R^4$, $R^5$, and $R^6$ are each selected independently from sulfonato or sulfonatoalkyl. In still yet another aspect, exactly three members of the group $R^3$, $R^4$, $R^5$, and $R^6$ are each selected independently from sulfonato or sulfonatoalkyl.

In another alternative aspect, at least one member of the group $R^3$, $R^4$, $R^5$, and $R^6$ is anionic at physiological pH (e.g., sulfonato —$SO_3^-$, carboxy —$CO_2^-$). Alternatively, exactly one member of the group $R^3$, $R^4$, $R^5$, and $R^6$ is anionic at physiological pH. In a preferred aspect, $R^5$ is anionic at physiological pH. In still another aspect, each member of a pair of substituents selected from the pairs $R^3$ and $R^4$; $R^3$ and $R^5$; $R^3$ and $R^6$; $R^4$ and $R^5$; $R^4$ and $R^6$; $R^5$ and $R^6$ is anionic at physiological pH. Alternatively, exactly two members of the group $R^3$, $R^4$, $R^5$, and $R^6$ are anionic at physiological pH. In still yet another aspect, exactly three members of the group $R^3$, $R^4$, $R^5$, and $R^6$ are anionic at physiological pH.

In a second aspect, a pair of members that is selected from the group of $R^3$ and $R^4$, $R^4$ and $R^5$, and $R^5$ and $R^6$, together with the pair of atoms to which the pair of members is bonded, joins to form an aryl ring, wherein each aryl ring is additionally substituted with from 0 to 2 $R^{14}$. In a preferred aspect, $R^5$ and $R^6$, together with the pair of atoms to which the pair of members is bonded, joins to form a phenyl ring that is additionally substituted with from 0 to 2 $R^{14}$. In a more preferred aspect, the phenyl ring is additionally substituted with from 1 to 2 $R^{14}$. In a still more preferred aspect, the phenyl ring is additionally substituted with 2 $R^{14}$.

In a preferred aspect, the $R^{14}$ substituents of the aryl ring formed from $R^n$ and $R^{n+1}$ (e.g., the aryl ring formed from $R^5$ and $R^6$) are carboxy, carboxyalkyl, sulfonato, or sulfonatoalkyl. In a still more preferred aspect, the $R^{14}$ substituents are sulfonato or sulfonatoalkyl. In a yet still more preferred aspect, the benzindolinium $R^{14}$ substituents are sulfonato. In an alternative preferred aspect, the benzindolinium $R^{14}$ substituents are cyano.

In a more preferred aspect, the aryl ring formed from $R^n$ and $R^{n+1}$ is additionally substituted with from 1 to 2 $R^{14}$, and a $R^{14}$ substituent of the aryl ring is attached to a carbon adjacent to the ring junction with the indolinium ring. Alternatively, the aryl ring is additionally substituted with from 1 to 2 $R^{14}$, and a $R^{14}$ substituent of the aryl ring is attached to a carbon non-adjacent to the ring junction with the indolinium ring. Alternatively, the aryl ring is additionally substituted with one adjacent substituent and one non-adjacent substituent (e.g., the compound of Formula Ia).

Alternatively, in a preferred aspect, the compound has Formula Ia:

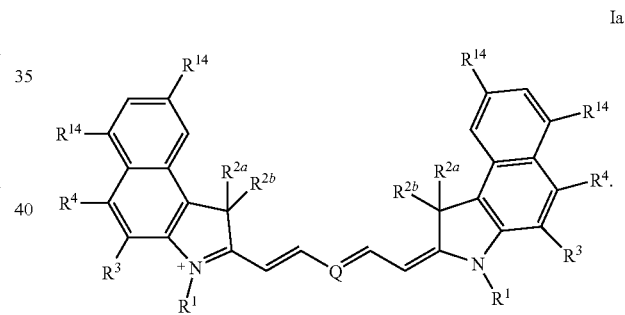

Ia

In a still more preferred aspect, the benzindolinium $R^{14}$ substituents of Formula Ia are carboxy, carboxyalkyl, sulfonato, or sulfonatoalkyl. In a still more preferred aspect, the benzindolinium $R^{14}$ substituents are sulfonato or sulfonatoalkyl. In a yet still more preferred aspect, the benzindolinium $R^{14}$ substituents are sulfonato.

$R^7$ is a member selected from the group of hydrogen and alkyl; or, alternatively, both $R^7$, together with the intervening segment of the polyene to which both $R^7$ are bonded, join to form a ring, wherein the ring is selected from the group of a cycloalkyl and a heterocyclyl ring, and wherein the ring is additionally substituted with from 0 to 3 $R^{14}$.

In one aspect, both $R^7$, together with the intervening segment of the polyene to which both $R^7$ are bonded, join to form a ring selected from the group of a five-membered ring and a six-membered ring, wherein the ring is additionally substituted with from 0 to 3 $R^{14}$. In a more preferred aspect, the ring is a six-membered ring (e.g., both $R^7$ combine to form a propylidene linking group). In a still more preferred aspect, the ring is cyclohexyl.

$R^8$ and $R^9$ are each a member independently selected from the group of hydrogen, alkyl, alkenyl, halo, alkoxy, sulfonato, and -L-Y—Z; wherein exactly one member selected from the group of $R^8$ and $R^9$ is -L-Y—Z.

In one aspect, $R^8$ is -L-Y—Z. Alternatively, $R^9$ is -L-Y—Z.

In a second aspect, $R^8$ is hydrogen, alkyl, alkoxy, or halo. In a more preferred aspect, $R^8$ is hydrogen. In another more preferred aspect, $R^8$ is fluoro.

Alternatively, $R^9$ is hydrogen, alkyl, alkoxy, or halo. In a more preferred aspect, $R^9$ is 5-carboxypentyl. Alternatively, $R^9$ is 4-carboxybutyl.

$R^{10}$, $R^{11}$, and $R^{12}$ are each a member independently selected from the group of hydrogen, alkyl, alkenyl, halo, alkoxy, and sulfonato.

In a first aspect, $R^{10}$ is hydrogen, alkyl, alkoxy, or halo. In a more preferred aspect, $R^{10}$ is hydrogen. Alternatively, $R^{10}$ is fluoro.

In a second aspect, $R^{11}$ is hydrogen, alkyl, alkoxy, or halo. In a more preferred aspect, $R^{11}$ is hydrogen. Alternatively, $R^{11}$ is fluoro. In a still more preferred aspect, $R^{10}$ and $R^{11}$ are hydrogen.

In a third aspect, $R^{12}$ is hydrogen, alkyl, alkoxy, or halo. In a more preferred aspect, $R^{12}$ is hydrogen. Alternatively, $R^{12}$ is fluoro. In a still more preferred aspect, $R^{10}$ and $R^{12}$ are hydrogen. Alternatively, $R^{11}$ and $R^{12}$ are hydrogen. In a yet still more preferred aspect, $R^{10}$, $R^{11}$, and $R^{12}$ are hydrogen.

In a fourth aspect, the phenyl ring substituted with $R^8$, $R^9$, $R^{10}$, $R^{11}$, and $R^{12}$ is 1,2,3-substituted with independently selected substituents other than hydrogen, and the 1-substituent is the polymethine bridge (e.g., $R^8$ is -L-Y—Z and $R^9$ is alkyl; $R^8$ is halo- and $R^9$ is -L-Y—Z). Alternatively, the ring is 1,2,4-substituted. Alternatively, the ring is 1,2,5-substituted. Alternatively, the ring is 1,2,6-substituted. Alternatively, the ring is 1,3,4-substituted. Alternatively, the ring is 1,3,5-substituted. Alternatively, the ring is 1,3,6-substituted.

In a fifth aspect, the phenyl ring substituted with $R^8$, $R^9$, $R^{10}$, $R^{11}$, and $R^{12}$ is 1,2,3,4-substituted with independently selected substituents other than hydrogen, and the 1-substituent is the polymethine bridge. Alternatively, the ring is 1,2,3,5-substituted. Alternatively, the ring is 1,2,3,6-substituted. Alternatively, the ring is 1,2,4,5-substituted. Alternatively, the ring is 1,2,4,6-substituted. Alternatively, the ring is 1,2,5,6-substituted. Alternatively, the ring is 1,3,4,5-substituted. Alternatively, the ring is 1,3,4,6-substituted. Alternatively, the ring is 1,3,5,6-substituted.

In a sixth aspect, the phenyl ring substituted with $R^8$, $R^9$, $R^{10}$, $R^{11}$, and $R^{12}$ is 1,2,3,4,5-substituted with independently selected substituents other than hydrogen, and the 1-substituent is the polymethine bridge. Alternatively, the ring is 1,3,4,5,6-substituted. Alternatively, the ring is 1,2,4,5,6-substituted. Alternatively, the ring is 1,2,3,5,6-substituted. Alternatively, the ring is 1,2,3,4,6-substituted. Alternatively, the ring is independently substituted at each ring position.

In a seventh aspect, $R^8$, $R^{10}$, $R^{11}$, and $R^{12}$ are each a member independently selected from the group of hydrogen, alkyl, halo, and sulfonato.

In an eighth aspect, the combination of the phenyl ring and its substituents $R^8$, $R^9$, $R^{10}$, $R^{11}$, and $R^{12}$ has at least ten carbons.

Each $R^{13}$ is a member independently selected from the group of hydroxyl, amino, carboxyl, alkoxycarbonyl, cyano, amido, sulfonato, and thioacetyl. In a preferred embodiment, $R^{13}$ is carboxyl, amido, or alkoxycarbonyl. In a more preferred embodiment, $R^{13}$ is carboxyl. Alternatively, $R^{13}$ is sulfonato. Alternatively, $R^{13}$ is cyano.

Each $R^{14}$ is a member independently selected from the group of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the $R^{14}$ alkyl or alkenyl is additionally substituted with from 0 to 1 $R^{13}$. In a preferred aspect, $R^{14}$ is alkyl, alkenyl, carboxyl, alkoxycarbonyl, amido, or alkoxycarbonylalkyl. Alternatively, $R^{14}$ is sulfonato. In a more preferred aspect, $R^{14}$ is alkyl or alkyl substituted with 1 $R^{13}$. Alternatively, $R^{14}$ is carboxyalkyl, hydroxyalkyl, or sulfonatoalkyl L is an optional member selected from the group of a bond, a $C_1$-$C_{10}$ alkylene, and a $C_1$-$C_{10}$ alkenylene; wherein the alkylene or alkenylene is optionally interrupted by at least one heteroatom. In a preferred aspect, L is not present. Alternatively, L is a $C_1$-$C_{10}$ alkylene interrupted by ether linkages (e.g., a polyethylene glycol oligomer).

Y is an optional member selected from the group of a bond, —O—, —S—, —NH—, —NHC(O)—, —C(O)NH—, —NR$^{15}$—, —NR$^{15}$C(O)—, —C(O)NR$^{15}$—, —NZ—, —NZC(O)—, and —C(O)NZ—. In a preferred aspect, Y is a bond. Alternatively, Y is —O—. Alternatively, Y is an amido group optionally substituted with $R^{15}$ at the amido nitrogen.

Each Z is an independently selected $C_1$-$C_{10}$ alkyl that is additionally substituted with one member from the group of $R^{13}$ and $R^{16}$; wherein the alkyl is optionally interrupted by at least one heteroatom. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In another alternative preferred aspect, -L-Y— is $(CH_2)_t$; Z is carboxyl or activated acyl; and t is an integer from 1 to 10.

In still another alternative preferred aspect, Z is optional, and $R^{13}$ or $R^{16}$ is connected directly to -L-Y— or directly bonded to the phenyl ring itself if L and Y are absent.

In yet still another alternative preferred aspect, -L-Y—Z has at least four carbons. Alternatively, Z has at least four carbons.

$R^{15}$ is a member selected from the group of alkyl and alkoxycarbonylalkyl; wherein the alkyl is optionally interrupted by at least one heteroatom. In a preferred aspect, $R^{15}$ is alkyl. In a more preferred aspect, $R^{15}$ is lower alkyl. Alternatively, $R^{15}$ is interrupted by ether linkages (e.g., a polyethylene glycol oligomer).

Each $R^{16}$ is independently a member selected from the group of activated acyl, formyl, glycidyl, halo, haloalkyl, hydrazidyl, isothiocyanato, iodoacetamidyl, maleimidyl, mercapto, phosphoramidityl, and vinyl sulfonyl. In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In a preferred aspect, Q is

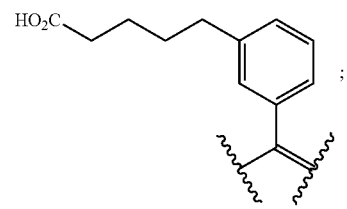 [SMILES: *C(=*)c1cccc(CCCCC(=O)O)c1]

and $R^3$, $R^4$, $R^5$, and $R^6$ are each a member independently selected from the group of hydrogen and sulfonato. The foregoing Q is for example, part of Formula Ia.

In a more preferred aspect, the compound has the formula:

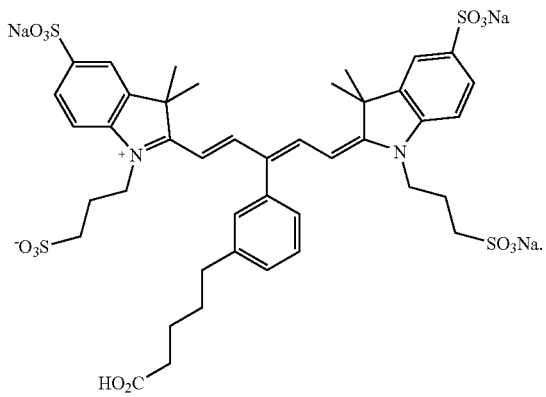

In a second more preferred aspect, the compound has the formula:

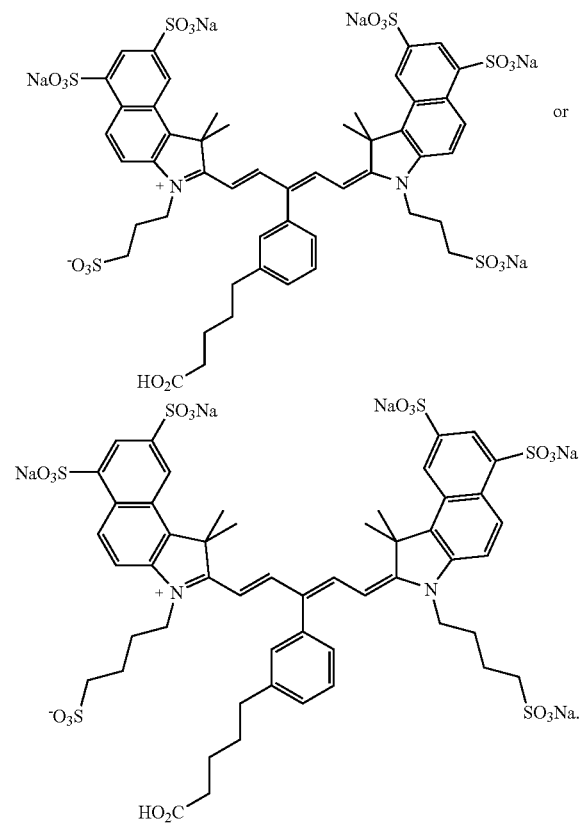

Alternatively, in certain aspects, an activated acyl group is present in place of the carboxy group. In a still more preferred aspect, the activated acyl group is an activated ester. In a still yet more preferred aspect, the activated ester is a succinimidyloxy-ester.

In a first aspect, the compound of Formula I fluoresces at a wavelength within the range of about 550 nm to about 1000 nm. Preferably, the compound fluoresces at a wavelength within the range of about 600 nm to about 850 nm. More preferably, the compound fluoresces at a wavelength within the range of about 600 nm to about 725 nm. Alternatively, the compound fluoresces at a wavelength within the range of about 725 nm to about 850 nm.

One preferred aspect of the instant invention are compounds with the same substituents on both heterocyclic rings (e.g., both $R^1$ are the same sulfonatoalkyl substituent, optionally with different counterions to balance charge). This provides advantages during the synthesis and purification of the compound.

The present application broadly encompasses all possible stereoisomers of the compounds as described herein, including the various diasteromers, enantiomers, and olefin stereoisomers apparent to one of skill in the art. This application is further directed to all methods of purifying cyanine dye compound stereoisomers that are well-known in the art as well as the purified compounds available by these methods.

III. Preparation of Compounds of Formula I

In one aspect, the preferred cyanine compounds of Formula I are prepared by reaction with a dialdehyde or dialdehyde equivalent (e.g., a Schiff base) that already incorporates the substituent for the polymethine bridge. A representative procedure for a dialdehyde is included in pending U.S. patent application Ser. No. 12/065,391 (US 2008/0267883 A1). A representative procedure for a Schiff base is included in U.S. Pat. No. 6,747,159 (Ar=Ph; pyridine/Ac$_2$O, Δ). The substituent can optionally be modified after the synthesis of the polymethine bridge (e.g., deprotected, activated for reaction with a biomolecule, or reacted to form a linking group).

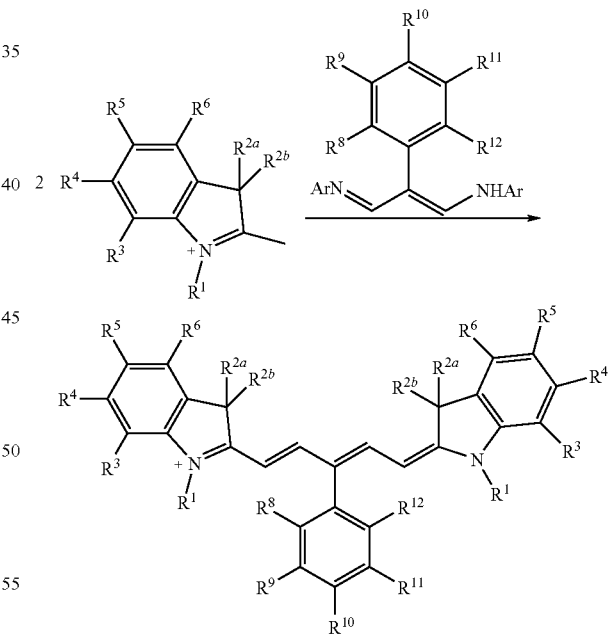

In another aspect, the preferred cyanine compounds of Formula I are prepared by means of an organometallic coupling to incorporate a substituent to the polymethine bridge. More preferably, the substituent is installed by means of a palladium coupling. The substituent can optionally be modified after its inclusion (e.g., deprotected, activated for reaction with a biomolecule, or reacted to form a linking group).

The Miyaura-Suzuki reaction, also known as the Suzuki coupling, has been extensively used in organic synthesis since its discovery: Miyaura, N.; Yamada, K.; Suzuki, A. *Tetrahedron Lett.* 1979, 36, 3437-3440. Recently a Suzuki coupling was used to install a substituted aryl substituent at the central position of a heptamethine bridge in a water-soluble cyanine dye: Lee, H.; Mason, J. C.; Achilefu, S. *J. Org. Chem.* 2006, 71, 7862-7865.

However, because many cyanine dyes decompose under standard Suzuki coupling conditions of heating with a base, few examples of its use for the synthesis of cyanine dyes are known.

In a particularly preferred aspect of the instant invention, the substituent of a compound of Formula I is incorporated by means of a Suzuki coupling reaction, some of which are detailed in the examples of this specification. In one embodiment, the polymethine substrate for the Suzuki coupling is a 3-halopentamethine or a 4-haloheptamethine. In a preferred embodiment, the halo-substituent is a chloride or a bromide. In a more preferred embodiment, the halo-substituent is a bromide.

Other means of preparing cyanine dyes and their synthetic precursors are included in Hamer, F. M., *Cyanine Dyes and Related Compounds*, Weissberger, Mass., ed. Wiley Interscience, N.Y. 1964; and Mojzych, M., Henary, M. "Synthesis of Cyanine Dyes," *Top. Heterocycl. Chem.*, vol. 14, Springer Berlin, Heildelberg, 2008, pp. 1-9. Further, U.S. Pat. Nos. 4,337,063; 4,404,289; and 4,405,711 describe a synthesis for a variety of cyanine dyes having N-hydroxysuccinimide active ester groups. U.S. Pat. No. 4,981,977 describes a synthesis for cyanine dyes having carboxylic acid groups. U.S. Pat. No. 5,268,486 discloses a method for making arylsulfonate cyanine dyes. U.S. Pat. No. 6,027,709 discloses methods for making cyanine dyes having phosphoramidite groups. U.S. Pat. No. 6,048,982 discloses methods for making cyanine dyes having a reactive group selected from the group of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

One common synthetic route involves preparing substituted or unsubstituted indolesulfonate quaternary salts according to procedures that are well-known in the art, some of which are detailed in the examples of this specification. Particularly preferred indole quaternary salts include, among others, indolesulfonate and benzindolesulfonate quaternary salts, which are exemplified in this specification.

The pair of synthesized salts are then reacted with a dialdehyde or a dialdehyde equivalent (e.g., a Schiff base) to form the polymethine bridge by means of techniques and reaction conditions that are well-known in the art, some of which are detailed in the examples of this specification. Representative Schiff bases include N-[(3-(anilinomethylene)-2-chloro-1-cyclohexen-1-yl)methylene]aniline monohydrochloride and N-(2-bromo-3-(phenylamino)allylidene)benzenaminium bromide. Schiff bases can be purchased from commercial suppliers (e.g., Sigma-Aldrich) or prepared according to procedures that are well-known in the art (e.g., the method of Example 5).

IV. Methods of Labeling Biomolecules

The cyanine compounds of Formula I can be attached to biomolecules, which are defined above. Methods of linking dyes to various types of biomolecules are well-known in the art. For a through review of, e.g., oligonucleotide labeling procedures, see R. Haugland in Excited States of Biopolymers, Steiner ed., Plenum Press (1983), Fluorogenic Probe Design and Synthesis: A Technical Guide, PE Applied Biosystems (1996), and G. T. Herman, Bioconjugate Techniques, Academic Press (1996).

"Click" chemistry provides one possible way for linking the inventive dyes to biomolecules. Click chemistry uses simple, robust reactions, such as the copper-catalyzed cycloaddition of azides and alkynes, to create intermolecular linkages. For a review of click chemistry, see Kolb, H. C.; Finn, M. G.; Sharpless, K. B. *Angew. Chem.* 2001, 40, 2004.

In one aspect, the cyanine compounds of Formula I have sufficient solubility in aqueous solutions that once they are conjugated to a soluble ligand or biomolecule, the ligand or biomolecule retains its solubility. In certain instances, the bioconjugates also have good solubility in organic media (e.g., DMSO or DMF), which provides considerable versatility in synthetic approaches to the labeling of desired materials.

In another aspect, the present invention provides a method or process for labeling a ligand or biomolecule with a compound of Formula I, the method comprising: contacting a ligand or biomolecule with a compound having Formula I or Ia to generate the corresponding bioconjugate compound of Formula II or IIa.

In one preferred embodiment, the $R^{16}$ group or the $R^{13}$ group reacts with a thiol, a hydroxyl, a carboxyl, or an amino group on a biomolecule, forming a linking group between the dye and the biomolecule. In a more preferred embodiment, this reaction is carried out in mixtures of aqueous buffer and an organic solvent such as DMF at pH 8 to 9. Alternatively, this reaction is carried out in distilled water or in an aqueous buffer solution. For thiols or for acidic groups, a pH of 7 or lower is preferred for the reaction solvent, especially if a substrate also contains a reactive amino group.

Selected examples of reactive functionalities useful for attaching a compound of Formula I to a ligand or biomolecule are shown in Table 1, wherein the bond results from the reaction of a dye with a ligand or biomolecule. Column A of Table 1 is a list of the reactive functionalities, which can be on the compound of Formula I or the biomolecule. Column B is a list of the complementary reactive groups (preferably, a carboxyl, hydroxyl, thiol, or amino functionality), which can be on the biomolecule or the compound of Formula I, and which react with the indicated functionality of Column A to form the bond of Column C. Those of skill in the art will know of other bonds suitable for use in the present invention.

TABLE 1

Exemplary Bonds for Linking Groups

| A<br>Reactive Functionality<br>(Compound of Formula I<br>or Biomolecule) | B<br>Complementary Group<br>(Biomolecule or<br>Compound of Formula I) | C<br>Resulting<br>Linking Group |
|---|---|---|
| activated esters* | amines/anilines | amides |
| acrylamides | thiols | thioethers |
| acyl azides** | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |

TABLE 1-continued

Exemplary Bonds for Linking Groups

| A<br>Reactive Functionality<br>(Compound of Formula I<br>or Biomolecule) | B<br>Complementary Group<br>(Biomolecule or<br>Compound of Formula I) | C<br>Resulting<br>Linking Group |
|---|---|---|
| anhydrides | amines/anilines | amides/imides |
| aryl halides | thiols | thiophenols |
| aryl halides | amines | aryl amines |
| azides | alkynes | 1,2,3-triazoles |
| aziridines | thiols | thioethers |
| boronates | glycols | boronate esters |
| activated carboxylic acids | amines/anilines | amides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

*Activated esters, as understood in the art, generally have the formula —C(O)OM, where —OM is a leaving group (e.g. succinimidyloxy (—OC$_4$H$_4$NO$_2$), sulfosuccinimidyloxy (—OC$_4$H$_3$NO$_2$SO$_3$H),-1-oxybenzotriazolyl (—OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or —C(O)OM is a carboxylic acid activated by a carbodiimide to form an anhydride or mixed anhydride —C(O)OC(O)R$^a$ or —C(O)OC (NR$^a$)NHR$^b$, wherein R$^a$ and R$^b$ are members independently selected from the group consisting of C$_1$-C$_6$ alkyl, C$_1$-C$_6$ perfluoroalkyl, C$_1$-C$_6$ alkoxy, cyclohexyl, 3-dimethylaminopropyl, or N-morpholinoethyl).
**Acyl azides can also rearrange to isocyanates.

When linking a compound of Formula I having a carboxylic acid with an amine-containing ligand or biomolecule, the carboxylic acid can first be converted to a more reactive form, e.g, a N-hydroxy succinimide (NHS) ester or a mixed anhydride, by means of an activating reagent. The amine-containing ligand or biomolecule is treated with the resulting activated acyl to form an amide linkage. In a more preferred embodiment, this reaction is carried out in aqueous buffer at pH 8 to 9 with DMSO or DMF as an optional co-solvent. Alternatively, this reaction is carried out in distilled water or in an aqueous buffer solution.

Similarly, the attachment of an isocyanate- or isothiocyanate-containing compound of Formula I is analogous to the procedure for the carboxy dye, but no activation step is required. The amine-containing ligand or biomolecule is treated directly with the activated acyl compound to form a urea or a thiourea linkage. In a more preferred embodiment, the reaction is carried out in aqueous buffer at pH 9 to 10 with DMSO or DMF as an optional co-solvent. Alternatively, this reaction is carried out in distilled water or in an aqueous buffer solution.

If the compound of Formula I or biomolecule has a reactive hydroxyl group, it can be linked to a ligand or biomolecule by means of phosphoramidite chemistry, which ultimately forms a phosphate linkage between the dye and the biomolecule.

For examples of such labeling methods, see U.S. Pat. No. 6,027,709, which discloses many preferred linking groups, linking methods, and biomolecules that can be readily labeled. In one embodiment, solid-phase synthesis is preferred, as disclosed in U.S. Pat. No. 6,027,709.

In a preferred embodiment, the biomolecule is DNA or RNA. Use of phosphoramidite chemistry allows labeling of a DNA or an RNA during the synthesis process. The protected nucleotide is labeled while attached to a solid-phase support. The free 5'-OH group is reacted with the phosphoramidite and a tetrazole activator to form a phosphite linkage which subsequently is oxidized to phosphate. The labeled DNA or RNA is then cleaved from the solid phase by means of ammonia or by another standard procedure.

It is generally preferred to prepare a phosphoramidite of a cyanine dye to label DNA molecules in a DNA synthesizer. It is also preferred to attach the dye to the 5' end of a protected, support-bonded oligonucleotide through standard phosphoramidite chemistry. For a list of preferred label terminators for use in DNA sequencing, see U.S. Pat. No. 5,332,666.

In another preferred embodiment, the biomolecule is an antibody. It is preferred that antibody labeling is carried out in a buffer optionally including an organic co-solvent, under basic pH conditions, and at room temperature. It is also preferred that the labeled antibody be purified by dialysis or by gel permeation chromatography using equipment such as a SEPHADEX® G-50 column to remove any unconjugated compound of Formula I. Those of skill in the art will know of other ways and means for purification.

In still another preferred embodiment, the biomolecule contains a thiol group that forms the linking group by reaction with a maleimidyl substituent at $R^{16}$. In a more preferred embodiment, the biomolecule is a protein, a peptide, an antibody, a thiolated nucleotide, or a thiolated deoxynucleotide.

In yet other aspects, the linking group or biomolecule comprises a polymer. In a preferred embodiment, the polymer is a member selected from the group of a PEG, a copolymer of PEG-polyurethane, and a copolymer of PEG-polypropylene. In still yet other aspects, the linking group is a member selected from the group of a polysaccharide, a polypeptide, an oligosaccharide, a polymer, a co-polymer and an oligonucleotide.

In one aspect, biomolecules can be labeled according to the present invention by means of a kit. In certain instances, the kit comprises a buffer and a dye as disclosed in the instant application (i.e., a compound of Formula I or Formula Ia). Preferably, the kit contains a coupling buffer such as 1 M KH$_2$PO$_4$ (pH 5), optionally with added acid or base to modify the pH (e.g., pH 8.5 is preferred for reactions with succinimide esters and pH 7 is preferred for reactions with maleimides). Preferably, the buffer has a qualified low fluorescence background.

Optionally, the kit can contain a purification sub-kit. After labeling a biomolecule with a preferred dye, the labeled biomolecule may be separated from any side reaction products and any free hydrolyzed product resulting from normal hydrolysis. For biomolecules containing 13 or fewer amino acids, preparative thin layer chromatography (TLC) can remove impurities. In certain instances, preparative TLC, optionally performed with commercially available TLC kits, can be used to purify dye-labeled peptides or proteins.

For larger biomolecules such as larger peptides or proteins, a SEPHADEX® G-15, G-25, or G-50 resin may remove unwanted derivatives. In certain instances, a Gel Filtration of Proteins Kit, which is commercially available from Life Sciences, can be used to separate dye-labeled peptides and proteins from free dye. The labeled biomolecules that remain after desalting can often be used successfully without further purification. In some cases, it may be necessary to resolve and assess the activity of the different products by means of HPLC or other chromatographic techniques.

V. Bioconjugate Compounds

In another embodiment of the invention, a bioconjugate of the Formula II is provided:

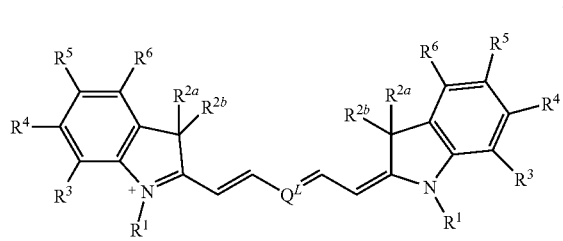

wherein $Q^L$ is a member selected from the group of a one-polymethine-carbon segment and a three-polymethine-carbon segment:

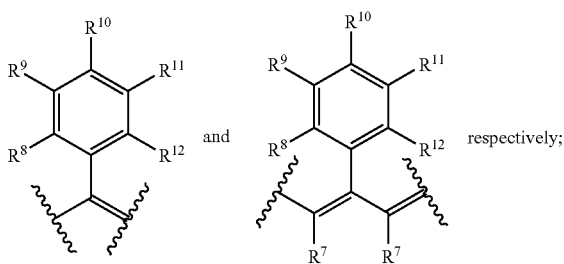

and respectively;

wherein the segment is the central portion of either a five- or a seven-polymethine-carbon polymethine bridge.

$R^1, R^{2a}, R^{2b}, R^3, R^4, R^5, R^6, R^7, R^8, R^9, R^{10}, R^{11}, R^{12}, R^{13}, R^{14}, R^{15}$, L, and Y are as previously defined for the compound of Formula I, including all preferred embodiments that are identified herein.

Each Z is an independently selected $C_1$-$C_{10}$ alkyl that is additionally substituted with one member from the group of $R^{13}$ and $R^L$. In a more preferred aspect, Z is $C_1$-$C_6$ alkyl. Alternatively, Z is interrupted by ether linkages (e.g., a polyethylene glycol oligomer). In a yet still more preferred aspect, at least one Z is -propylene-C(O)—$R^L$ or -butylene-C(O)—$R^L$. Alternatively, exactly one Z is -propylene-C(O)—$R^L$ or -butylene-C(O)—$R^L$.

In an alternative aspect, Z is optional, and $R^L$ is connected directly to -L-Y— or even directly bonded to the phenyl ring itself if L and Y are absent.

Each $R^L$ comprises 1) a linking group that connects the cyanine dye compound to a biomolecule; and 2) the biomolecule to which it is connected (i.e., the linking group and the biomolecule connected thereby), wherein the compound comprises at least one $R^L$. Preferred linking groups are indicated in Table 1 (column C). In a particularly preferred aspect, the linking group is an amide or an ester. In a more particularly preferred aspect, the linking group is an amide.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In another preferred embodiment of the bioconjugate, any preferred embodiments or aspects of the inventive compound of Formula I can included in the embodiment of a bioconjugate. Representative examples of preferred compounds of Formula I that correspond to preferred bioconjugate embodiments are described in the dependent claims of the instant application.

A more preferred aspect of the bioconjugate has the following structure:

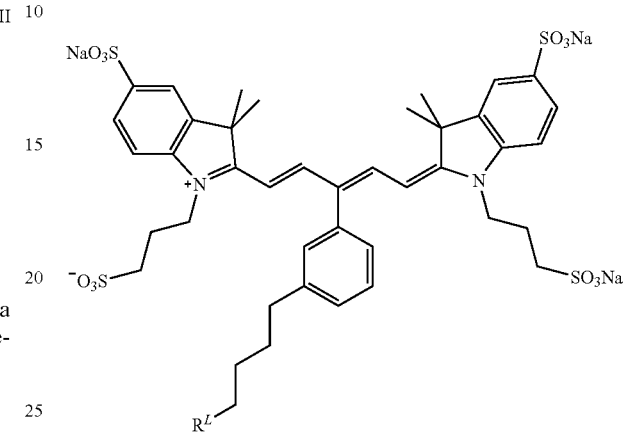

wherein $R^L$ comprises a linking group and a biomolecule connected thereby.

A second more preferred aspect of the bioconjugate has the following structure:

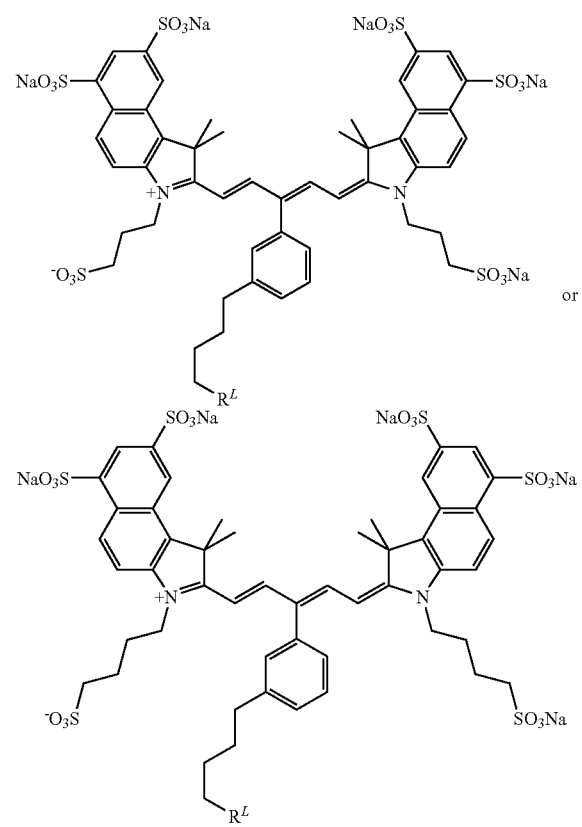

wherein $R^L$ comprises a linking group and a biomolecule connected thereby.

In certain aspects, preferred biomolecules for the instant invention include an acyclo terminator triphosphate, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like.

In still other instances, suitable nucleotides include nucleoside polyphosphates, including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof Nucleotides containing 3, 4, 5, 6, or more phosphate groups, in the polyphosphate chain, where the phosphate (e.g., $\alpha$, $\beta$, $\gamma$, $\epsilon$, or terminal phosphate), sugar, base, or combination thereof is labeled with a compound of Formula I. The polyphosphate nuceotides include, but are not limited to, tetraphosphates, pentaphosphates, hexaphosphates, heptaphosphates, and the like. The bases include for example, purines, (adenine and guanine) pyrimidines, (thymine, uracil and cytosine) and derivatives thereof In certain instances, the dye of Formula I is attached to the phosphate (e.g. $\alpha$, $\beta$, $\gamma$, $\epsilon$-phosphate or terminal phosphate) through a phosphorothioate linkage (see, for example, U.S. Pat. No. 6,323,186, incorporated herein by reference), heteroatom, or functional group A, or B, resulting in linkage C of Table I. See also U.S. Pat. No. 6,399,335 (incorporated herein by reference) entitled "$\gamma$-phosphoester nucleoside triphosphates," which provides methods and compositions for polymerizing particular nucleotides with a polymerase using $\gamma$-phosphoester linked nucleoside triphosphates. Other ways of linking the compounds of Formula I to a nucleotide are known to those of skill in the art. Using these nucleotides with a DNA polymerase can lead to identification of specific nucleotides in a DNA or RNA sequence by identification of the labeled pyrophosphate or polyphosphate released upon incorporation of the nucleotide base into RNA or DNA. (See for example, U.S. Pat. No. 6,232,075, US Pub. No. 2004/0241716 and U.S. Pat. No. 7,452,698 each of which is incorporated herein by reference).

More preferred aspects include an antibody, an avidin, and a streptavidin. Even more preferred aspects include a goat anti-mouse (GAM) antibody, a goat anti-rabbit (GAR) antibody, and streptavidin.

In certain other aspects, preferred biomolecules for the instant invention include somatostatin, endostatin, a carbohydrate, an oligosaccharide, an aptamer, a liposome, PEG, an angiopoietin, angiostatin, angiotensin II, $\alpha_2$-antiplasmin, annexin V, $\beta$-cyclodextrin tetradecasulfate, endoglin, endosialin, endostatin, epidermal growth factor, fibrin, fibrinopeptide $\beta$, fibroblast growth factor, FGF-3, basic fibronectin, fumagillin, heparin, hepatocyte growth factor, hyaluronan, aninsulin-like growth factor, an interferon-$\alpha$, $\beta$ inhibitor, IL inhibitor, laminin, leukemia inhibitory factor, linomide, a metalloproteinase, a metalloproteinase inhibitor, an antibody, an antibody fragment, an acyclic RGD peptide, a cyclic RGD peptide, placental growth factor, placental proliferin-related protein, plasminogen, plasminogen activator, plasminogen activator inhibitor-1, a platelet activating factor antagonist, platelet-derived growth factor, a platelet-derived growth factor receptor, a platelet-derived growth factor receptor, platelet-derived endothelial cell growth factor, pleiotropin, proliferin, proliferin-related protein, a selectin, SPARC, a snake venom, substance P, suramin, a tissue inhibitor of a metalloproteinase, thalidomide, thrombin, thrombin-receptor-activating tetradecapeptide, transformin growth factor-$\alpha$, $\beta$, transforming growth factor receptor, tumor growth factor-$\alpha$, tumor necrosis factor, vitronectin, and the like.

In still other aspects, preferred biomolecules include a carbohydrate and a carbohydrate derivative. Representative examples include glucosamine, a glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, and a derivative thereof Even more preferred biomolecules include 2-deoxy-D-glucose, 2-deoxy-L-glucose, and racemic 2-deoxyglucose.

In yet still other aspects, the biomolecule can be a ligand that has affinity for a receptor selected from the group of EGFR, Her2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocordicosteroid receptor, Retinoid-X receptor, RHAMM, high affinity folate receptors, Met receptor, estrogen receptor and Ki67.

Alternatively, the biomolecule is selected from the group of somatostatin, endostatin, a carbohydrate, a monosaccharide, a disaccharide, a trisaccharide, an oligosaccharide, aptamer, liposome and polyethylene glycol.

In yet another aspect, the biomolecule is a small-molecule drug or drug-like molecule such as a tetracycline antibiotic, a tetracycline derivative, and calcein.

VI. Methods of Imaging

In another embodiment, the compounds of Formula I can be used as in vitro or in vivo optical imaging agents of tissues and organs in various biomedical applications. In one embodiment, the present invention provides a method for imaging, the method comprising administering a compound of Formula I.

In certain preferred aspects of the invention, any of the embodiments or aspects of the inventive compound of Formula I or Ia that are described herein can be used in the method of imaging. Representative examples of preferred compounds for use in the method are described in the specification and the dependent claims of the instant application.

In another embodiment, the present invention provides a method for imaging, the method comprising administering a compound of Formula II. In a preferred aspect, $R^L$ comprises a biomolecule that is selected from the group of 2-deoxy-D-glucose, 2-deoxy-L-glucose, and racemic 2-deoxyglucose.

In certain preferred aspects of the invention, any of the embodiments or aspects of the inventive compound of Formula II that are described herein can be used in the method of imaging. Representative examples of preferred compounds for use in the method are described in the specification and the dependent claims of the instant application.

In certain preferred aspects, the compounds of the present invention are used as in vivo imaging agents of tissues and organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and the like. In one aspect, the compounds of the invention are useful for the detection of the presence of tumors and other abnormalities by monitoring the blood clearance profile of the dyes. In another aspect of the invention, the compounds are useful for laser assisted guided surgery for the detection of micro-metastases of tumors upon laparoscopy. In yet another aspect, the compounds are useful in the diagnosis of atherosclerotic plaques and blood clots.

In further aspects, the compounds of the present invention are used in the imaging of: (1) ocular diseases in ophthalmology, for example, to enhance visualization of chorioretinal diseases, such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endocsopic catheters; (5) breast tumors via 2D- or 3D-image reconstruction; and (6) brain tumors, perfusion, and stroke via 2D- or 3D-image reconstruction.

The compounds of the invention that are bioconjugates are particularly useful for imaging tumors, tissues, and organs in a subject. For example, the existence of cancer cells or cancer tissues can be verified by labeling an anti-tumor antibody with a compound of Formula I and then administering the bioconjugated antibody to the subject for detection and imaging of the tumor. Conjugates between the dye compound and other antibodies, peptides, polypeptides, proteins, ligands for cell surface receptors, small molecules, and the like are also useful agents for the in vivo imaging of tumors, tissues, and organs in a subject.

The compounds of the invention may be administered either systemically or locally to the organ or tissue to be imaged, prior to the imaging procedure. In one aspect, the compounds are administered intravenously. In another aspect, the compounds are administered parenterally. In yet another aspect, the compounds are administered enterally. The compositions used for administration of the compound typically contain an effective amount of the compound or conjugate along with conventional pharmaceutical carriers and excipients appropriate for the type of administration contemplated. For example, parenteral formulations advantageously contain a sterile aqueous solution or suspension of a compound of Formula I or a bioconjugate of Formula II. Compositions for enteral administration typically contain an effective amount of the compound or bioconjugate in aqueous solution or suspension that may optionally include buffers, surfactants, thixotropic agents, flavoring agents, and the like.

The compositions are administered in doses effective to achieve the desired optical image of a tumor, tissue, or organ. Such doses may vary widely, depending upon the particular compound or bioconjugate employed, the tumor, tissue, or organ subjected to the imaging procedure, the imaging equipment being used, and the like.

The method of the present invention provides for administering to the subject a therapeutically effective amount of a compound; a targeting agent, such as a bioconjugate; or mixtures thereof. In one aspect, the targeting agent selectively binds to the target tissue. Light at a wavelength or waveband corresponding to that which is absorbed by the photosensitizing agent is then administered. In another aspect, the compounds of the present invention act agents capable of binding to one or more types of target cells or tissues, when exposed to light of an appropriate waveband, absorb the light, causing substances to be produced that illuminate, impair or destroy the target cells or tissues. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

In yet another aspect, the compounds of the present invention are administered by any means known, including, but not limited to, ingestion, injection, transcutaneous administration, transdermal administration, and the like. Preferably, the compounds are administered transcutaneously to a subject.

In further aspects of the invention, the target tumor, tissue, or organ for treatment is selected from the group of vascular endothelial tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, neuronal tissue or diseased neuronal tissue, and diseased cells in which the disease is one of an autoimmune and an inflammatory disease. In yet a further aspect, the target tissue is a lesion in the vascular system of a type selected from the group of atherosclerotic lesions, arteriovenous malformations, aneurysms, and venous lesions.

In still further aspects, the forms of energy include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Compounds of the instant invention typically have one or more absorption wavebands that excite them to produce the substances which illuminate, damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins. More preferably, the radiation wavelength or waveband is within the NIR range of about 600 nm to about 1000 nm or a related range thereof (e.g., the ranges that are described in the instant claims).

In certain aspects, the compounds of the present invention are used to directly stain or label a sample so that the sample can be identified or quantitated. For instance, such compounds can be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable optical response as used herein includes a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some compounds of the invention may exhibit little fluorescence emission, but are still useful as chromophoric dyes. Such chromophores are useful as energy donors in fluorescence (or Förster) resonance energy transfer (FRET) applications, or to impart the desired color to a sample or portion of a sample.

FRET is a process by which a donor molecule (e.g., a dye) absorbs light, entering an excited state. Rather than emitting light, the first molecule transfers its excited state to a acceptor molecule with other properties (e.g., a dye fluorescing at a different wavelength or a quencher), and the acceptor fluoresces or quenches the excitation. Because the efficiency of the transfer is dependant on the two molecules' proximity, it can indicate information about molecular complex formation or biomolecular structure. It can also indicate where a particular complex is located within a cell or organism (e.g., FRET optical microscopy). For ways to use similar dyes as acceptors (quenchers) in FRET processes, see X. Peng, H. Chen, D. R. Draney, W. Volcheck, A. Schultz-Geschwender, and D. M. Olive, "A nonfluorescent, broad-range quencher dye for Förster resonance energy transfer assays," Anal. Biochem 2009, 388(2): 220-228.

In certain instances, a suitable FRET acceptor is disclosed in WO 2007/005222 incorporated herein by reference. The compounds include the following essentially non-fluorescent cyanine dyes of formula III:

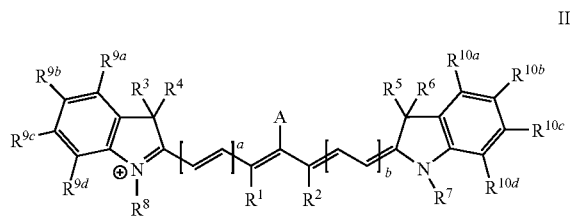

wherein the substituents in formula III are defined as follows: $R^1$ and $R^2$ are each independently selected from the group consisting of hydrogen and optionally substituted $(C_1\text{-}C_6)$ alkyl. Alternatively, $R^1$ and $R^2$ together with the

group to which they are bonded form a 5- to 7-membered ring, the ring being optionally substituted with 1 to 4 substituents selected from the group consisting of halogen, cyano, sulfonate, $(C_1\text{-}C_8)$haloalkyl, hydroxy, $(C_1\text{-}C_6)$alkoxy and optionally substituted $(C_1\text{-}C_8)$alkyl.

In formula III, $R^3$ and $R^4$ are each independently an optionally substituted $(C_1\text{-}C_6)$alkyl, and may optionally join together with the atoms to which they are attached to form a 5- to 7-membered carbocyclic ring; or alternatively, the substituents $R^3$ and $R^4$ are replaced with the group

wherein B is $(C_1\text{-}C_6)$alkyl; or B and $R^{9a}$ together with the carbon atoms to which they are attached join to form a 5- or 6-membered ring optionally having 1 or 2 heteroatoms and optionally having up to 3 double bonds.

The substituents $R^5$ and $R^6$ are each independently an optionally substituted $(C_1\text{-}C_6)$alkyl, and may optionally join together with the atom to which they are attached to form a ring.

The substituents $R^7$ and $R^8$ are each independently selected from the group consisting of optionally substituted $(C_1\text{-}C_6)$ alkyl, optionally substituted aryl$(C_1\text{-}C_6)$alkyl, optionally substituted heteroaryl$(C_1\text{-}C_6)$alkyl, —$(CH_2)_cR^{13}$ and —$(CH_2)_dR^{15}$. Indices c and d are each independently an integer from 1-50. $R^{13}$ is a functional group that does not directly react with a carboxyl, hydroxyl, amino or thio group on a biomolecule. $R^{15}$ is a linking group selected from the group consisting of mercapto, amino, haloalkyl, phosphoramidityl, N-hydroxy succinimidyl ester, sulfo N-hydroxysuccinimidyl ester, isothiocyanato, iodoacetamidyl, maleimidyl and an activated carboxylic acid.

The substituents $R^{9a\text{-}9d}$ and $R^{10a\text{-}10d}$ are each independently selected from the group consisting of hydrogen, optionally substituted $(C_1\text{-}C_6)$alkyl, —$SO_3Cat^+$, halogen, —$C(O)OR^{11}$, —$C(O)NR^{11}R^{12}$, —$C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$(CH_2)_dR^{15}$, —$S(O)_2NR^{12}(CH_2)_dR^{15}$, —$R^{15}$ and —$NR^{20}R^{21}$, wherein $Cat^+$ is a cation. The substituents $R^{11}$ and $R^{12}$ are each independently selected from the group consisting of hydrogen and $(C_1\text{-}C_6)$alkyl; $R^{20}$ and $R^{21}$ are each independently selected from the group consisting of hydrogen, optionally substituted $(C_1\text{-}C_8)$alkyl, $CatO_3S(C_1\text{-}C_{50})$alkylene.

Alternatively, any two substituents of $R^{10a\text{-}10d}$ located on adjacent atoms, together with the atoms to which they are attached, join to form a 5- or 6-membered ring optionally having 1 or 2 heteroatoms and optionally having up to 3 double bonds; wherein the ring may be further substituted with 1 to 3 substituents selected from the group consisting of optionally substituted $(C_1\text{-}C_6)$alkyl, —$SO_3^-Cat$, halogen, —$C(O)OR^{11}$, —$C(O)NR^{11}R^{12}$, —$C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$S(O)_2NR^{12}(CH_2)_dR^{15}$, —$R^{15}$ and —$NR^{20}R^{21}$.

In formula III, the variable a is an integer from 0-3 and the variable b is an integer from 0-2. A is selected from the group consisting of hydrogen, halogen, cyano, optionally substituted $(C_1\text{-}C_8)$alkyl, optionally substituted $(C_1\text{-}C_6)$dialkylamino, optionally substituted alkylthio, —$(CH_2)_dR^{15}$, —$R^{15}$, optionally substituted $(C_1\text{-}C_6)$heteroalkyl, phenoxy and an optionally substituted aryloxy group having the formula

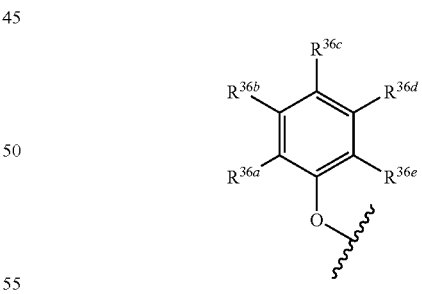

wherein $R^{36a}$-$R^{36e}$ are each independently selected from the group consisting of hydrogen, —$SO_3Cat^+$, —$(CH_2)_dR^{15}$, —$C(O)O(CH_2)_dR^{15}$, —$C(O)NR^{11}(CH_2R^{15}$, —$NR^{12}C(O)O(CH_2)_dR^{15}$, —$S(O)_2NR^{12}(CH_2)_dR^{15}$, —$R^{15}$, $(C_1\text{-}C_6)$alkyl, carboxyl and $NR^{20}R^{21}$.

The compounds of formula III have at least one linking group. In certain aspects, the compounds of the invention have one or more linking groups such as for example, 1, 2, 3 or more linking groups. The at least one linking group $R^{15}$ can be attached at various positions on the compound of formula III.

For biological applications, the compounds of the invention are typically used in an aqueous, mostly aqueous or aqueous-miscible solution prepared according to methods generally known in the art. The exact concentration of compound is dependent upon the experimental conditions and the desired results, but ranges of 0.00001 mM up to 0.1 mM, such as about 0.001 mM to about 0.01 mM, are possible. The optimal concentration is determined by systematic variation until satisfactory results with minimal background fluorescence is accomplished.

In certain aspects, the method may involve treatment of an animal or sample with a dose comprising a compound of Formula I, a bioconjugate of Formula II, or any of the aspects or embodiments thereof. The exact concentration of compound is dependent upon the subject and the desired results. In certain embodiments, a dose of at least about 0.001, 0.005, 0.01, 0.025, 0.05, or 0.075 mg/kg is used. Alternatively, a dose of at most about 0.001, 0.005, 0.01, 0.025, 0.05, or 0.075 mg/kg is used. In certain other embodiments, a dose of at least about 0.1, 0.25, 0.5, or 0.75 mg/kg is used. Alternatively, a dose of at most about 0.1, 0.25, 0.5, or 0.75 mg/kg is used. In still other embodiments, a dose of at least about 0.1, 0.25, 0.5, or 0.75 mg/kg is used. Alternatively, a dose of at most about 0.1, 0.25, 0.5, or 0.75 mg/kg is used. In yet still other embodiments, a dose of at least about 1, 2.5, 5, or 7.5 mg/kg is used. Alternatively, a dose of at most about 1, 2.5, 5, or 7.5 mg/kg is used. In additional other embodiments, a dose of at least about 10, 25, 50, or 75 mg/kg is used. Alternatively, a dose of at most about 10, 25, 50, or 75 mg/kg is used. In additional still other embodiments, a dose of at least about 100, 250, 500, or 750 mg/kg is used. Alternatively, a dose of at most about 100, 250, 500, or 750 mg/kg is used. Other amounts for administration of an effective dose may be readily determined by one of skill in the art.

The compounds are most advantageously used to stain samples with biological components. The sample can comprise heterogeneous mixtures of components (e.g., mixtures including intact cells, fixed cells, cell extracts, bacteria, viruses, organelles, and combinations thereof), or a single component or homogeneous group of components (e.g. natural or synthetic amino acid, nucleic acid or carbohydrate polymers, or lipid membrane complexes). Within the concentrations of use, these compounds are generally non-toxic to living cells and other biological components.

The compound is combined with the sample in any way that facilitates contact between the compound and the sample components of interest. Typically, the compound or a solution containing the compound is simply added to the sample. Certain compounds of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP, can be used to introduce selected compounds into cells. Alternatively, selected dye compounds can be physically inserted into cells, e.g., by pressure microinjection, scrape loading, patch clamp methods, or phagocytosis.

At any time after or during staining, the sample is illuminated with a wavelength of light selected to give a detectable optical response, and observed with a means for detecting the optical response. Equipment that is useful for illuminating the compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred aspects of the invention are compounds that are excitable at or near the wavelengths 633-636 nm, 647 nm, 649 nm, 651 nm, 647-651 nm, 660 nm, 674 nm, 675 nm, 678 nm, 680 nm, 674-680 nm, 685 nm, 674-685 nm, 680-685 nm, and beyond 700 nm, such as 780 nm, 810 nm and 850 nm, as these regions closely match the output of exemplary compounds or of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined by means of a flow cytometer, examination of the sample optionally includes sorting portions of the sample according to their fluorescence response.

VII. Examples

Below, the present invention will be described by way of examples, which are provided for illustrative purposes only. Accordingly, they are not to be construed as limiting the scope of the present invention as defined by the appended claims.

Example 1

Preparation of 6-Hydrazino-1,3-naphthalene Disulfonated Salt

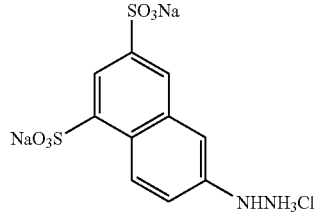

6-Hydrazino-1,3-naphthalene Disulfonated Salt (1)

6-Amino-1,3-naphthalene disulfonate disodium salt (25 g, 72 mmol) was dissolved in 150 ml of water and added to 50 ml of concentrated hydrochloric acid. The slurry was cooled to about 0° C. in an ice/salt bath, and sodium nitrite (5.46 g, 79.2 mmol) was added in 25 ml of cold water dropwise over 10 minutes. Stannous chloride (20.42 g, 108 mmol) was dissolved in 15 ml concentrated hydrochloric acid, cooled to 0° C. and added to the reaction mixture over 20 minutes. The resulting solution was allowed to warm to room temperature with stirring over 3 hours. The solution was reduced in volume by rotary evaporation, and the product was precipitated by the addition of isopropanol. Compound 1 was filtered, washed with isopropanol, and dried under vacuum.

Example 2

Preparation of 2,3,3-Trimethylbenzindole-6,8-disulfonate Salt

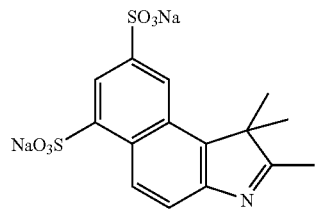

2,3,3-Trimethylbenzindole-6,8-disulfonate Salt (2)

6-Hydrazino-1,3-naphthalene disulfonated salt 1 (10 g, 25 mmol), isopropyl methyl ketone (12 g, 140 mmol) and potassium acetate (6 g, 61 mmol) were combined in 75 ml glacial acetic acid and heated to 145° C. for 22 hours. The solution was cooled, and the acetic acid was removed by rotary evaporation. The residue was dissolved in methanol and filtered. The compound 2 was then precipitated from the methanol filtrate with isopropanol, filtered, washed with isopropanol and ether, and dried under vacuum.

Example 3

Preparation of Sodium 1,1,2-Trimethyl-3-(3-sulfonatopropyl)-1H-benzo[e]indolium-6,8-disulfonate

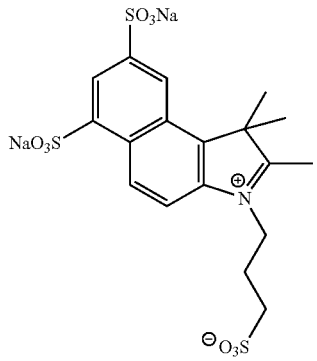

Sodium 1,1,2-Trimethyl-3-(3-sulfonatopropyl)-1H-benzo[e]indolium-6,8-disulfonate (3)

2,3,3-Trimethylbenzindole-6,8-disulfonate 2 (2.2 g, 5 mmol) was stirred in 50 ml of dry 1,2-dichlorobenzene. 1,3-propanesultone (2.8 g, 23 mmol) was added, and the solution was heated to 145° C. in a sealed tube for 15 hours. The solution was cooled, and the solvent was decanted off The solid product 3 was washed on a filter with three 50 ml portions of isopropanol followed by 50 ml of ether and dried under vacuum, resulting in a dark purple solid (2.5 g, 90%).

Example 4

Preparation of Sodium 1,1,2-Trimethyl-3-(3-sulfonatobutyl)-1H-benzo[e]indolium-6,8-disulfonate

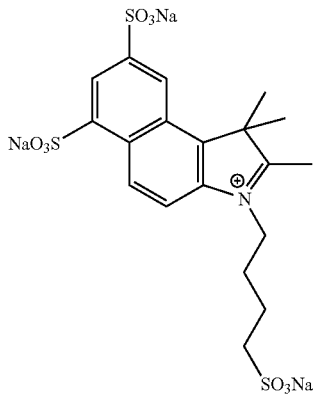

Sodium 1,1,2-Trimethyl-3-(3-sulfonatobutyl)-1H-benzo[e]indolium-6,8-disulfonate (4)

Compound 4 was prepared analogously to compound 3 (Example 3), except that 1,4-butanesultone is used as a starting material.

Example 5

Preparation of (E)-N—((Z)-2-Bromo-3-(phenylamino)allylidene)benzenaminium Bromide

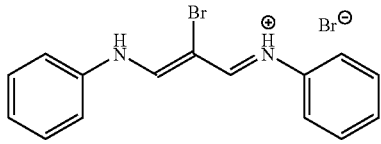 [SMILES: BrC(=C\Nc1ccccc1)/C=[NH+]/c1ccccc1 ; [Br-]]

(E)-N—((Z)-2-Bromo-3-(phenylamino)allylidene) benzenaminium Bromide (5)

The procedure as disclosed in the literature (Simonis, H. *Ber. Deut. Chem. Ges.* 1901, 34, 509; U.S. Pat. No. 6,747,159) is used. 3.54 g of aniline are dissolved in 15 ml of ethanol in a 100 ml beaker. Separately, 5 g of mucobromic acid are dissolved in 15 ml of ethanol in a 100 ml Erlenmeyer flask. This solution is added dropwise to the aniline/ethanol solution, with cooling. The reaction mixture turns immediately yellow, then orange, with development of $CO_2$. At the end of the addition, the mixture is heated in a water bath until its volume is reduced by one half. The resulting solution is cooled with an ice-salt mixture, forming a yellow crystalline precipitate. This solid is collected on a fritted glass filter to afford pure product 5; additional product 5 can be recovered from concentration and recrystallization of the mother liquor.

Example 6

Preparation of Sodium 2-((1E,3Z,5E)-3-Bromo-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

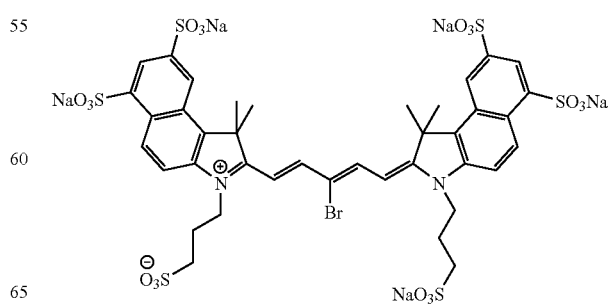

Sodium 2-((1E,3Z,5E)-3-Bromo-5-(1,1-dimethyl-6,
8-disulfonato-3-(3-sulfonatopropyl)-1H-benzo[e]
indol-2(3H)-ylidene)penta-1,3-dienyl)-1,1-dimethyl-
3-(3-sulfonatopropyl)-1H-benzo[e]indolium-6,8-
disulfonate (6)

A 100 ml round bottom flask fitted with a reflux condenser was charged with sodium 1,1,2-trimethyl-3-(3-sulfonatopropyl)-1H-benzo[e]indolium-6,8-disulfonate (3) (565 mg, 1 mmol), (E)-N—(Z)-2-bromo-3-(phenylamino)allylidene)benzenaminium bromide (5) (150 mg, 0.5 mmol), and pyridine (1 ml). Acetic anhydride (10 ml) was added to the flask, and the mixture was heated at 115° C. for 2 h, cooled to room temperature, and diluted with 25 ml of ethyl ether. The resulting dark blue dye precipitate was collected by filtration, then dissolved in 20 ml of water and purified by preparative reverse-phase HPLC to afford the compound 6 as a blue powder (285 mg, 50%; UV/vis absorption max 674 nm).

Example 7

Preparation of Sodium 2-((1E,3Z,5E)-3-Bromo-5-(1,
1-dimethyl-6,8-disulfonato-3-(3-sulfonatobutyl)-1H-
benzo[e]indol-2(3H)-ylidene)penta-1,3-dienyl)-1,1-
dimethyl-3-(3-sulfonatobutyl)-1H-benzo[e]indolium-
6,8-disulfonate

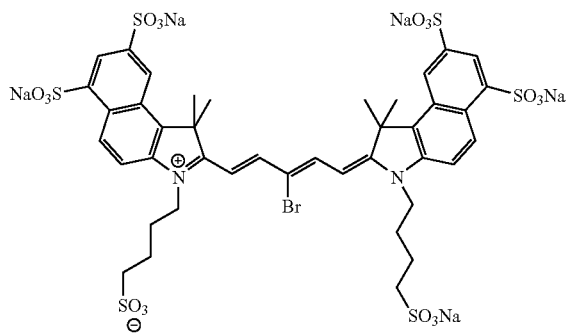

Sodium 2-((1E,3Z,5E)-3-Bromo-5-(1,1-dimethyl-6,
8-disulfonato-3-(3-sulfonatobutyl)-1H-benzo[e]in-
dol-2(3H)-ylidene)penta-1,3-dienyl)-1,1-dimethyl-3-
(3-sulfonatobutyl)-1H-benzo[e]indolium-6,8-
disulfonate (7)

Compound 7 was prepared analogously to compound 6 (Example 6), except that compound 4 is used as a starting material.

Example 8

Preparation of Sodium 2-((1E,3Z,5E)-3-(3-(4-Car-
boxybutyl)phenyl)-5-(1,1-dimethyl-6,8-disulfonato-
3-(3-sulfonatopropyl)-1H-benzo[e]indol-2(3H)-
ylidene)penta-1,3-dienyl)-1,1-dimethyl-3-(3-
sulfonatopropyl)-1H-benzo[e]indolium-6,8-
disulfonate

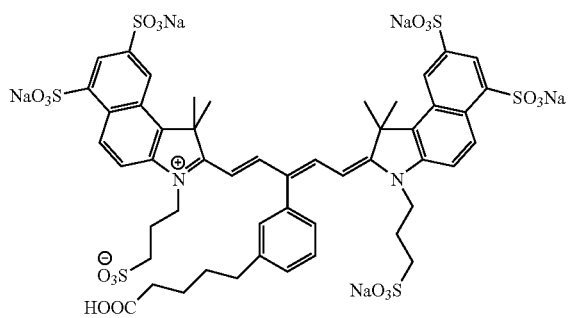

Sodium 2-((1E,3Z,5E)-3-(3-(4-Carboxybutyl)phe-
nyl)-5-(1,1-dimethyl-6,8-disulfonato-3-(3-sulfonato-
propyl)-1H-benzo[e]indol-2(3H)-ylidene)penta-1,3-
dienyl)-1,1-dimethyl-3-(3-sulfonatopropyl)-1H-
benzo[e]indolium-6,8-disulfonate (8)

Compound 6 (80 mg), 3-(4-carboxybutyl)phenylboronic acid (40 mg), and cesium carbonate (20 mg) are stirred into 1:1 water:ethanol (10 ml) under nitrogen at room temperature. Tetrakis(triphenylphosphine)palladium(0) (10 mg) is added to the reaction mixture. The mixture was refluxed for 4 hours, and the solvent and volatile compounds are evaporated under vacuum. The crude product is purified by flash chromatography on reverse-phase C18-functionalized silica by eluting with a 1:4 acetonitrile:water mixture. The purified product 8 has UV/vis absorption max of $\lambda_{MeOH}$=680 nm, $\epsilon$=229,000; $\lambda_{PBS}$676 nm, $\epsilon$=239,000.

Example 9

Preparation of Sodium 2-((1E,3Z,5E)-5-(1,1-Dim-
ethyl-6,8-disulfonato-3-(3-sulfonatopropyl)-1H-
benzo[e]indol-2(3H)-ylidene)-3-(3-(5-(2,5-dioxopyr-
rolidin-1-yloxy)-5-oxopentyl)phenyl)penta-1,3-
dienyl)-1,1-dimethyl-3-(3-sulfonatopropyl)-1H-
benzo[e]indolium-6,8-disulfonate

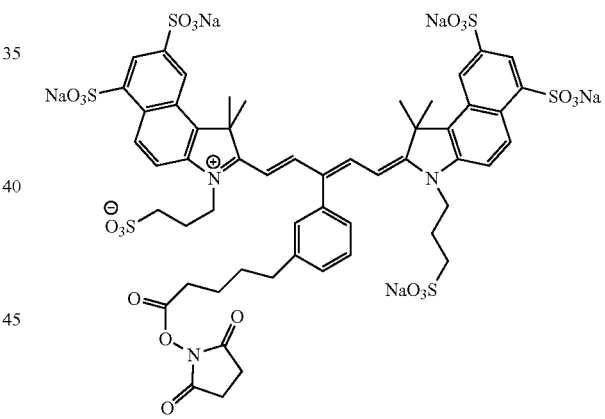

Sodium 2-((1E,3Z,5E)-5-(1,1-Dimethyl-6,8-disul-
fonato-3-(3-sulfonatopropyl)-1H-benzo[e]indol-2
(3H)-ylidene)-3-(3-(5-(2,5-dioxopyrrolidin-1-yloxy)-
5-oxopentyl)phenyl)penta-1,3-dienyl)-1,1-dimethyl-
3-(3-sulfonatopropyl)-1H-benzo[e]indolium-6,8-
disulfonate (9)

To a solution of compound 8 (200 mg) in dry DMSO (15 ml) was added triethylamine (150 μL) and N,N'-disuccinimidyl carbonate (82 mg). The mixture was stirred at room temperature for 2 hours, and the solvent was removed to yield the succinimidyl ester.

Example 10

Preparation of Sodium 2-((1E,3Z,5E)-3-(3-(2-Carboxyethyl)phenyl)-5-(1,1-dimethyl-6,8-disulfonato-3-(4-sulfonatobutyl)-1H-benzo[e]indol-2(3H)-ylidene)penta-1,3-dienyl)-1,1-dimethyl-3-(4-sulfonatobutyl)-1H-benzo[e]indolium-6,8-disulfonate

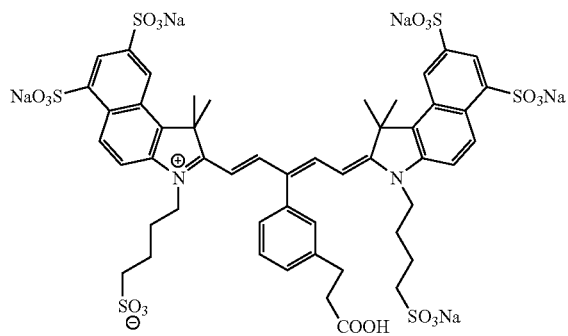

Sodium 2-((1E,3Z,5E)-3-(3-(2-Carboxyethyl)phenyl)-5-(1,1-dimethyl-6,8-disulfonato-3-(4-sulfonatobutyl)-1H-benzo[e]indol-2(3H)-ylidene)penta-1,3-dienyl)-1,1-dimethyl-3-(4-sulfonatobutyl)-1H-benzo[e]indolium-6,8-disulfonate (10)

Compound 10 was prepared analogously to compound 8 (Example 8), except that 3-(3-boronophenyl)propionic acid is used as a starting material.

Example 11

Preparation of Sodium 2-((1E,3Z,5E)-5-(1,1-Dimethyl-6,8-disulfonato-3-(4-sulfonatobutyl)-1H-benzo[e]indol-2(3H)-ylidene)-3-(3-(3-(2,5-dioxopyrrolidin-1-yloxy)-3-oxopropyl)phenyl)penta-1,3-dienyl)-1,1-dimethyl-3-(4-sulfonatobutyl)-1H-benzo[e]indolium-6,8-disulfonate

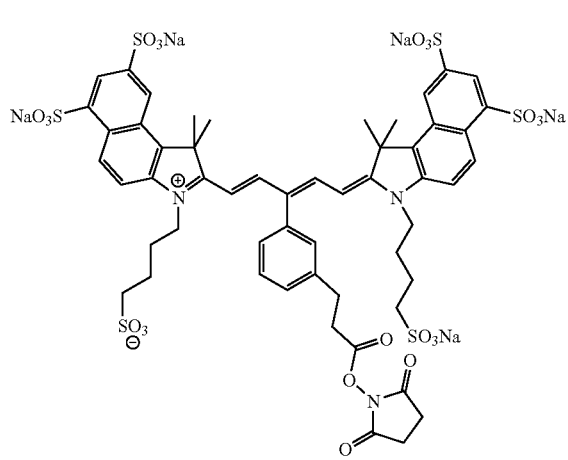

Sodium 2-((1E,3Z,5E)-5-(1,1-Dimethyl-6,8-disulfonato-3-(4-sulfonatobutyl)-1H-benzo[e]indol-2(3H)-ylidene)-3-(3-(3-(2,5-dioxopyrrolidin-1-yloxy)-3-oxopropyl)phenyl)penta-1,3-dienyl)-1,1-dimethyl-3-(4-sulfonatobutyl)-1H-benzo[e]indolium-6,8-disulfonate (11)

Compound 11 was prepared analogously to compound 9 (Example 9), except that compound 10 was used as a starting material.

Example 12

Preparation of Sodium 2,3,3-Trimethyl-1-(3-sulfonatopropyl)-3H-indolium-5-sulfonate

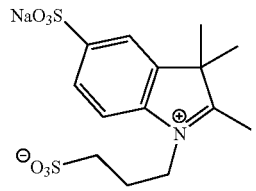

Sodium 2,3,3-Trimethyl-1-(3-sulfonatopropyl)-3H-indolium-5-sulfonate (12)

A mixture of 14 g of commercially available 5-sulfo-2,3,3-trimethylindolinium inner salt and 14 g propanesultone in 100 ml dicholorobenzene was heated at 110° C. for 2 hours. After cooling, the solvent was decanted and the solid is then dissolved in 100 ml of acetonitrile and 300 ml of ethyl acetate is added. The resulting sticky solid was again stirred in 300 ml of ethyl acetate to yield 20 g of the product 12.

Example 13

Preparation of Sodium 2-((1E,3Z,5E)-3-Bromo-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate

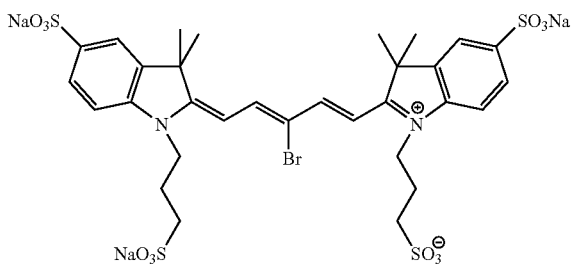

Sodium 2-((1E,3Z,5E)-3-Bromo-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate (13)

Compound 13 was prepared analogously to compound 6 (Example 6), except that compound 12 is used as starting materials. UV/vis absorption max: $\lambda_{MeOH}$=650 nm.

Example 14

Preparation of Sodium 2-((1E,3Z,5E)-3-(3-(4-Carboxybutyl)phenyl)-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate

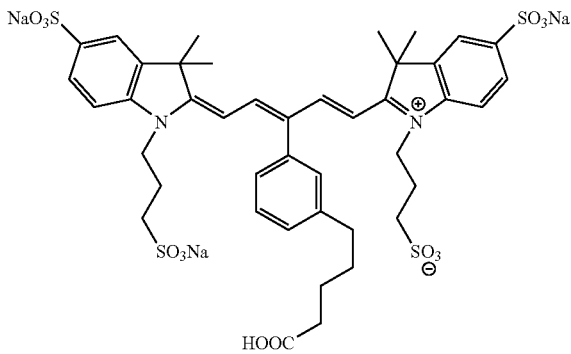

Sodium 2-((1E,3Z,5E)-3-(3-(4-Carboxybutyl)phenyl)-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate (14)

Compound 14 was prepared analogously to compound 8 (Example 8), except that compound 13 was used as starting materials. UV/vis absorption max: $\lambda_{H2O}$=649 nm, $\epsilon$=190,000; $\lambda_{MeOH}$=650 nm, $\epsilon$=180,000; MS calculated (found) for (M+1)$^+$935.21 (935.3).

Example 15

Preparation of Sodium 2-((1E,3Z,5E)-5-(3,3-Dimethyl-5-sulfonato-1-(3-sulfonatopropyl)indolin-2-ylidene)-3-(3-(5-(2,5-dioxopyrrolidin-1-yloxy)-5-oxopentyl)phenyl)penta-1,3-dienyl)-3,3-dimethyl-1-(3-sulfonatopropyl)-3H-indolium-5-sulfonate

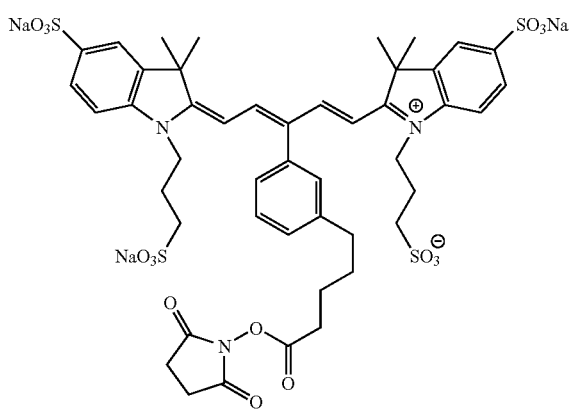

Sodium 2-((1E,3Z,5E)-5-(3,3-Dimethyl-5-sulfonato-1-(3-sulfonatopropyl)indolin-2-ylidene)-3-(3-(5-(2,5-dioxopyrrolidin-1-yloxy)-5-oxopentyl)phenyl)penta-1,3-dienyl)-3,3-dimethyl-1-(3-sulfonatopropyl)-3H-indolium-5-sulfonate (15)

Compound 15 was prepared analogously to compound 9 (Example 9), except that compound 14 is used as a starting material.

Example 16

Preparation of Sodium 2-((1E,3Z,5E)-3-(3-(Carboxymethoxy)-5-fluorophenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

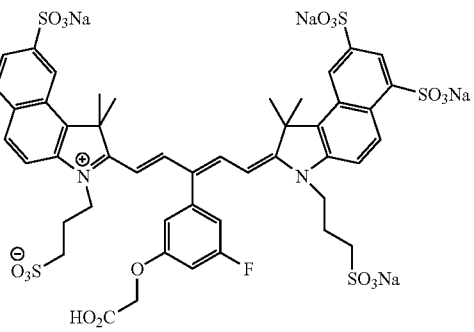

Sodium 2-((1E,3Z,5E)-3-(3-(Carboxymethoxy)-5-fluorophenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate (16)

Compound 16 was prepared analogously to compound 8 (Example 8), except that 2-(3-borono-fluorophenoxy)acetic acid is used as a starting material. The purified product 16 has UV/vis absorption max of $\lambda_{MeOH}$=677 nm, $\epsilon$=205,000; $\lambda_{PBS}$=674 nm, $\epsilon$=195,000.

Example 17

Preparation of Sodium 2-((E)-2-((E)-2-(2,6-Difluoro-4-methoxyphenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

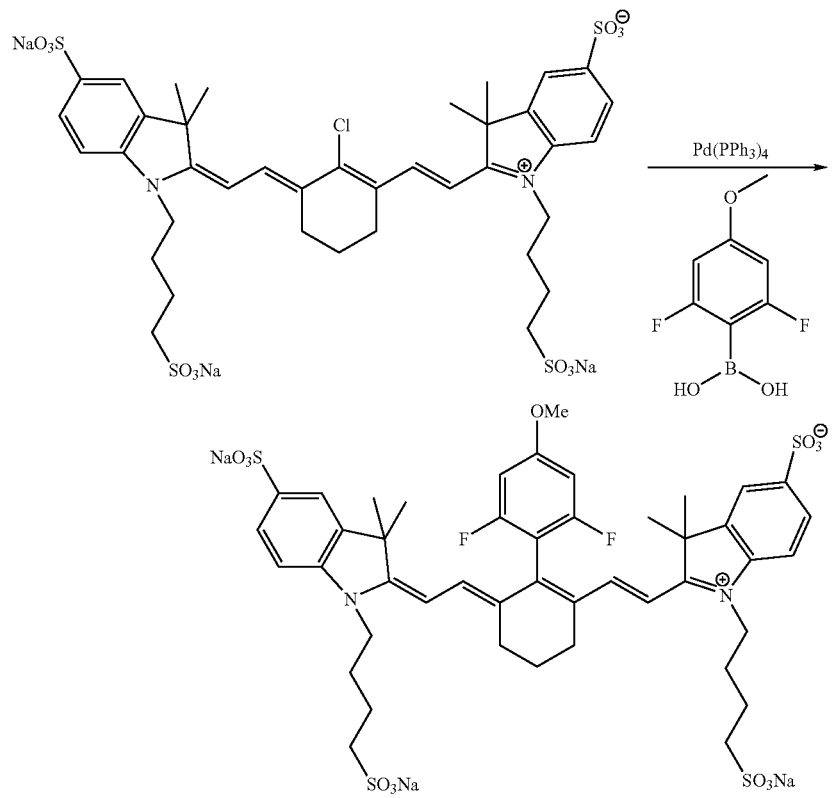

Sodium 2-((E)-2-((E)-2-(2,6-Difluoro-4-methoxyphenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (17)

Compound 17 was prepared by combining 100 mg of the chloro dye precursor shown above, 70 mg of 2,6-difluoro-4-methoxyphenylboronic acid, and 10 mg of Pd(PPh$_3$)$_4$. The admixture was refluxed with 50 ml H$_2$O for 5 h under nitrogen gas. The green solution was separated by reverse-phase HPLC using C18-functionalized silica and an 15:85 acetonitrile/H$_2$O gradient. The purified product has a UV/vis absorption max of $\lambda_{MeOH}$=783 nm, $\lambda_{PBS}$=777 nm, and emission at 805 nm.

Example 18

Preparation of Sodium 2-((E)-2-((E)-2-(3-Butoxy-2,6-difluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

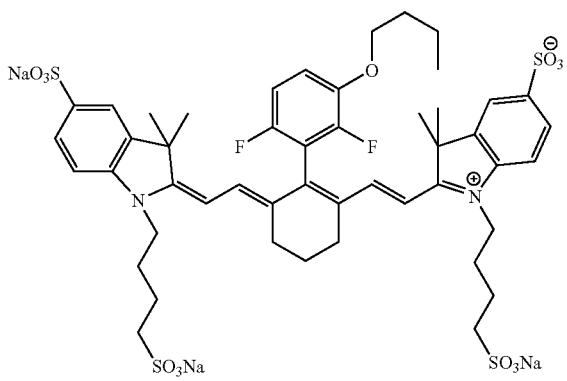

Sodium 2-((E)-2-((E)-2-(3-Butoxy-2,6-difluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (18)

Compound 18 was prepared analogously to compound 17 (Example 17), with a UV/vis absorption max of $\lambda_{MeOH}$=786 nm, $\lambda_{PBS}$=779 nm, and emission at 805 nm.

Example 19

Preparation of Sodium 2-((E)-2-((E)-2-(3-Butoxy-2,4,6-trifluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

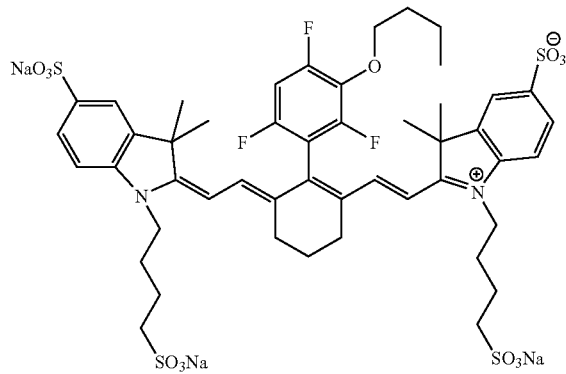

Sodium 2-((E)-2-((E)-2-(3-Butoxy-2,4,6-trifluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (19)

Compound 19 was prepared analogously to compound 17 (Example 17), with a UV/vis absorption max $\lambda_{MeOH}$=789 nm, $\lambda_{PBS}$=782 nm, and emission at 806 nm. $\epsilon_{MeOH}$=300,000; $\epsilon_{PBS}$=240,000.

Example 20

Preparation of Sodium 2-((E)-2-((E)-2-(4-Butoxy-2,3,5,6-tetrafluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

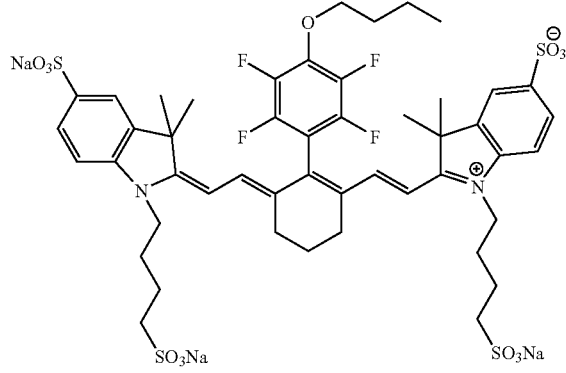

Sodium 2-((E)-2-((E)-2-(4-Butoxy-2,3,5,6-tetrafluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (20)

Compound 20 was is prepared analogously to compound 17 (Example 17), UV/vis absorption max $\lambda_{MeOH}$=790 nm, $\lambda_{PBS}$=786 nm, emission at 805 nm.

Example 21

Preparation of Bioconjugates of Strepavidin with Compound 10

Compound 11 was reconstituted in DMF to 1 mg/ml. Streptavidin was reconstituted typically at 10 mg/ml in PBS buffer at pH 8.5. The dyes were added (at various molar ratios) to the streptavidin samples and allowed to incubate for 2 hours at room temperature in the dark. The conjugates were extensively dialyzed against PBS buffer to remove the unconjugated free dye. The ratio of moles of dye per mole of protein in the conjugate was calculated as described below:

$$D/P = \left[\frac{A_{680}}{\varepsilon_{Dye}}\right] \div \left[\frac{A_{280} - (0.09 \times A_{680})}{\varepsilon_{Streptavidin}}\right]$$

In which:
$\epsilon_{dye}$=239,000 M$^{-1}$cm$^{-1}$
$\epsilon_{streptavidin}$=175,000 M$^{-1}$cm$^{-1}$
0.09 is the correction factor for the 680 dye absorption at 280 nm Example 22

Preparation of Bioconjugates of GAM Antibody with Compound 8

Compound 9 was reconstituted in DMF to 1 mg/ml. Goat anti-mouse (GAM) IgG (H+L) were reconstituted typically at 1 mg/ml in PBS buffer pH 8.5. The dyes were added (at various molar ratios) to the GAM antibody samples and allowed to incubate for 2 hours at room temperature in the dark. The conjugates were extensively dialyzed against PBS buffer to remove the unconjugated free dye. The dye to protein ratios were calculated as described above.

Example 23

Dot Blot Immunoassay Comparison of Total Fluorescence of Streptavidin Bioconjugate of Compound 10 with Commercially Available Streptavidin Bioconjugates of IRDye® 680 and Alexa 680 Dye Nitrocellulose membrane was previously coated with different amounts of biotinylated anti-rabbit IgG. The membrane was blocked with LI-COR Odyssey® Blocking Buffer for 30 min, followed by incubation for 30 min with bioconjugates of compound 10 and streptavidin at different D/P ratios. The membrane was washed vigorously with 1×PBS and 1×PBS-T. The membranes were scanned on a LI-COR Odyssey® Infrared Imager.

The streptavidin conjugates of compound 10 in these tests perform comparably to the best commercial streptavidin conjugates in this wavelength range. The LOD difference between 3.0 and 6.1 pg is a single spot in the dilution series, comparable to experimental variation. The fluorescence intensities of the bands of the compound 10 conjugates are comparable to or better than those of the commercial conjugates. Fluorescence background due to non-specific binding of the conjugates to the membrane is also low for all the conjugates tested.

TABLE 2

Dot Blot Immunoassay Comparison of Total Fluorescence of Streptavidin Bioconjugate of Compound 10 with Commercially Available Streptavidin Bioconjugates of IRDye ® 680 and Alexa 680 Dye

|  | Limit of Detection (LOD) (pg) | | Sample Fluorescence Intensity (K Counts) (Std Dev) | | Bkgd Intensity (Counts) (Std Dev) | |
| --- | --- | --- | --- | --- | --- | --- |
|  | Test 1 | Test 2 | Test 1 | Test 2 | Test 1 | Test 2 |
| D/P = 1.6 | 3.0/6.1 | 3.0 | 26.9 (10.2) | 26.8 (3.0) | 663.0 (52.3) | 545.0 (36.8) |
| D/P = 2.2 | 3.0 | 3.0 | 34.8 (2.1) | 37.5 (3.6) | 657.3 (29.7) | 606.3 (47.4) |
| D/P = 2.9 | 3.0 | 3.0 | 53.9 (7.0) | 41.4 (3.5) | 959.3 (110.3) | 773.7 (37.5) |
| Alexa680-Streptavidin | 3.0 | 3.0 | 49.4 (0) | 45.5 (2.4) | 866.7 (24.0) | 725.0 (102.5) |
| IRDye ® 680-Streptavidin | 6.1 | 6.1 | 20.3 (4.7) | 17.0 (0.2) | 462.0 (5.7) | 493.7 (40.3) |

The signal intensities are expressed in arbitrary fluorescence units ("Counts"), with the sample values divided by 1000 for convenience ("K Counts") after subtraction of background. In general, protein detection and quantitation are enhanced by increased fluorescence intensity and by low fluorescence background.

Example 24

ICW Comparison of Background Fluorescence of GAM Antibody Bioconjugate of Compound 8 with Commercially Available GAM Antibody Bioconjugates of IRDye® 680 Dye The GAM bioconjugate with compound 8 was evaluated by a cell-based immunohistochemical assay ("In-Cell Western" or ICW) and compared with LI-COR IRDye® 680 GAM bioconjugate, LI-COR Part No. 926-32220. A431 cells, ATCC Part No. CRL-1555, were seeded in a 96 well plate and incubated at 37° C. for 48 hours. Cells were then fixed with 37% formaldehyde and permeabilized with PBS+0.1% Triton® X-100. After permeabilization, cells were blocked with Odyssey® Blocking Buffer.

LI-COR IRDye 680-GAM antibody and compound 8-GAM antibody bioconjugates were both diluted in Odyssey® Blocking Buffer+0.2% Tween® 20 and added to the plate at a final concentration of 2 µg/ml, 12 wells per sample. Samples were incubated with gentle shaking at room temperature for 1 hour. The plate was washed three times with PBS+0.2% Tween® 20 and scanned on a LI-COR Odyssey® Infrared Imager, using the Microplate 2 preset. The average integrated intensity was calculated for each sample and the compound 8-GAM antibody was compared to LI-COR IRDye® 680-GAM antibody. The results are indicated in Tables 3 and 4 below.

The low fluorescence background for biological materials in the NIR enables experiments in live or fixed cells in microplates. An important example is the "In Cell Western" (ICW) technique, an immunohistochemical detection of celluar proteins in fixed cells. In such systems it is critical that the dye-labeled antibody used for detection maintains the very low fluorescence background of the original cellular environment. Thus the dye molecules attached to the detection antibody must have very low non-specific binding to other cellular proteins, to membranes, etc., or the labeled antibody will stick to those features and ruin the experiment. Antibodies labeled with IRDye® 680 or with Alexa Fluor° 680 maintain very low non-specific binding to cells. The data of Table 3 demonstrate that while the GAM antibody labeled with compound 8 gives somewhat higher background in this test than the two standards, it still has very low non-specific background. This dye can be used to produce labeled antibodies suitable for ICW and other cell-based (in vivo) applications.

TABLE 3

ICW Comparison of Total Fluorescence of GAM Antibody Conjugates of Compound 8 with Commercially Available GAM Antibody Conjugates of IRDye ® 680 and Alexa Fluor ® 680

| Sample | Antibody | Av. Intensity of Neg. Control Wells | % Control |
| --- | --- | --- | --- |
| 1 | IRDye ® 680-GAM | 4.07 | Control |
| 2 | Compound 8-GAM | 5.24 | 129 |
| 3 | Alexa Fluor ® 680-GAM | 4.35 | 107 |

Example 25

Western Blot Comparison of Total Fluorescence of GAM Antibody Bioconjugate of Compound 8 with Commercially Available GAM Antibody Bioconjugates of IRDye® 680

Jurkat lysate was run (5 µg to 78 ng) by SDS PAGE and transferred to nitrocellulose. Blots were blocked with Odyssey® Blocking Buffer+0.2% Tween®-20 (OBBT). Blots were probed with either monoclonal anti-actin (Neomarkers MS-1295-P1) or monoclonal anti-tubulin (Sigma T7816) diluted in OBBT. Blots were then detected with one of the following secondary antibodies diluted in OBBT to a final concentration of 0.1 µg/ml: GAM-compound 8 D/P=1.6 or LI-COR GAM 680 (see FIG. 1C-D).

The data in Table 4 and FIG. 1A-B demonstrate the excellent properties imparted by one of the instant dyes (compound 8) for Western blotting applications. Antibodies labeled with IRDye® 680 perform very well and serve as a "control" to represent the level of the current art. Antibodies labeled with compound 8 have significantly higher fluorescence intensity compared to the control, greater than 2-fold higher. Most fluorescent dye labeled biomolecules show a tendency to stick non-specifically, for example to the membranes used in a Western blot. As the fluorescence background data in FIG. 1 and Table 4 show, both IRDye® 680 and compound 8 (FIG. 1A-B) can be used to produce labeled antibodies with very low non-specific binding to the membrane.

TABLE 4

Western Blot Comparison of Total Fluorescence of GAM Antibody Bioconjugate of Compound 8 with Commercially Available GAM Antibody Bioconjugates of IRDye ® 680

| Sample | Blots | Sample Fluorescence Intensity (K Counts) | Bkgd Intensity (Counts) | Sample Mean Intensity | Sample Std Dev | Sample % Intensity of Control | Bkgd % of Control |
|---|---|---|---|---|---|---|---|
| Anti-Tubulin IRDye ® 680 GAM | 1 | 82.7 | 233 | 74.21 | 12.06 | control | control |
| | 2 | 65.7 | 243 | | | | |
| Anti-Tubulin GAM-Compound 8 | 3 | 171.2 | 262 | 191.85 | 29.26 | 259 | 108 |
| | 4 | 212.5 | 250 | | | | |
| Anti-Actin IRDye ® 680 GAM | 7 | 18.2 | 246 | 17.24 | 1.37 | control | control |
| | 8 | 16.3 | 255 | | | | |
| Anti-Actin GAM-Compound 8 | 9 | 42.6 | 274 | 39.89 | 3.79 | 231 | 110 |
| | 10 | 37.2 | 275 | | | | |

Example 26

Western Blot Comparison of Total Fluorescence of Streptavidin Conjugate to Compound 8 with Commercially Available Conjugates of IRDye® 680 Dye to Streptavidin Jurkat lysate was run on gels (5 μg to 78 ng). Blots were probed with ms anti-actin (Thermo No. MS-1295P) diluted 1:1000 in Odyssey® Blocking Buffer+0.2% Tween® 20 followed by Biotin-SP GAM (Jackson No. 115-065-166) diluted 1:20,000 in Odyssey® Blocker+0.2% Tween® 20. Blots were then detected with various 680 streptavidin bioconjugates in Odyssey® Blocking Buffer+0.2% Tween® 20 (see FIG. 2D).

Figure 2A:
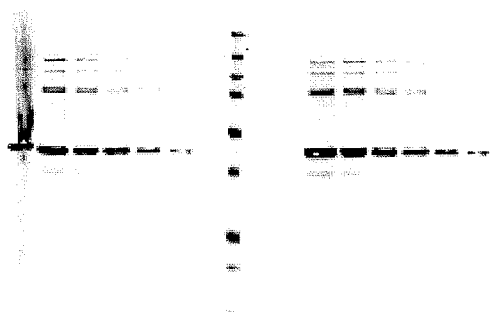
FIGS. 2A-D illustrate a Western blot total fluorescence comparison between a streptavidin conjugate of inventive dye 8 (Panels A-C) and a commercially available IRDye® 680 streptavidin conjugate ("LI-COR Streptavidin 680") (Panel D).
Figure 2B:
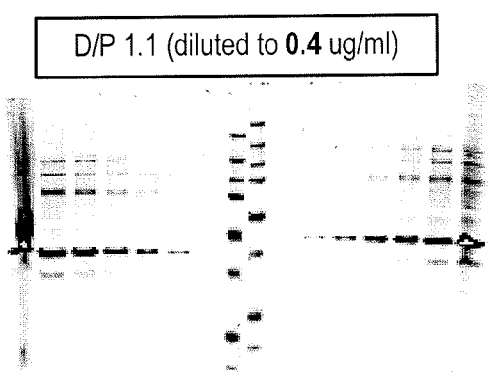
Figure 2C:
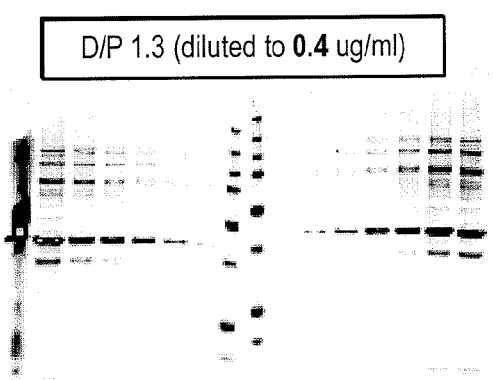
Figure 2D:
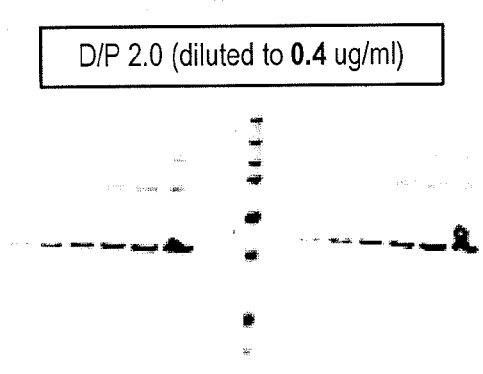

The streptavidin conjugates of one of the instant dyes (compound 8) also compare favorably with a commercial streptavidin conjugate in this example. In FIG. 2A-C the most dilute actin band can be clearly seen in each blot detected with compound 8 conjugate. The total fluorescence intensity for all the actin bands in each blot are summarized in Table 5, along with representative background areas of the membrane. The fluorescence intensities for the compound 8 conjugates are 2-3 times higher than the control, while fluorescence background is only slightly higher.

TABLE 5

Western Blot Comparison of Total Fluorescence of Streptavidin Conjugate to Compound 8 with Commercially Available Conjugates of IRDye ® 680 Dye to Streptavidin.

| Sample | Blots | Sample Fluorescence Intensity (K Counts) | Bkgd Intensity (Counts) | Sample Mean Intensity | Sample Std Dev | Sample % Intensity of Control | Bkgd % of Control |
|---|---|---|---|---|---|---|---|
| IRDye ® 680 Streptavidin (0.4 μg/ml) | 1 | 15.7 | 302 | 18.6 | 4.0 | control | control |
| | 2 | 21.4 | 293 | | | | |
| SA-Compound 8 D/P 1.1 (0.4 μg/ml) | 3 | 46.0 | 333 | 50.9 | 7.0 | 274 | 114 |
| | 4 | 55.8 | 348 | | | | |
| SA-Compound 8 D/P 1.3 (0.4 μg/ml) | 5 | 51.3 | 348 | 41.5 | 13.9 | 224 | 117 |
| | 6 | 31.7 | 350 | | | | |
| SA-Compound 8 D/P 2.0 (0.4 μg/ml) | 7 | 79.4 | 411 | 56.8 | 32.0 | 306 | 130 |
| | 8 | 34.1 | 364 | | | | |

Example 27

Preparation of Sodium 2-((1E,3Z,5E)-5-(1,1-Dimethyl-6,8-disulfonato-3-(3-sulfonatopropyl)-1H-benzo[e]indol-2(3H)-ylidene)-3-(3-(5-(2-(2,5-dioxo-2,5-dihydro-1H-pyrrol-1-yl)ethylamino)-5-oxopentyl)phenyl)penta-1,3-dienyl)-1,1-dimethyl-3-(3-sulfonatopropyl)-1H-benzo[e]indolium-6,8-disulfonate

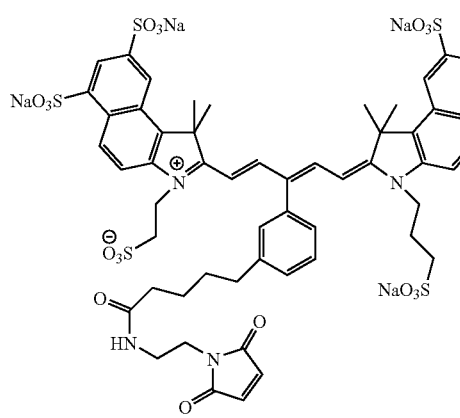

Sodium 2-((1E,3Z,5E)-5-(1,1-Dimethyl-6,8-disulfonato-3-(3-sulfonatopropyl)-1H-benzo[e]indol-2(3H)-ylidene)-3-(3-(5-(2-(2,5-dioxo-2,5-dihydro4H-pyrrol-1-yl)ethylamino)-5-oxopentyl)phenyl)penta-1,3-dienyl)-1,1-dimethyl-3-(3-sulfonatopropyl)-1H-benzo[e]indolium-6,8-disulfonate (21)

Compound 9 (0.18 mmol) is dissolved in 20 mL of dry DMSO and stirred at room temperature under dry nitrogen. Next, 2-maleimidio ethyl amine (93.2 mg, 0.37 mmol) is added to the stirred solution, followed by di-isopropyl ethyl amine (DIPEA) (95 mg, 0.55 mmol). The stirring is continued for 45 min. DMF (20 mL) is added to the reaction, and stirring continued until thorough mixing is achieved. The solution is then poured slowly into 400 mL of stirred diethyl ether to precipitate the product. The ether suspension is stirred for an additional 5 min, then allowed to stand for 1 hr. The ether is decanted and an additional 20 mL of DMF is added to redissolve the solid. The DMF solution is then precipitated into a second 400 mL portion of stirred ether. The crude product 21 is collected by filtration. Optionally, further purification can be performed, for example, by HPLC, column chromatography, or recrystallization.

Example 28

Preparation of Sodium 2-((1E,3Z,5E)-5-(1,1-Dimethyl-6,8-disulfonato-3-(4-sulfonatobutyl)-1H-benzo[e]indol-2(3H)-ylidene)-3-(3-(3-(2-(2,5-dioxo-2,5-dihydro-1H-pyrrol-1-yl)ethylamino)-3-oxopropyl)phenyl)penta-1,3-dienyl)-1,1-dimethyl-3-(4-sulfonatobutyl)-1H-benzo[e]indolium-6,8-disulfonate

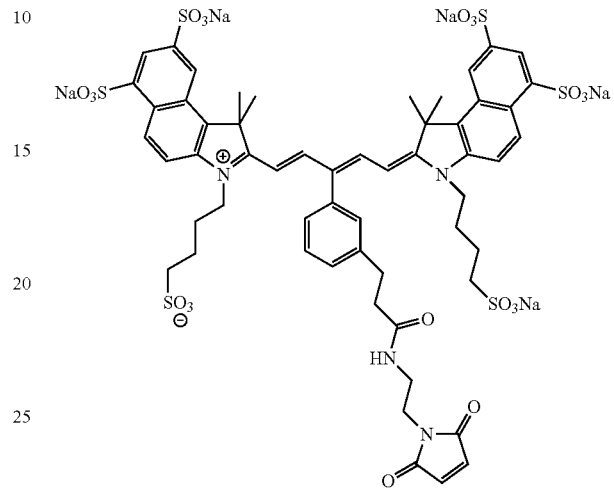

Sodium 2-((1E,3Z,5E)-5-(1,1-Dimethyl-6,8-disulfonato-3-(4-sulfonatobutyl)-1H-benzo[e]indol-2(3H)-ylidene)-3-(3-(3-(2-(2,5-dioxo-2,5-dihydro-1H-pyrrol-1-yl)ethylamino)-3-oxopropyl)phenyl)penta-1,3-dienyl)-1,1-dimethyl-3-(4-sulfonatobutyl)-1H-benzo[e]indolium-6,8-disulfonate (22)

Compound 22 is prepared analogously to compound 21 (Example 27), except that compound 11 is used as a starting material.

Example 29

Preparation of Sodium 2-((1E,3Z,5E)-5-(3,3-Dimethyl-5-sulfonato-1-(3-sulfonatopropyl)indolin-2-ylidene)-3-(3-(5-(2-(2,5-dioxo-2,5-dihydro-1H-pyrrol-1-yl)ethylamino)-5-oxopentyl)phenyl)penta-1,3-dienyl)-3,3-dimethyl-1-(3-sulfonatopropyl)-3H-indolium-5-sulfonate

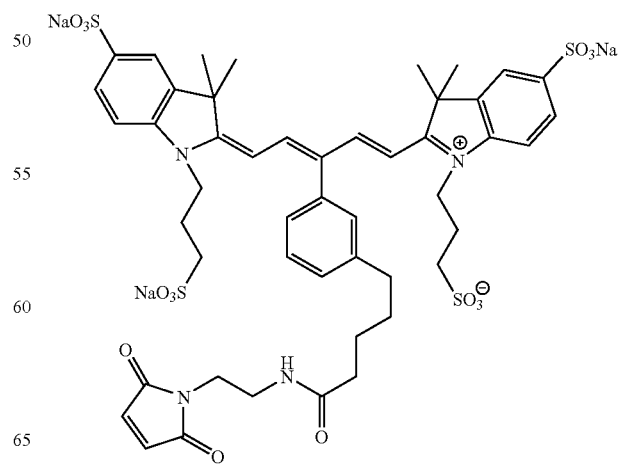

Sodium 2-((1E,3Z,5E)-5-(3,3-Dimethyl-5-sulfonato-1-(3-sulfonatopropyl)indolin-2-ylidene)-3-(3-(5-(2-(2,5-dioxo-2,5-dihydro-1H-pyrrol-1-yl)ethylamino)-5-oxopentyl)phenyl)penta-1,3-dienyl)-3,3-dimethyl-1-(3-sulfonatopropyl)-3H-indolium-5-sulfonate (23)

Compound 23 is prepared analogously to compound 21 (Example 27), except that compound 15 is used as a starting material.

Example 30

Preparation of Sodium 2-((E)-2-((E)-2-(3-Carboxyphenyl)-3-((E)-2-(3,3-dimethyl-5-sulfonato-1-(4-sulfonatobutyl)indolin-2-ylidene)ethylidene)cyclopent-1-enyl)vinyl)-3,3-dimethyl-1-(4-sulfonatobutyl)-3H-indolium-5-sulfonate

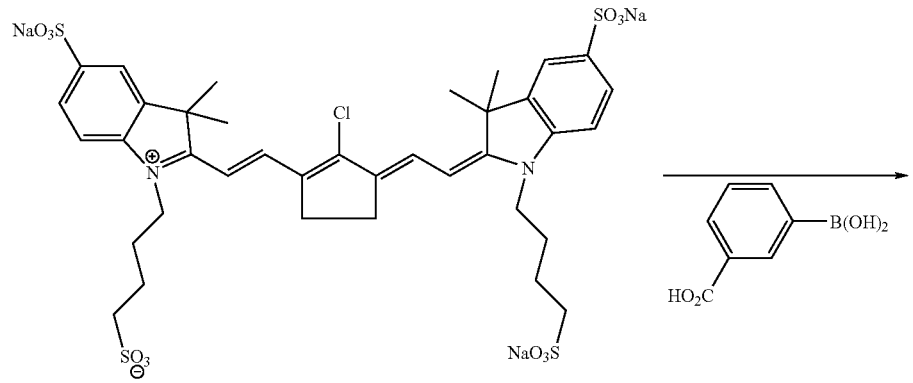

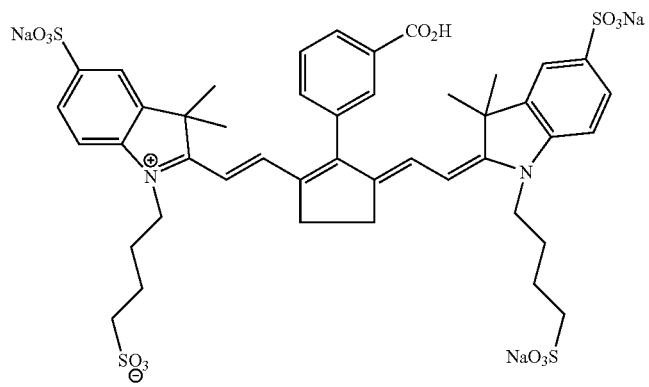

Preparation of Sodium 2-((E)-2-((E)-2-(3-Carboxyphenyl)-3-((E)-2-(3,3-dimethyl-5-sulfonato-1-(4-sulfonatobutyl)indolin-2-ylidene)ethylidene)cyclopent-1-enyl)vinyl)-3,3-dimethyl-1-(4-sulfonatobutyl)-3H-indolium-5-sulfonate (24)

Compound 24 was prepared analogously to compound 17, except with the cyclopentyl chloro dye precursor and 3-boronobenzoic acid as starting materials. A skilled person will appreciate that the boronic acid intermediates used here are versatile and can be modified by custom synthesis to meet various design changes. The phenyl ring can be substituted with various types of substituents and substituent lengths. One custom synthesis manufacture is Combi-Blocks, Inc. of San Diego, Calif.

Example 31

Preparation of Sodium 2-((E)-2-((E)-2-(3-(3-Carboxypropyl)phenyl)-3-((E)-2-(3,3-dimethyl-5-sulfonato-1-(4-sulfonatobutyl)indolin-2-ylidene)ethylidene)cyclopent-1-enyl)vinyl)-3,3-dimethyl-1-(4-sulfonatobutyl)-3H-indolium-5-sulfonate

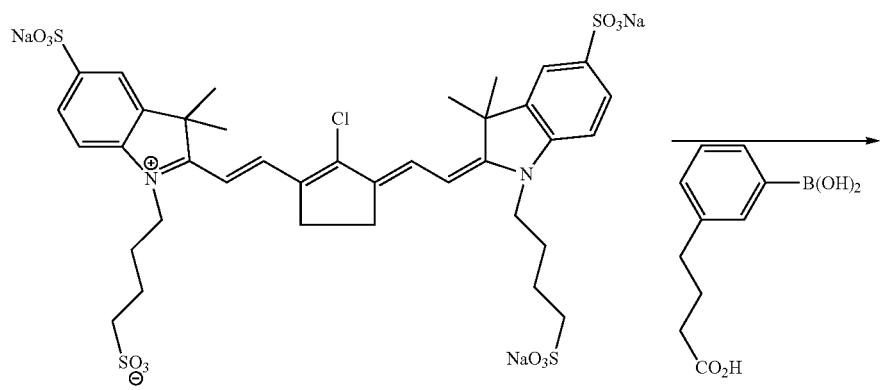

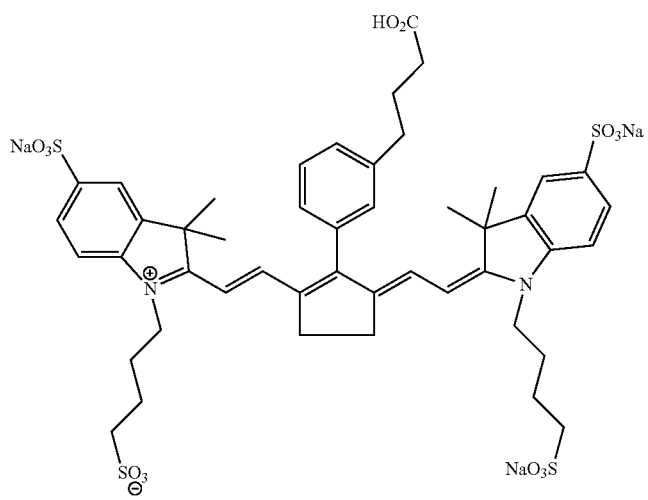

Sodium 2-((E)-2-((E)-2-(3-(3-Carboxypropyl)phenyl)-3-((E)-2-(3,3-dimethyl-5-sulfonato-1-(4-sulfonatobutyl)indolin-2-ylidene)ethylidene)cyclopent-1-enyl)vinyl)-3,3-dimethyl-1-(4-sulfonatobutyl)-3H-indolium-5-sulfonate (25)

Compound 25 is prepared analogously to compound 24, except with 4-(3-boronophenyl)butanoic acid as a starting material.

Example 31B

Preparation of Sodium 2-((E)-2-((E)-2-(3-(3-Carboxybutyl)phenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

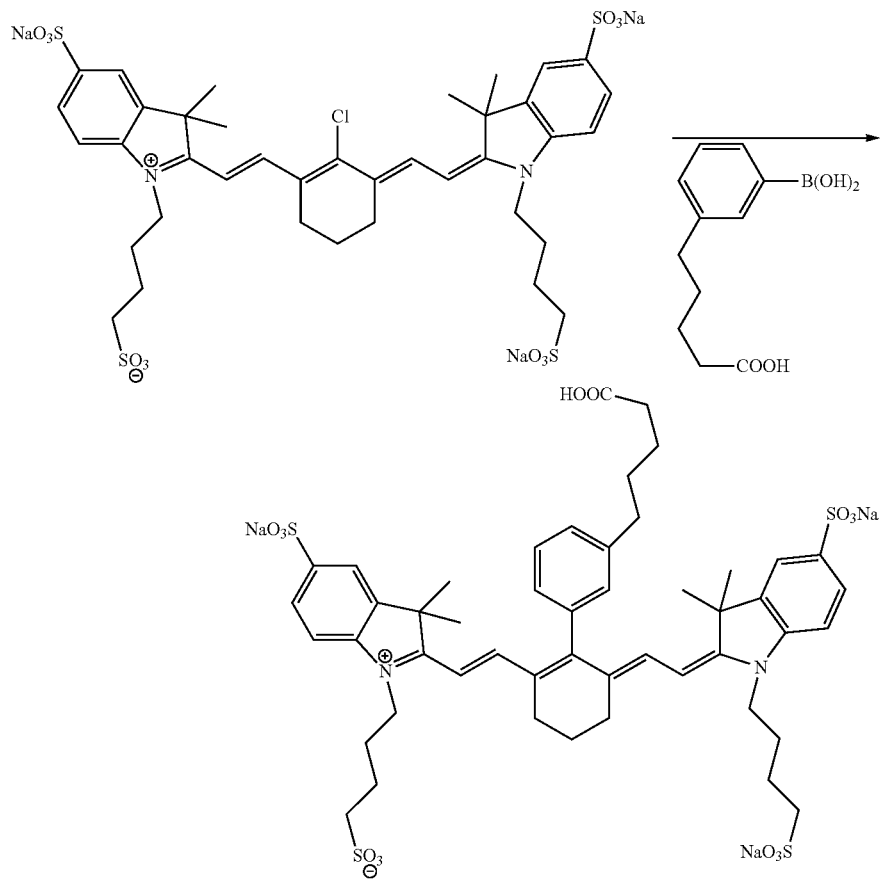

Sodium 2-((E)-2-((E)-2-(3-(3-Carboxybutyl)phenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (26)

Compound 26 was prepared analogously to compound 24, except with 5-(3-boronophenyl)pentanoic acid as a starting material. UV: $\lambda_{PBS}$=756 nm, $\epsilon$=260,000; $\lambda_{MeOH}$=766 nm, $\epsilon$=330,000. Emission: $\lambda_{MeOH}$=776 nm.

Example 32

Preparation of Sodium 2-((1E,3Z,5E,7E)-4-(3-Carboxyphenyl)-7-(3,3-dimethyl-5-sulfonato-1-(4-sulfonatobutyl)indolin-2-ylidene)hepta-1,3,5-trienyl)-3,3-dimethyl-1-(4-sulfonatobutyl)-3H-indolium-5-sulfonate

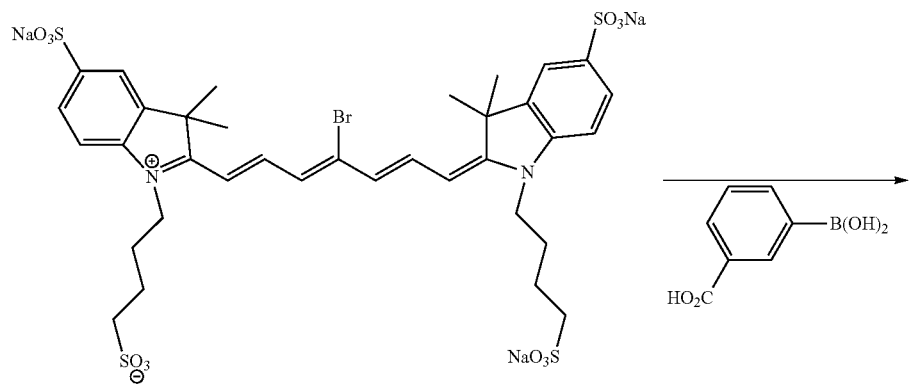

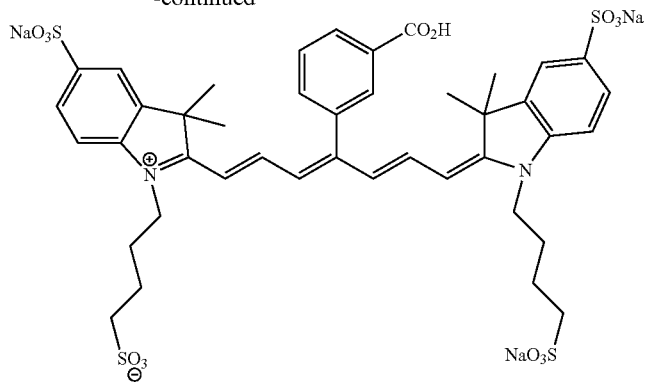

Sodium 2-((1E,3Z,5E,7E)-4-(3-Carboxyphenyl)-7-(3,3-dimethyl-5-sulfonato-1-(4-sulfonatobutyl)indolin-2-ylidene)hepta-1,3,5-trienyl)-3,3-dimethyl-1-(4-sulfonatobutyl)-3H-indolium-5-sulfonate (27)

Compound 27 is prepared analogously to compound 24, except with the chloro dye precursor and m-carboxyphenyl boronic acid as a starting material. Alternatively, the bromo substituent can be replaced by another halo such as iodo or chloro, but bromo is preferred.

Example 33

Preparation of Sodium 2-((E)-2-((E)-2-(3-(3-Carboxypropyl)phenyl)-3-((E)-2-(3,3-dimethyl-5-sulfonato-1-(4-sulfonatobutyl)indolin-2-ylidene)ethylidene)cyclopent-1-enyl)vinyl)-3,3-dimethyl-1-(4-sulfonatobutyl)-3H-indolium-5-sulfonate

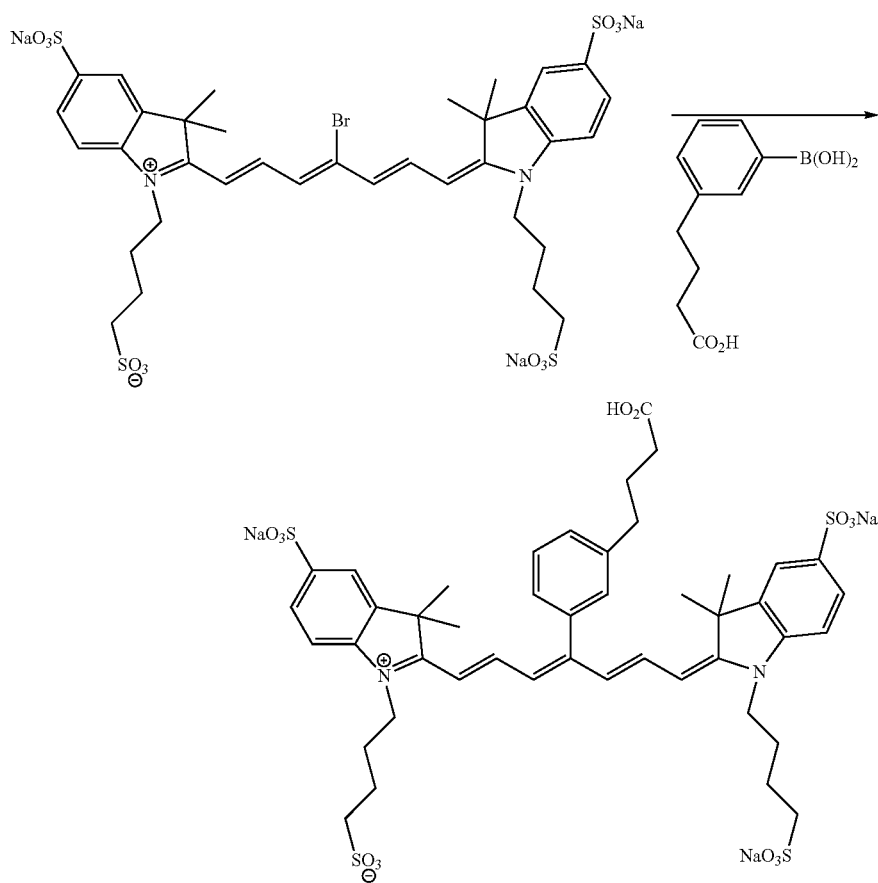

Sodium 2-((E)-2-((E)-2-(3-(3-Carboxypropyl)phenyl)-3-((E)-2-(3,3-dimethyl-5-sulfonato-1-(4-sulfonatobutyl)indolin-2-ylidene)ethylidene)cyclopent-1-enyl)vinyl)-3,3-dimethyl-1-(4-sulfonatobutyl)-3H-indolium-5-sulfonate (28)

Compound 28 is prepared analogously to compound 24, except with 4-(3-boronophenyl)butanoic acid as a starting material. Alternatively, the bromo substituent can be replaced by another halo such as iodo or chloro, but bromo is preferred.

Example 34

Preparation of Sodium 2-((E)-2-((E)-3-((E)-2-(3,3-Dimethyl-5-sulfonato-1-(4-sulfonatobutyl)indolin-2-ylidene)ethylidene)-2-(3-(4-hydroxybutoxy)phenyl)cyclohex-1-enyl)vinyl)-3,3-dimethyl-1-(4-sulfonatobutyl)-3H-indolium-5-sulfonate

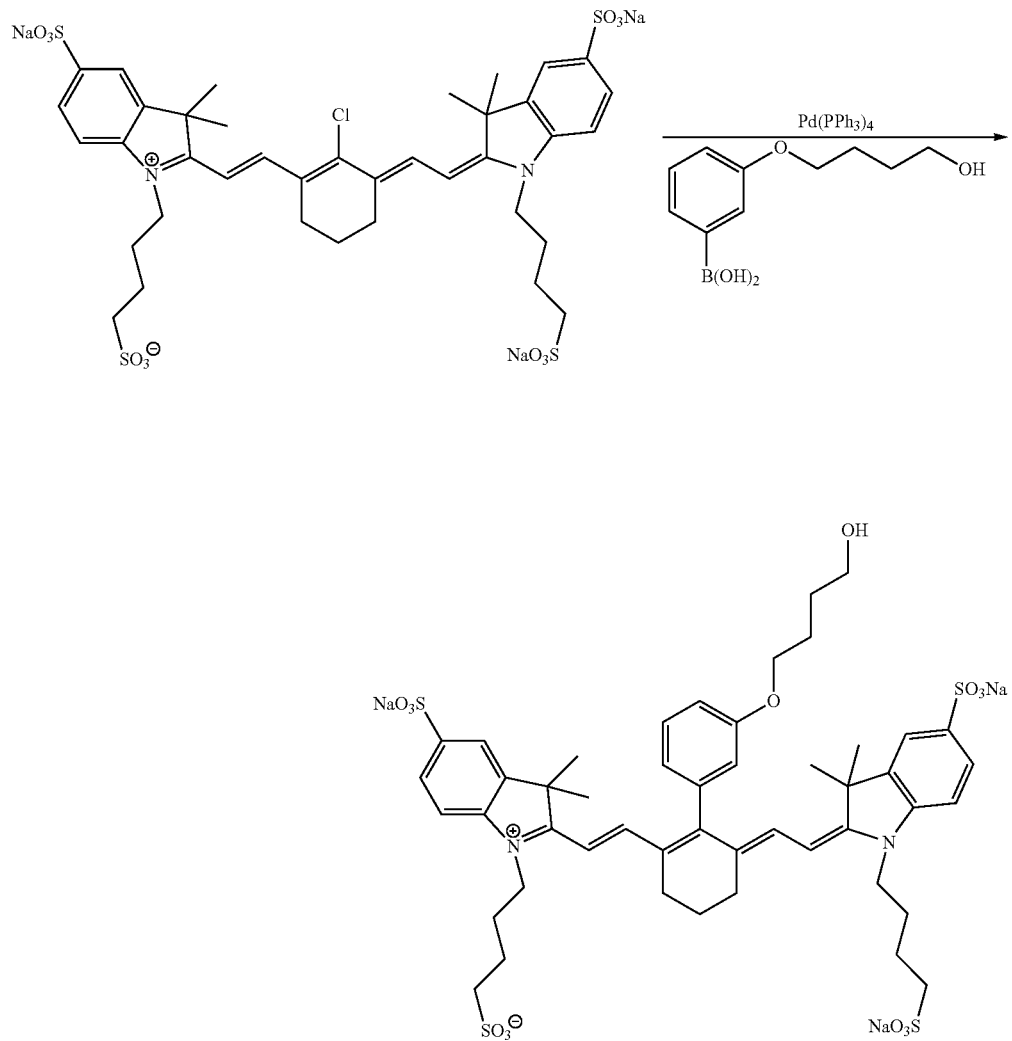

Sodium 2-((E)-2-((E)-3-((E)-2-(3,3-Dimethyl-5-sulfonato-1-(4-sulfonatobutyl)indolin-2-ylidene)ethylidene)-2-(3-(4-hydroxybutoxy)phenyl)cyclohex-1-enyl)vinyl)-3,3-dimethyl-1-(4-sulfonatobutyl)-3H-indolium-5-sulfonate (29)

Compound 29 is prepared by the same method as compound 17, except with 3-(4-hydroxybutoxy)phenylboronic acid as shown above.

Example 35

Preparation of Tetrabutylammonium 2-((E)-2-((E)-3-((E)-2-(3,3-Dimethyl-5-sulfonato-1-(4-sulfonatobutyl)indolin-2-ylidene)ethylidene)-2-(3-(4-hydroxybutoxy)phenyl)cyclohex-1-enyl)vinyl)-3,3-dimethyl-1-(4-sulfonatobutyl)-3H-indolium-5-sulfonate

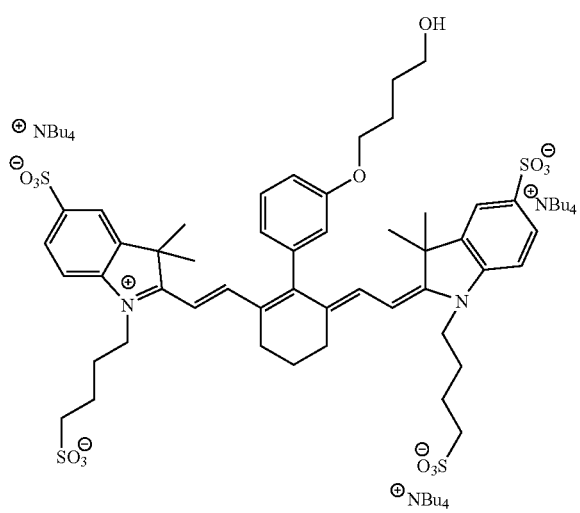

Tetrabutylammonium 2-((E)-2-((E)-3-((E)-2-(3,3-Dimethyl-5-sulfonato-1-(4-sulfonatobutyl)indolin-2-ylidene)ethylidene)-2-(3-(4-hydroxybutoxy)phenyl)cyclohex-1-enyl)vinyl)-3,3-dimethyl-1-(4-sulfonatobutyl)-3H-indolium-5-sulfonate (30)

Compound 30 is prepared by ion exchange of the sodium ions of compound 29. Ion exchange to salts such as tetralkylammonium and the like will improve the solubility of the dye in organic solvents suitable for DNA synthesis (e.g., acetonitrile). This can be done with chromatography as part of the purification process for the hydroxy dye, or as a separate ion exchange step. Commercial cationic ion exchange resins are widely available.

Example 36

Preparation of Tetrabutylammonium 2-((E)-2-((E)-2-(3-(4-(2-Cyanoethyl)(diisopropylamino)phosphinooxy)butoxy)phenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

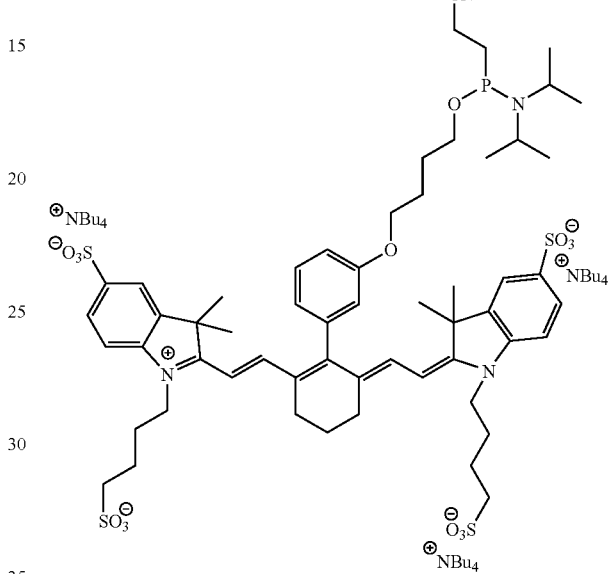

Tetrabutylammonium 2-((E)-2-((E)-2-(3-(4-((2-Cyanoethyl)(diisopropylamino)phosphinooxy)butoxy)phenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (31)

The general procedure described in U.S. Pat. No. 6,027,709 is used. Compound 30 (0.140 mmol) is dissolved in 10 ml of dry methylene chloride and stirred under argon at about 0° C. in an ice/salt bath for 30 minutes. A solution of bis(N,N-diisopropylamino)-cyanoethyl phosphine (2.13 ml., 0.15 M in methylene chloride) is added to the dye solution. Tetrazole (0.128 ml., 0.5 M) in acetonitrile is then added to the cooled solution. The cooling is removed after 20 minutes and the reaction is continued for an additional 1.5 hours at room temperature. The reaction mixture is quenched with 5% aqueous sodium bicarbonate solution, washed twice with water, and dried with sodium sulfate. The solvent is removed under vacuum. The crude product is taken up in 1.5 ml of methylene chloride, and the product 31 is obtained by precipitation into hexane.

Example 37

Preparation of Oligonucleotide Bioconjugate with Phosphoramide Linking Group

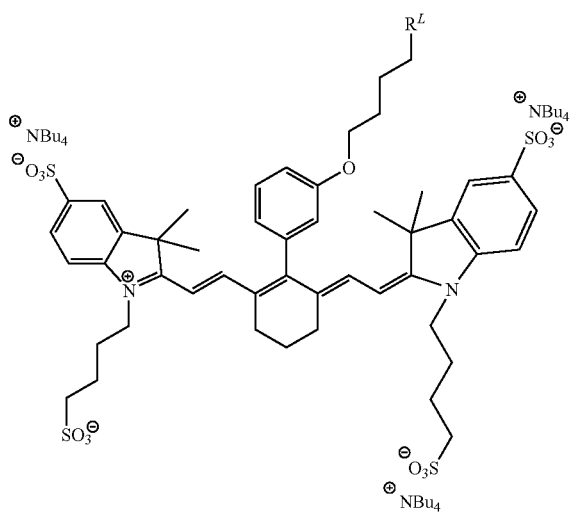

Oligonucleotide Bioconjugate with Phosphoramide Linking Group (32)

The general procedure described in U.S. Pat. No. 6,027,709 is used. The phosphoramidite of the fluorescent dye 32 can be used to label DNA molecules prepared in a DNA synthesis machine. The dye is attached to the 5' end of the protected, support-bonded oligonucleotide via standard phosphoramidite chemistry. Typical yields on a 200 nmol scale is expected to range from 50 to100 nmol before purification.

Each of the DNA oligonucleotides M13 fwd (–29), M13 rev, T7, T3 and SP6, is synthesized in the PerSeptive Biosystems Expedite 8909 DNA synthesis machine in accordance with standard reagents and the methodology taught by the manufacturer. The same apparatus then is used to attach the fluorescent label to the 5' end of each oligonucleotide by treatment with a 0.1 M solution of the dye phosphoramidite produced above in acetonitrile. For the attachment of the dye phosphoramidite, a three minute delay is inserted after the delivery of the dye in the tetrazole to the synthesis column to allow additional time for the coupling reaction. The 5'-fluorescent labeled DNA oligonucleotide is produced following oxidation, cleavage, deprotection and purification by HPLC.

For HPLC purification of the labeled oligonucleotide, a C18 reverse-phase column having 5μ particles, 300 A pore size (Waters DeltaPak), 1.7 ml/min may be used. Solvent A is 4% acetonitrile in aqueous 0.1 M triethylammonium acetate, and Solvent B is an 80% acetonitrile in aqueous 0.1 M triethylammonium acetate. The gradient profile is 10 to 45% B over 35 minutes, 45 to 100% B over 15 minutes, 100 to 10% B in 10 minutes. One of skill in the art may modify or replace these conditions as necessary for purification of various dyes.

The labeled oligonucleotide bioconjugate 32 can be used, for example, as a primer in the Sanger method of DNA sequencing, as a tailed primer for genotyping, or as a hybridization probe.

Example 38

Preparation of Sodium 2-((1E,3Z,5E)-3-(2-(4-Carboxybutyl)phenyl)-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate

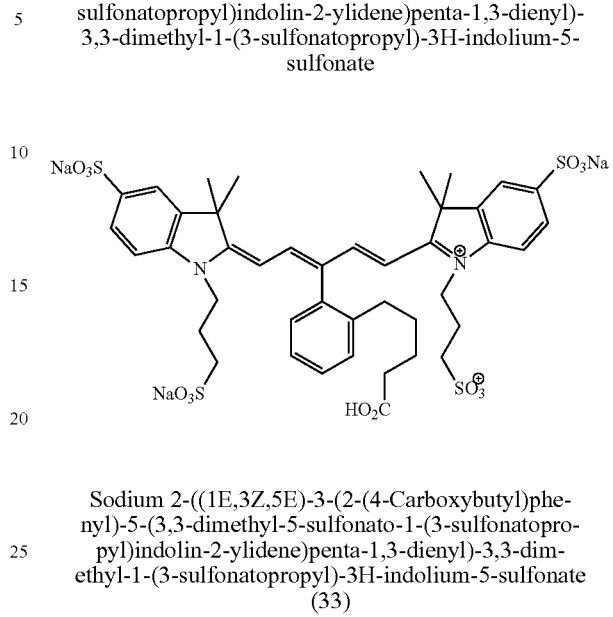

Sodium 2-((1E,3Z,5E)-3-(2-(4-Carboxybutyl)phenyl)-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate (33)

Compound 33 is prepared analogously to compound 8 (Example 8), except with 2-5-(2-boronophenyl)pentanoic acid as a starting material.

Example 39

Preparation of Sodium 2-((1E,3Z,5E)-5-(3,3-Dimethyl-5-sulfonato-1-(3-sulfonatopropyl)indolin-2-ylidene)-3-(2-(5-(2,5-dioxopyrrolidin-1-yloxy)-5-oxopentyl)phenyl)penta-1,3-dienyl)-3,3-dimethyl-1-(3-sulfonatopropyl)-3H-indolium-5-sulfonate

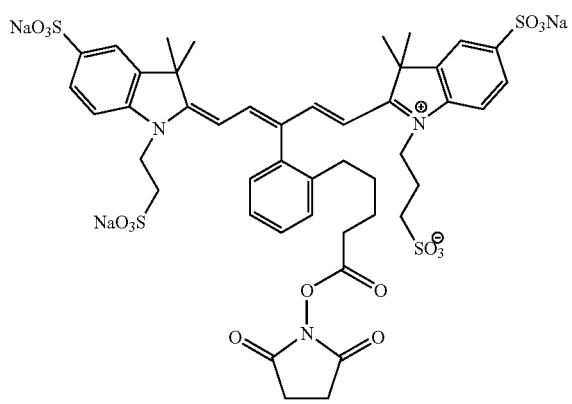

Sodium 2-((1E,3Z,5E)-5-(3,3-Dimethyl-5-sulfonato-1-(3-sulfonatopropyl)indolin-2-ylidene)-3-(2-(5-(2,5-dioxopyrrolidin-1-yloxy)-5-oxopentyl)phenyl)penta-1,3-dienyl)-3,3-dimethyl-1-(3-sulfonatopropyl)-3H-indolium-5-sulfonate (34)

Compound 34 is prepared analogously to compound 9 (Example 9), except that compound 33 is used as a starting material.

Example 40

Preparation of Sodium 2-((1E,3Z,5E)-3-(3-(3-Carboxypropoxy)-5-fluorophenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

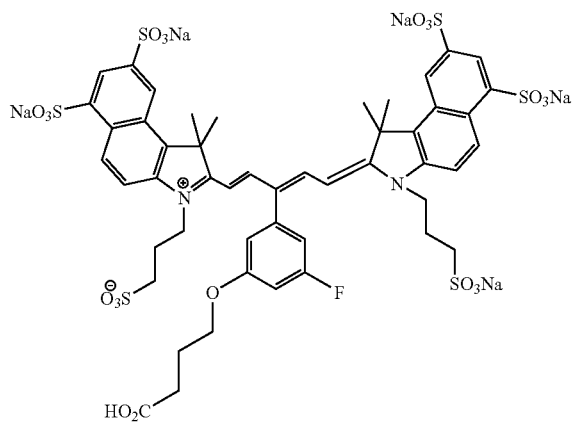

Sodium 2-((1E,3Z,5E)-3-(3-(3-Carboxypropoxy)-5-fluorophenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate (35)

Compound 35 is prepared analogously to compound 8 (Example 8), except that 4-(3-borono-5-fluorophenoxy)butanoic acid is used as a starting material.

Example 40B

Preparation of Sodium 2-((1E,3Z,5E)-(3-Carboxymethoxy-5-fluorophenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

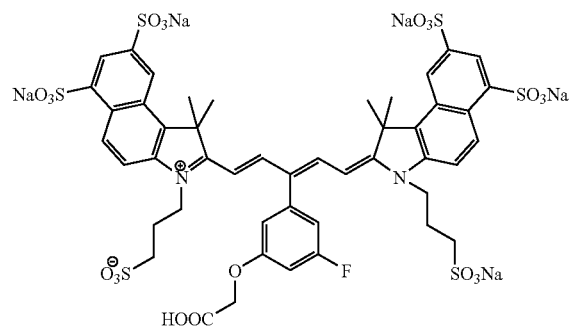

Sodium 2-((1E,3Z,5E)-3-(3-Carboxymethoxy-5-fluorophenyl)-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate (36)

Compound 36 was prepared analogously to compound 8 (Example 8), except that 2-(3-borono-5-fluorophenoxy)acetic acid is used as a starting material.

Example 41

Preparation of Sodium 2-((E)-2-((E)-2-(3-(3-Carboxypropoxy)-2,6-difluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

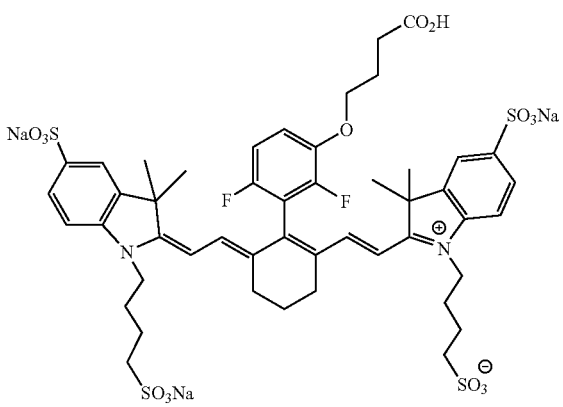

Sodium 2-((E)-2-((E)-2-(3-(3-Carboxypropoxy)-2,6-difluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate (37)

Compound 37 is prepared analogously to compound 17, except with 4-(3-borono-2,4-difluorophenoxy)butanoic acid as a starting material.

Example 42

Preparation of Sodium 2-((E)-2-((E)-2-(3-(3-Carboxypropoxy)-2,4,6-trifluorophenyl)-3-((E)-2-(3,3-dimethyl-5-sulfonato-1-(4-sulfonatobutyl)indolin-2-ylidene)ethylidene)cyclohex-1-enyl)vinyl)-3,3-dimethyl-1-(4-sulfonatobutyl)-3H-indolium-5-sulfonate

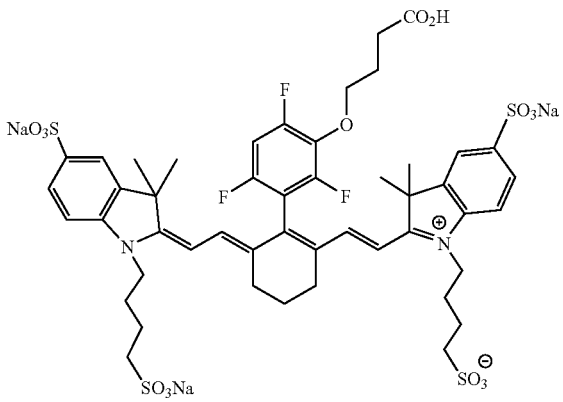

Sodium 2-((E)-2-((E)-2-(3-(3-Carboxypropoxy)-2,4,
6-trifluorophenyl)-3-((E)-2-(3,3-dimethyl-5-sul-
fonato-1-(4-sulfonatobutyl)indolin-2-ylidene)eth-
ylidene)cyclohex-1-enyl)vinyl)-3,3-dimethyl-1-(4-
sulfonatobutyl)-3H-indolium-5-sulfonate (38)

Compound 38 was prepared analogously to compound 17 (Example 17), except with 4-(3-borono-2,4,6-trifluorophenoxy)butanoic acid as a starting material.

Example 42B

Preparation of Sodium 2-((E)-2-((E)-2-(3-(4-Car-
boxybutyl)-2,4,6-trifluorophenyl)-3-((E)-2-(3,3-dim-
ethyl-5-sulfonato-1-(4-sulfonatobutyl)indolin-2-
ylidene)ethylidene)cyclohex-1-enyl)vinyl)-3,3-
dimethyl-1-(4-sulfonatobutyl)-3H-indolium-5-
sulfonate

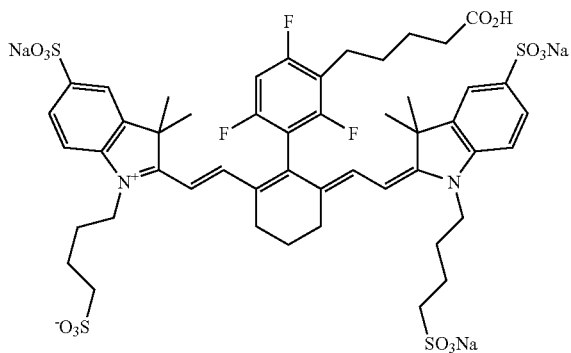

Sodium 2-((E)-2-((E)-2-(3-(4-Carboxybutyl)-2,4,6-
trifluorophenyl)-3-((E)-2-(3,3-dimethyl-5-sulfonato-
1-(4-sulfonatobutyl)indolin-2-ylidene)ethylidene)
cyclohex-1-enyl)vinyl)-3,3-dimethyl-1-(4-
sulfonatobutyl)-3H-indolium-5-sulfonate (39)

Compound 39 is prepared analogously to compound 17 (Example 17), except with 5-(3-borono-2,4,6-trifluorophenyl)pentanoic acid as a starting material.

Example 43

Preparation of Sodium 3-(2-((1E,3Z,5E)-5-(1,1-dim-
ethyl-3-(3-sulfonatopropyl)-1H-benzo[e]indol-2
(3H)-ylidene)-3-(3-(4-hydroxybutoxy)phenyl)penta-
1,3-dienyl)-1,1-dimethyl-1H-benzo[e]indolium-3-yl)
propane-1-sulfonate

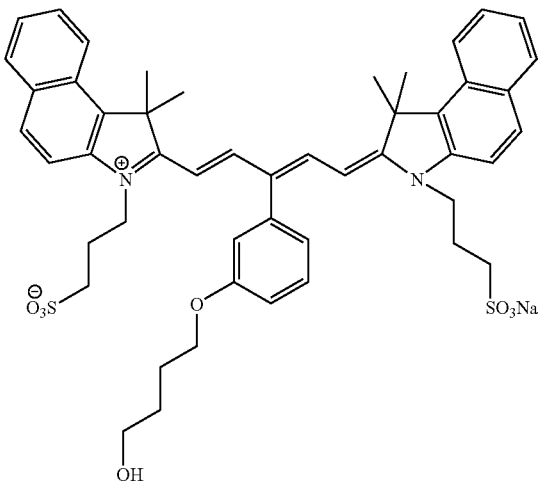

Sodium 3-(2-((1E,3Z,5E)-5-(1,1-dimethyl-3-(3-sul-
fonatopropyl)-1H-benzo[e]indol-2(3H)-ylidene)-3-
(3-(4-hydroxybutoxy)phenyl)penta-1,3-dienyl)-1,1-
dimethyl-1H-benzo[e]indolium-3-yl)propane-1-
sulfonate (40)

Compound 40 is prepared analogously to compounds 16 and 29, except with sodium 3-(2-((1E,3Z,5E)-3-bromo-5-(1,1-dimethyl-3-(3-sulfonatopropyl)-1H-benzo[e]indol-2(3H)-ylidene)penta-1,3-dienyl)-1,1-dimethyl-1H-benzo[e]indolium-3-yl)propane-1-sulfonate and 3-(4-hydroxybutoxy)phenylboronic acid as starting materials.

Example 44

Preparation of Tetrabutylammonium 3-(2-((1E,3Z,
5E)-5-(1,1-Dimethyl-3-(3-sulfonatopropyl)-1H-
benzo[e]indol-2(3H)-ylidene)-3-(3-(4-hydroxybu-
toxy)phenyl)penta-1,3-dienyl)-1,1-dimethyl-1H-
benzo[e]indolium-3-yl)propane-1-sulfonate

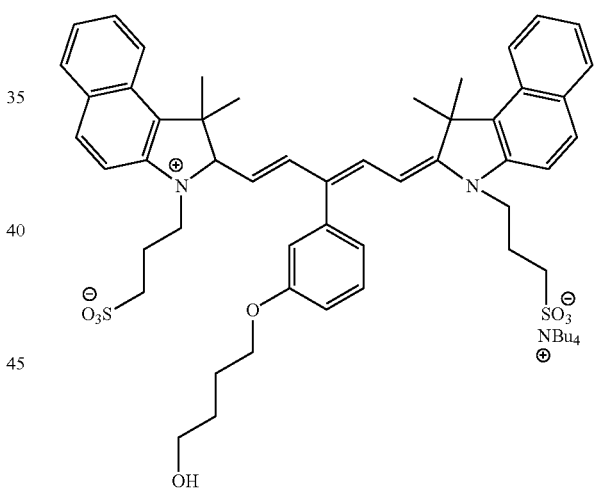

Tetrabutylammonium 3-(2-((1E,3Z,5E)-5-(1,1-Dim-
ethyl-3-(3-sulfonatopropyl)-1H-benzo[e]indol-2-
(3H)-ylidene)-3-(3-(4-hydroxybutoxy)phenyl)penta-
1,3-dienyl)-1,1-dimethyl-1H-benzo[e]indolium-3-yl)
propane-1-sulfonate (41)

Compound 41 is prepared analogously to compound 30.

Example 45

Preparation of Tetrabutylammonium 3-(2-((1E,3Z,5E)-3-(3-(4-((2-cyanoethyl)(diisopropylamino)phosphinooxy)butoxy)phenyl)-5-(1,1-dimethyl-3-(3-sulfonatopropyl)-1H-benzo[e]indol-2(3H)-ylidene)penta-1,3-dienyl)-1,1-dimethyl-1H-benzo[e]indolium-3-yl)propane-1-sulfonate

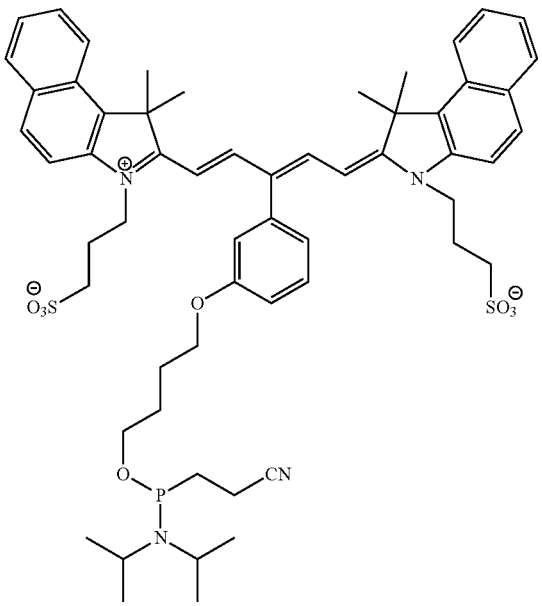

Tetrabutylammonium 3-(2-((1E,3Z,5E)-3-(3-(4-((2-cyanoethyl)(diisopropylamino)phosphinooxy)butoxy)phenyl)-5-(1,1-dimethyl-3-(3-sulfonatopropyl)-1H-benzo[e]indol-2(3H)-ylidene)penta-1,3-dienyl)-1,1-dimethyl-1H-benzo[e]indolium-3-yl)propane-1-sulfonate (42)

Compound 42 is prepared analogously to compound 31.

Example 46

Preparation of Oligonucleotide Bioconjugate II with Phosphoramide Linking Group

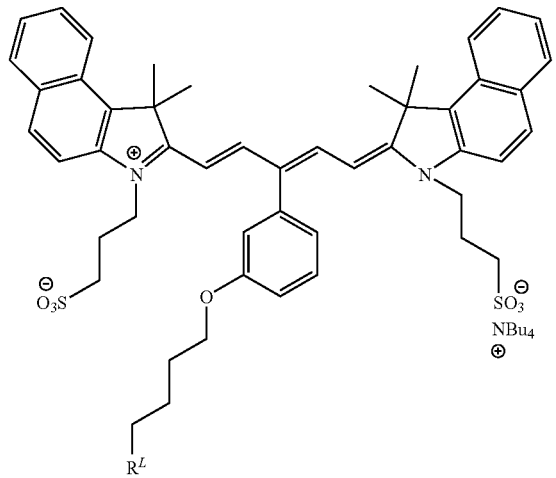

Oligonucleotide Bioconjugate II with Phosphoramide Linking Group (43)

Compound 43 is prepared and used analogously to compound 32.

Example 47

Preparation of Oligonucleotide Bioconjugate III with Phosphoramide Linking Group

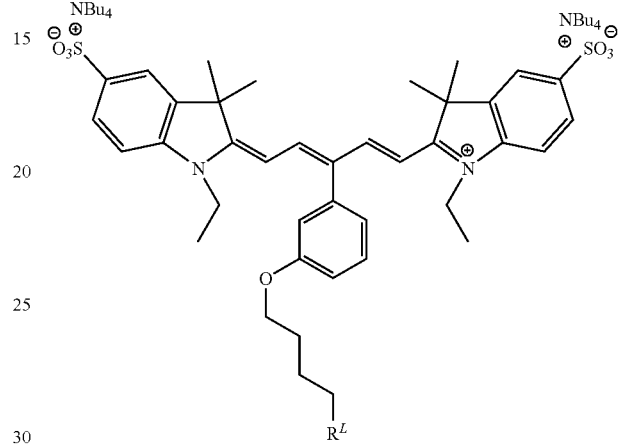

Oligonucleotide Bioconjugate III with Phosphoramide Linking Group (44)

Compound 44 and its precursors are prepared and used analogously to compounds 12, 13, and 29-32.

Example 48

Dye Brightness: Compound 8

Figure 3A:
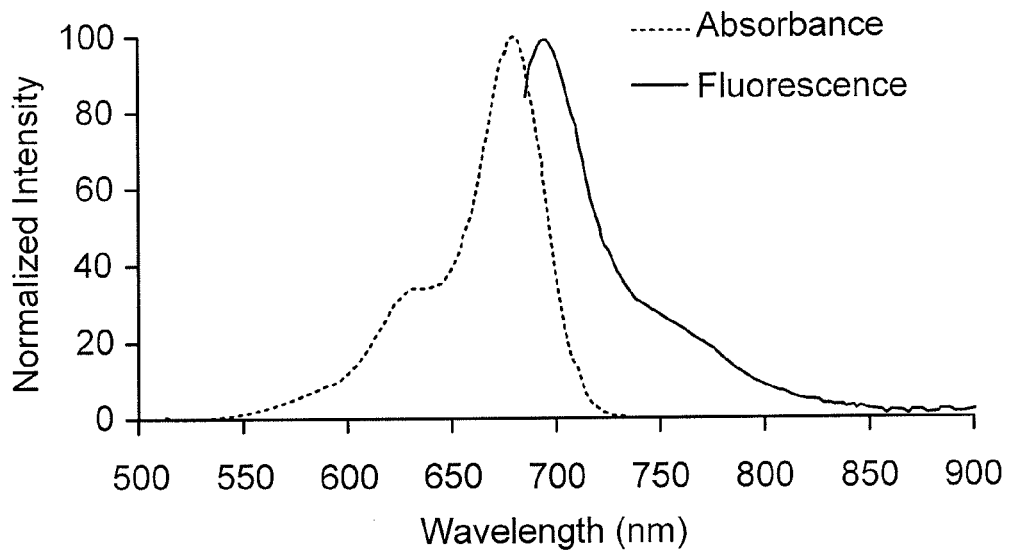
FIGS. 3A-B show the absorbance and emission spectra of compound 8 in methanol (680 nm) in Panel A; and in phosphate-buffered saline (PBS) solution (676 nm) in Panel B.
Figure 3B:
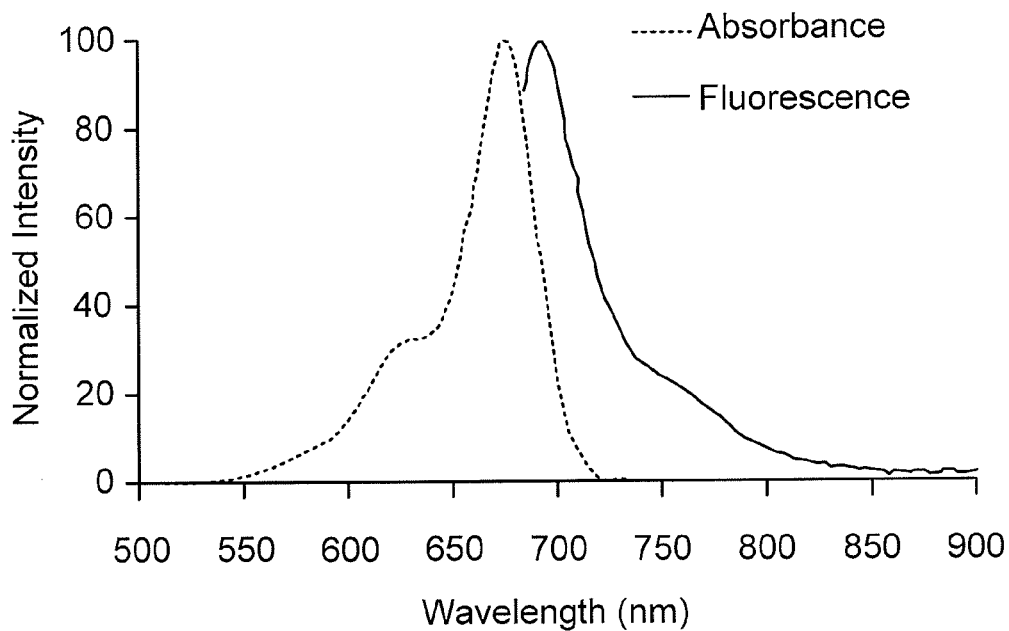
Figure 4:
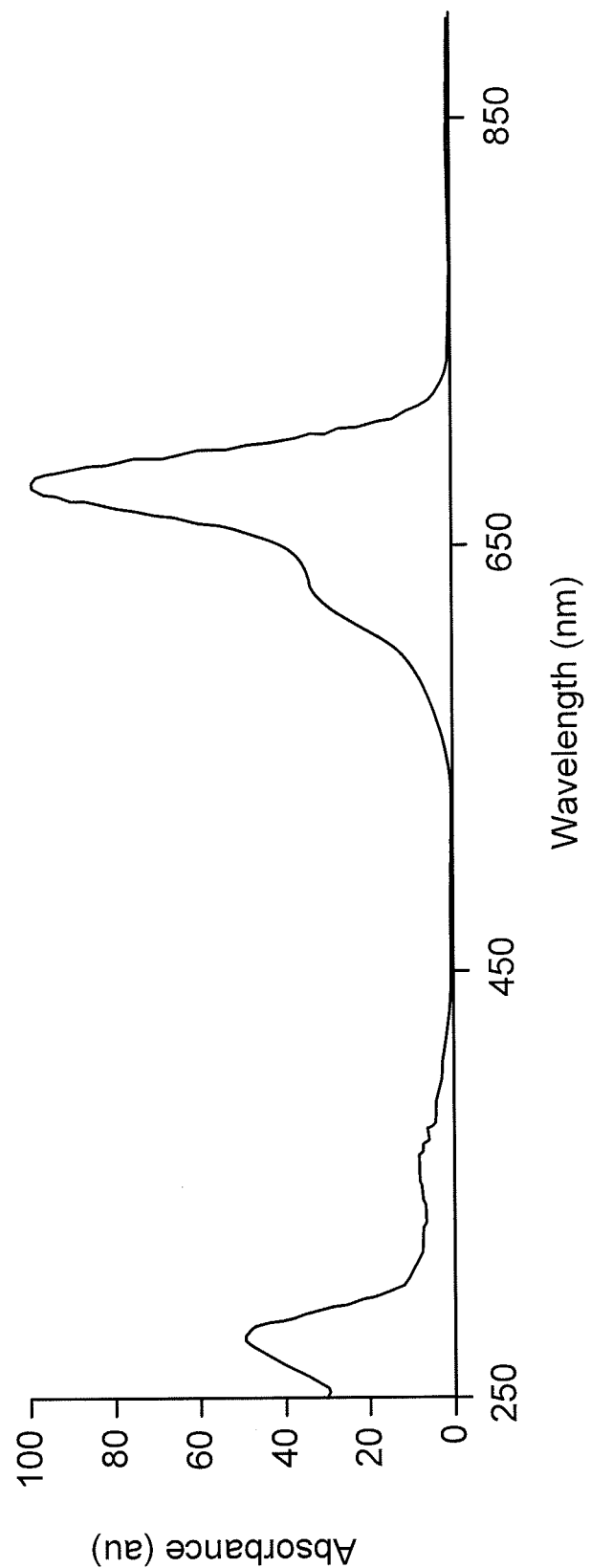
FIG. 4 shows the absorbance spectrum in 1:1 PBS:methanol of compound 8 conjugated to GAM antibody.
Figure 5:
FIG. 5 shows the absorbance spectrum in 1:1 PBS: methanol of compound 8 conjugated to lactalbumin.

The baseline fluorescence of compound 8 was determined. Fluorescence determinations were made at a fixed antibody concentration of 10 mg/mL in physiological buffer using dye-labeled goat anti-rabbit (GAR) conjugates prepared at LI-COR (FIGS. 3A-B and 4). A dye-labeled lactalbumin conjugate was also tested (FIG. 5).

The absorption maximum of compound 8 is at 676 nm in aqueous solution and at 693 nm in methanol. Compound 8 is a highly water-soluble dye optimized for use on the Odyssey Infrared Imager and the Aerius Automated Imager in the 700 nm channel.

Example 49

Comparison of Dye Brightness: Compound 8 and Alexa Fluor 680LT

A comparison of compound 8 with the commercially available dye Alexa Fluor 680 was conducted.

Figure 6:
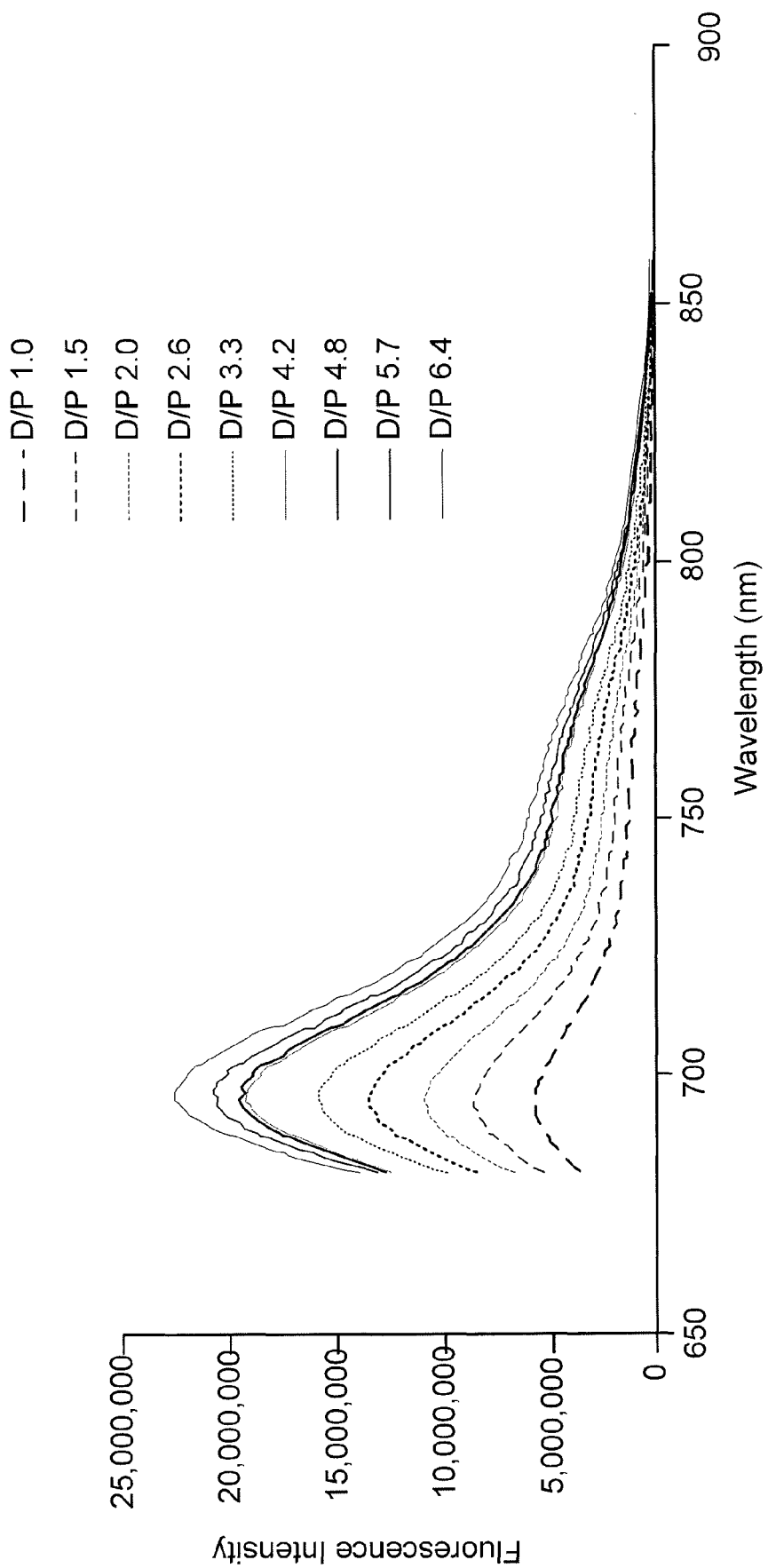
FIG. 6 shows fluorescence spectra for a series of goat anti-rabbit (GAR) antibody samples labeled at various D/P with compound 8.
Figure 7:
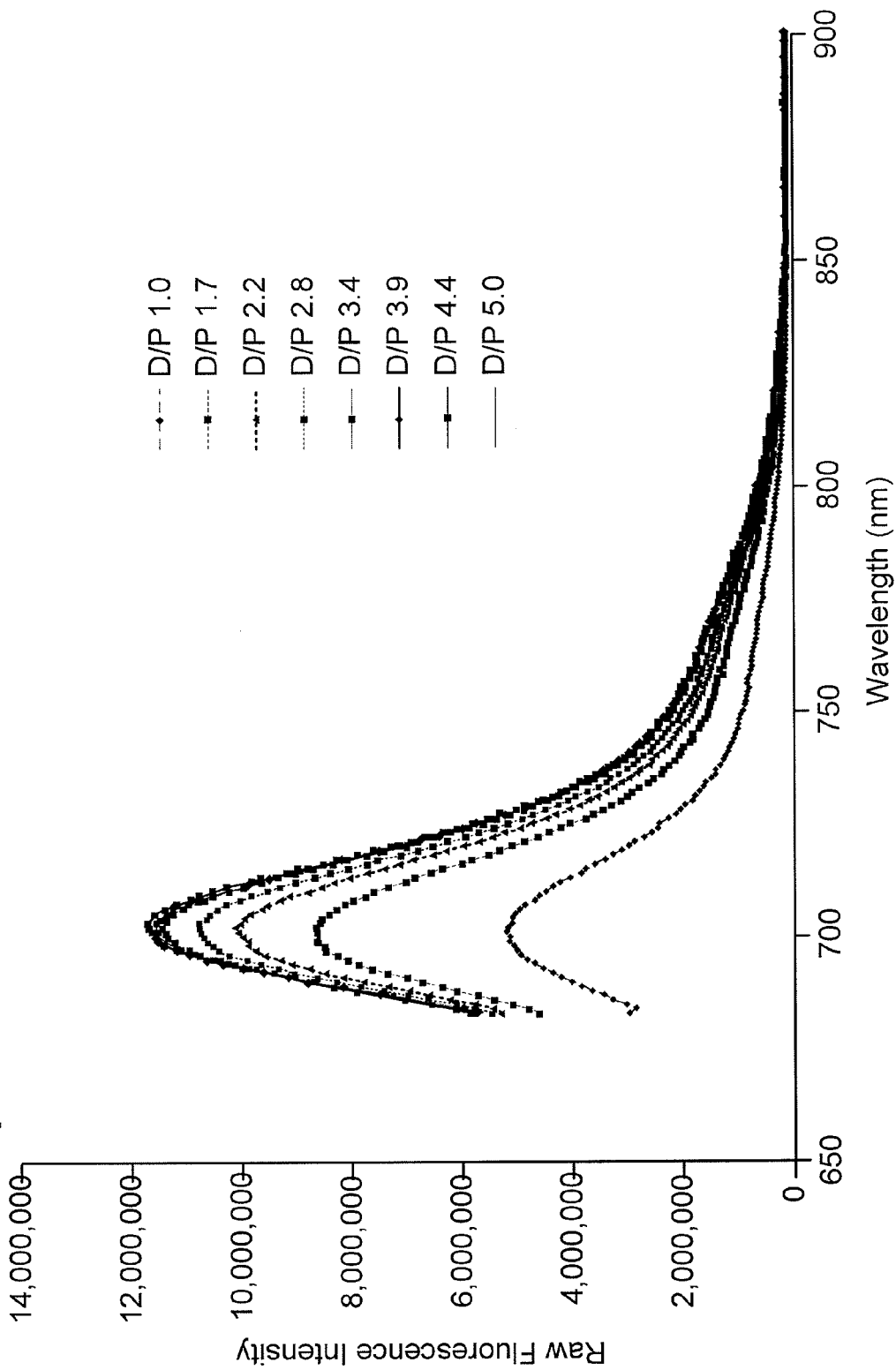
FIG. 7 shows fluorescence spectra for a series of goat anti-rabbit (GAR) antibody samples labeled at various D/P with Alexa Fluor 680.

Fluorescence determinations were made at a fixed antibody concentration of 10 mg/mL in physiological buffer using dye labeled goat anti-rabbit (GAR) conjugates prepared at LI-COR. Fluorescence was measured using a PTI Fluorometer at the optimum excitation wavelength of each dye (FIGS. 6 and 7). The fluorescence intensity of each conjugate increased with increased degree of labeling initially, until a maximum was reached. After that additional dyes did not increase the fluorescence of the conjugate.

Figure 8:
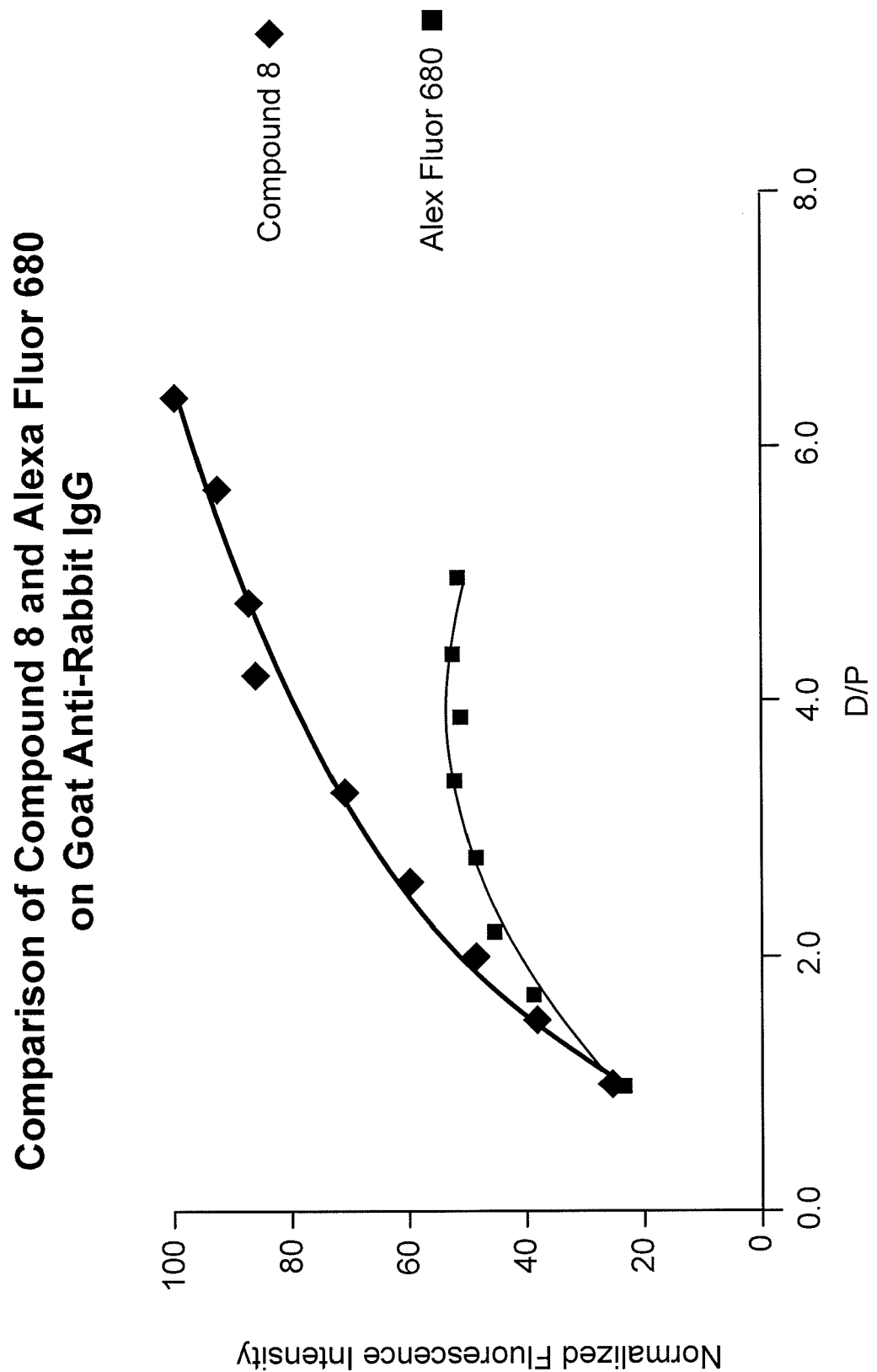
FIG. 8 shows the relative fluorescence as a function of D/P for the GAR antibody conjugates with compound 8 and Alexa Fluor 680.

The fluorescence intensity of each conjugate increased with increased degree of labeling initially, until a maximum was reached. After that, additional dyes did not increase the fluorescence of the conjugate. The plots of degree of labeling versus fluorescence for each dye (FIG. 8) show that in general, GAR conjugates with compound 8 were more intensely fluorescent than those with Alexa Fluor 680 at the same D/P values. Furthermore, additional compound 8 fluorophores added to the conjugate continued to increase the fluorescence over the entire range studied (D/P up to 6.4). In contrast the fluorescence of Alexa Fluor 680 conjugates quickly leveled off, and there was no benefit to increasing D/P beyond about 3. This leveling off of the fluorescence of conjugates with increasing D/P is a well-known phenomenon and is thought to be due to dye self-quenching. The compound 8 conjugates are more resistant to this self-quenching than Alexa Fluor 680 conjugates, since the former continue to increase in fluorescence intensity to at least D/P 6.4. Overall, the compound 8 conjugates are significantly brighter than the corresponding Alexa Fluor 680 conjugates.

Example 50

Comparison of Photostability: Compound 8, IRDye 700DX, and Alexa Fluor 680

Figure 9A:
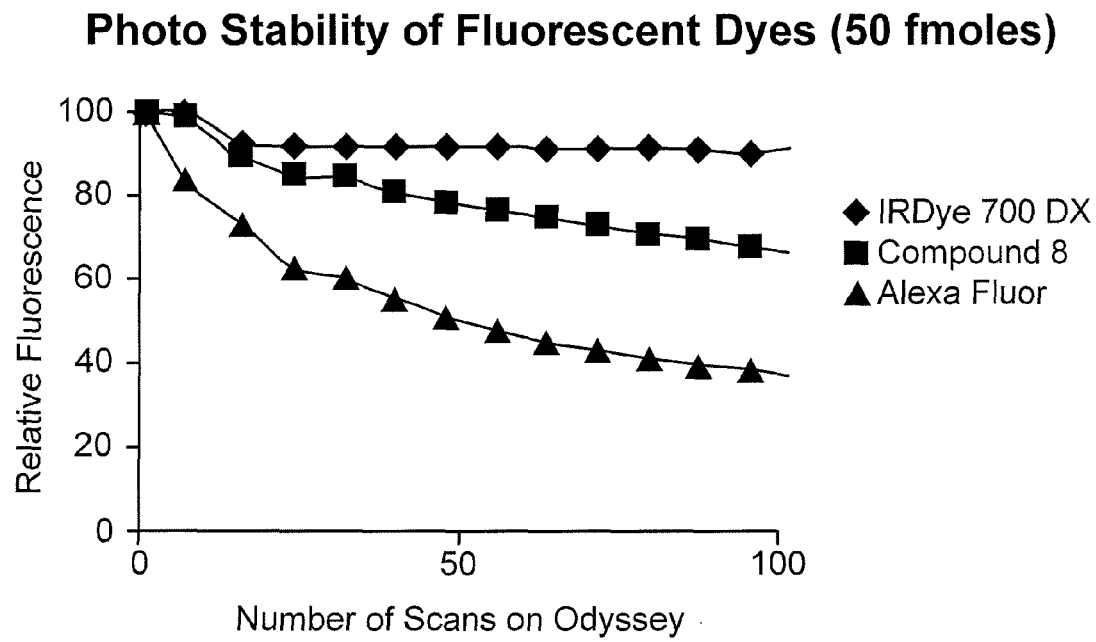
FIGS. 9A-B illustrate a comparison of photostability among IRDye 700DX, compound 8, and Alexa Fluor 680 at 50 fmoles (Panel A); and 25 fmoles (Panel B).
Figure 9B:
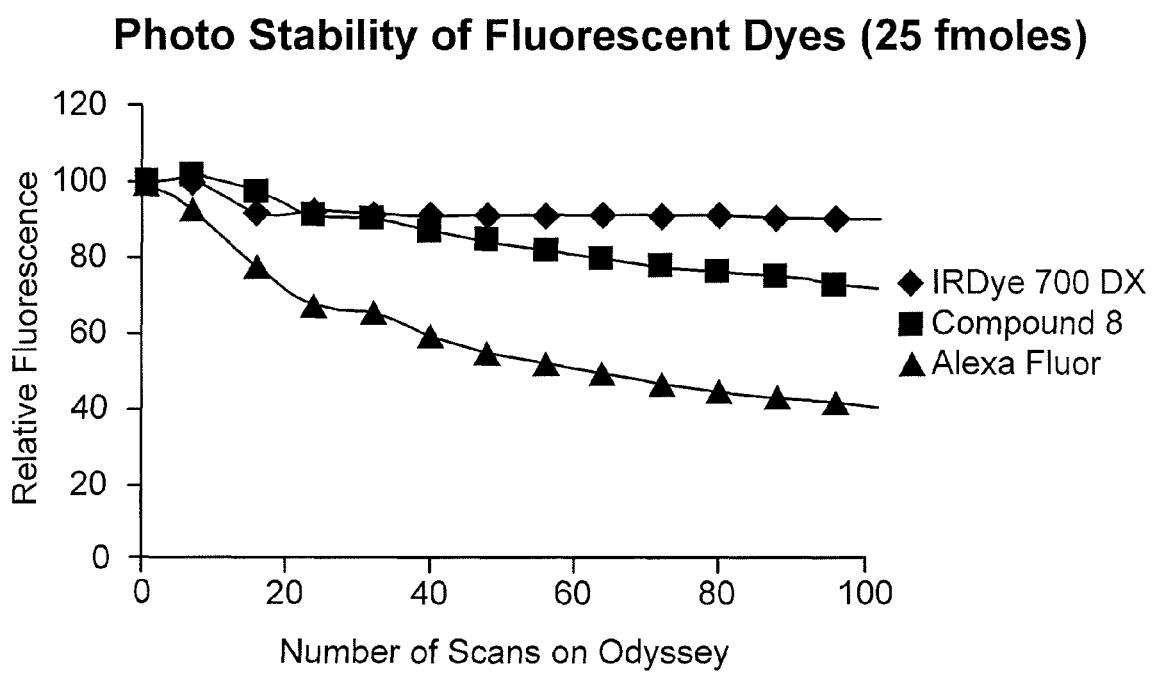

The photostability of compound 8 was compared to that of Alexa Fluor 680 and IRDye 700DX. IRDye 700DX is one of the most photostable 700 nm fluorescent dyes known. Test samples were prepared by spotting equimolar amounts of dye-labeled conjugates (i.e., goat anti-rabbit (GAR) secondary antibodies labeled with the appropriate dye) onto nitrocellulose membrane. The membrane was then scanned repeatedly on an Odyssey Infrared Imager, so that the prolonged exposure of the dyes to the laser source induced some photodegradation. The signal intensity for each dye was normalized to the signal in the first scan for that dye (FIG. 9A-B).

The relative fluorescence of the 700DX samples was essentially unchanged after 100 scans. While the fluorescence of the compound 8 samples decreased slightly with additional scans, this reduction was significantly less than that of the Alexa Fluor 680 samples. This demonstrates that compound 8 has good resistance to photodegradation.

Example 51

Comparison of GAR Cell Staining: Compound 8 and Alexa Fluor 680

Figure 10A:
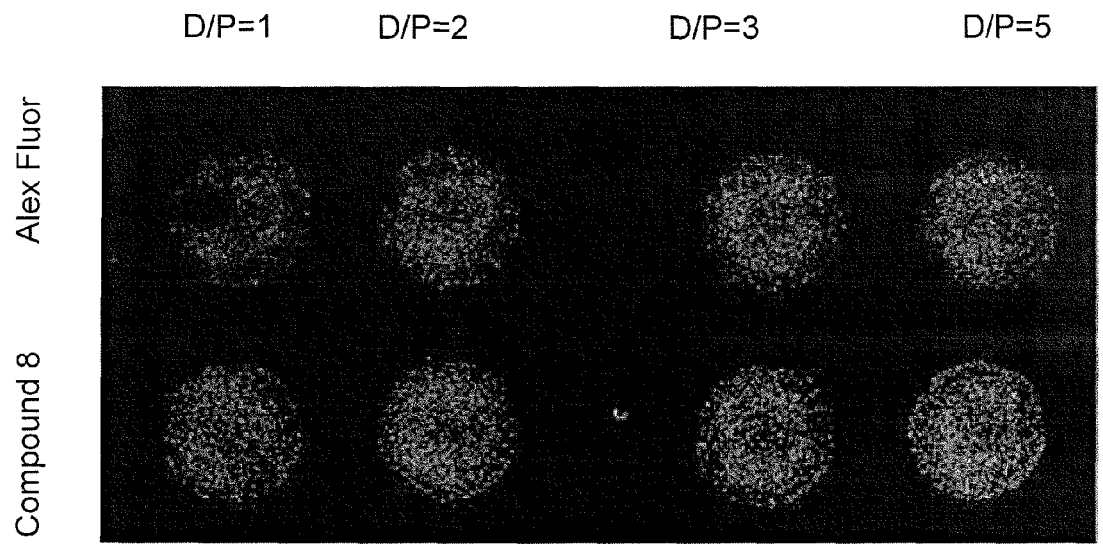
FIGS. 10A-B illustrate a comparison of cell staining and relative fluorescence between compound 8 and Alexa Fluor 680 (Panel A). Panel B compares fluorescence intensities.
Figure 10B:
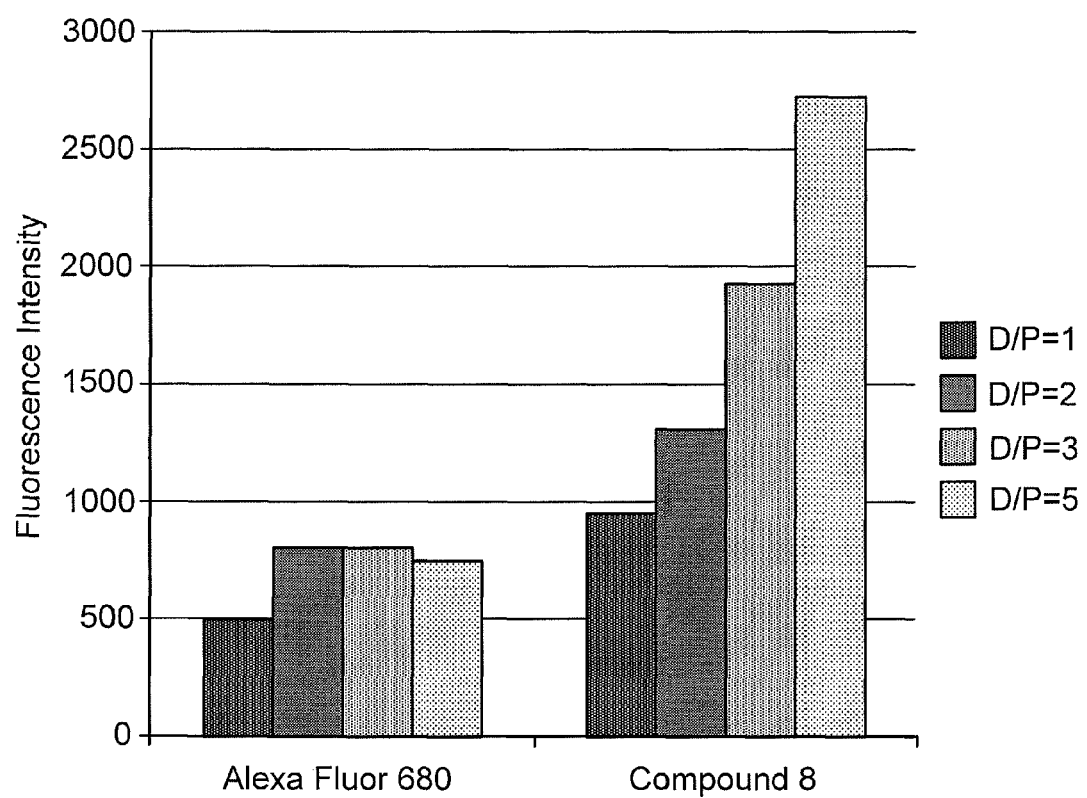

GAR secondary antibodies labeled with compound 8 or Alexa Fluor 680 for fluorescence measurements were used for cell staining (as previously described for the other GAR functional testing) (FIG. 10A-B).

Cultured SK-BR-3 (A) or SK-OV03 (B) were fixed with 3.7% formaldehyde and permeabilized with 0.1% Triton X-100. Cells were incubated with rabbit anti-HER2 mAb (CST), followed by goat and rabbit secondary antibodies labeled with compound 8 or Alexa Fluor 680. The plates were scanned on an Odyssey imager. The original images are shown on the left, and the quantified signal intensities are shown on the right (FIG. 10A-B).

The brightness and photostability of compound 8 conjugates make them an excellent choice for microscopy and In-Cell Westerns™. As well, overall fluorescence intensity or "brightness" at comparable D/P ratios was greater for compound 8 than for Alex Fluro 680. The signal intensity was two- to three-fold higher for cells stained with compound 8 labeled secondary antibody compared to the Alexa Fluor 680 conjugates. Later In-Cell Western data mimicked the fluorescence measurement data for the dye labeled conjugates.

Example 52

Comparison of Immunofluorescence Staining: Compound 8 and Alexa Fluor 680

HER2 protein was stained with dye-labeled antibodies on SK-BR-3 cell membrane. GAR secondary antibodies labeled with compound 8 were used for fluorescence measurements.

The cells were cultured on cover slips. After fixation and permabilization as per Example 50, the cells were incubated with rabbit anti-HER2 mAb (CST), followed by compound 8-labeled GAR secondary antibody (D/P=3.3). Sytox green was used to stain the nuclei. Images were acquired on an Olympus microscope and deconvolved using the accompanying software (FIG. 11A-C).

Example 53

Comparison of β-Actin Western Blots: Compound 8, IRDye 680, and Alexa Fluor 680

Compound 8 conjugates were compared by Western blot to commercially available IRDye 680 and Alexa Fluor 680 goat anti-mouse (GAM) antibody conjugates. All antibody conjugates were diluted to 0.1 µg/mL for the experiments.

Western blots were performed to detect actin in C32 lysates. Two-fold dilutions starting at 10 µg of C32 whole cell lysate (Santa Cruz) were loaded on a 10% Bis-Tris reducing gel and transferred to a nitrocellulose membrane (Odyssey). The mouse primary antibody against β-actin (Thermo Fisher Scientific) was used at 1:1000 dilution in a buffer of 0.2% Tween 20 in Odyssey Blocking Buffer. The various goat anti-mouse secondary antibodies were diluted in the same way. All antibody incubation was for 1 hour at ambient temperature. The results of the Western blot are shown in FIG. 12A-C. All Western blots were performed in duplicate.

An assessment of signal intensity, background and working dilution of the compound 8 antibodies was made in comparison to both IRDye 680 and Alexa Fluor 680 secondary antibodies. The signal intensity was linear as the concentration of cell lysate was increased up to about 5000 ng/lane (FIG. 13). The linear dynamic range for compound 8 was wider than for Alexa Fluor 680. Overall, the signal detected with compound 8 GAM is 3× greater than IRDye GAM and 1.5× higher than Alexa Fluor 680 GAM. The background on membranes treated with compound 8 GAM was comparable to that with the other 700 channel fluorophores. Visual inspection of the Western blots indicated a similar limit of detection between the three GAM-conjugated antibodies. Also, the compound 8 GAM, diluted to 0.04 µg/mL, maintains superior performance in terms of signal compared to IRDye 680 GAM at the same dilution.

Example 54

Comparison of p38 Western Blots: Compound 8, IRDye 680, and Alexa Fluor 680

A Western blot was performed to detect the lower expressing protein p38 in Jurkat lysates. Compound 8 conjugates were compared with commercially available IRDye 680 and Alexa Fluor 680 goat anti-rabbit (GAR) antibody conjugates. The dye-labeled antibodies were diluted as described in Example 53.

Two-fold dilutions starting at 10 μg of Jurkat cell lysate were loaded on a 10% Bis-Tris reducing gel and transferred to a nitrocellulose membrane (Odyssey). The rabbit primary antibody against p38 (Santa Cruz) was used at 1:1000 dilution in a buffer of 0.2% Tween 20 in Odyssey Blocking Buffer. The various goat anti-rabbit secondary antibodies were diluted in the same way. All antibody incubations were for 1 hour at ambient temperature. The results of the Western blot are shown in FIG. 14A-C. All Western blots were performed in duplicate.

The compound 8 GAR conjugates outperformed IRDye 680 GAR with a 2× to 4× improvement in signal intensity. With this target, the visual limit of detection was also improved by the same factor (conjugate concentrations of 0.1 μg/mL and 0.04 μ/mL, respectively). The signal of IRDye 680 GAR is up to 1.7× as bright as the Alexa Fluor 680 GAR at the same concentration, and the limit of detection was within a single two-fold dilution for the p38 target. Additional bands were seen on all Western blots, indicating that the primary antibody is detecting additional proteins.

Example 55

Akt Two-Color Western Blot: Compound 8, IRDye 800CW, and Alexa Fluor 680

Balanced two-color Western blots to detect the low abundant protein Akt were performed with compound 8 GAM and IRDye 800CW GAR antibodies. The dye-labeled antibodies were diluted as described in Example 53.

NIH 3T3 cell lysates (two-fold dilutions starting at 10 μg) were separated by SDS-PAGE and transferred to nitrocellulose. The membranes were blocked with LI-COR Blocking Buffer. The primary antibodies were against Akt (mouse mAb) and actin (rabit mAb), diluted 1:1000. The secondary antibody to detect actin was IRDye 800CW GAR (1:10,000). Akt was detected with (A) IRDye 680 GAM (0.1 μg/mL); (B) Alexa Fluor 680 GAM (0.1 μg/mL); (C) compound 8 GAM 0.1 μg/mL) on an Odyssey Infrared Imager.

Once again, compound 8 conjugates were brighter compared to IRDye 680 (FIG. 15A and FIG. 15C). Compound 8 GAM showed lower background than Alexa Fluor 680 GAM with an equivalent visual limit of detection (FIG. 15B-C).

Example 56

Akt Western Blot with Compound 8

Additional Western blot experiments (FIG. 16A-B) were performed using compound 8 GAM to detect Akt in A431 lysates. The dye-labeled antibodies were diluted as described in Example 53.

A431 lysates were separated on a 10% Bis-Tris gel, transferred to Odyssey nitrocellulose and blocked in Odyssey Blocking Buffer. For experiment A, the membrane was incubated for 1 hour with Akt mAb (Cell Signaling Technologies) diluted in Odyssey Blocking Buffer(1:1000), washed, and then incubated for 1 hour with compound 8 GAM (0.1 μg/mL). It was diluted in Odyssey Blocking Buffer including 0.2% Tween 20. For experiment FIG. 16B, the membrane was incubated only in secondary antibody as described in A. All membranes were washed as directed and imaged on the Odyssey Infrared Imager.

FIG. 16A illustrates the linearity of the conjugate over a large range of protein concentrations (50 μg-20 ng; $R^2$ is 0.9982 from 30 μg to 20 ng lysate).

Compound 8 secondary antibodies have been shown to have low non-specific binding to proteins in a variety of lystates (Jurkat, HeLa, C32, A431 & NIH3T3). An example of this low binding is shown in FIG. 16B, as the Western blot was performed without primary antibody. Even in the presence of 50 μg of protein there is little signal detected from the compound 8 GAM antibody.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references cited in this application, including patent applications, patents, and PCT publications, are incorporated herein by reference for all purposes.

What is claimed is:

1. A compound of Formula I:

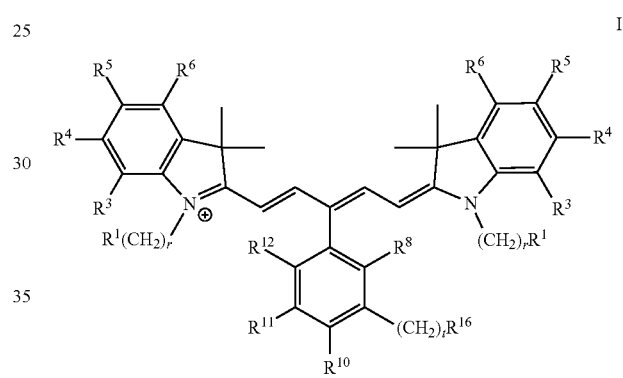

wherein
$R^1$ is sulfonato;
r is 2, 3, or 4;
$R^3$, $R^4$, $R^5$, and $R^6$ are each a member independently selected from the group consisting of hydrogen, alkyl, halo, alkoxy, sulfonato, alkoxyalkyl, and sulfonatoalkyl; or, alternatively, $R^5$ and $R^6$, together with a pair of atoms to which they are bonded, join to form an aryl ring, wherein each said aryl ring is additionally substituted with from 1 to 2 $R^{14}$;
$R^8$, $R^{10}$, $R^{11}$, and $R^{12}$ are each a member independently selected from the group consisting of hydrogen, alkyl, halo, alkoxy, and sulfonato;
each $R^{14}$ is a member independently selected from the group consisting of alkyl, halo, hydroxyl, alkoxy, amino, carboxyl, and sulfonato;
t is an integer from 1 to 10;
$R^{16}$ is carboxyl, maleimidyl, alkynyl, azido, or activated acyl;
wherein at least one substituent that is selected from the group consisting of $R^3$, $R^4$, $R^5$, $R^6$, and $R^{14}$ is sulfonato; and
wherein said compound has a balanced charge.

2. The compound of claim 1, wherein $R^3$, $R^4$, $R^5$, and $R^6$ are each a member independently selected from the group consisting of hydrogen, alkyl, halo, alkoxy, sulfonato, alkoxyalkyl, and sulfonatoalky.

3. The compound of claim 1, wherein $R^8$, $R^{10}$, $R^{11}$, and $R^{12}$ are each a member independently selected from the group consisting of hydrogen, alkyl, halo, and sulfonato.

4. The compound of claim 3, having the formula:

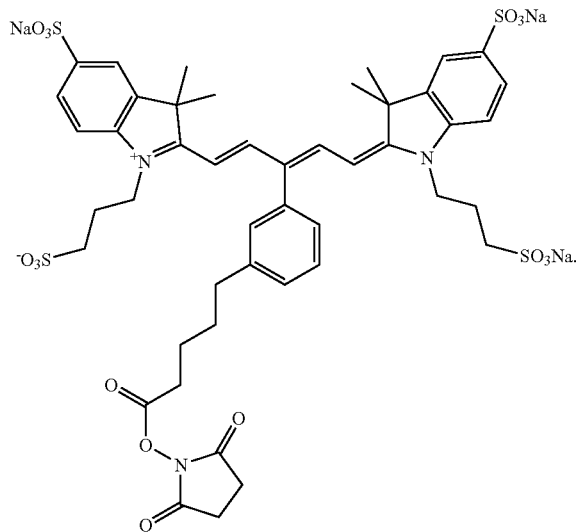

5. The compound of claim 1,
wherein t is 4; wherein $R^{16}$ is carboxyl; and wherein $R^3$, $R^4$, $R^5$, and $R^6$ are each a member independently selected from the group consisting of hydrogen and sulfonato.

6. The compound of claim 5, having the formula:

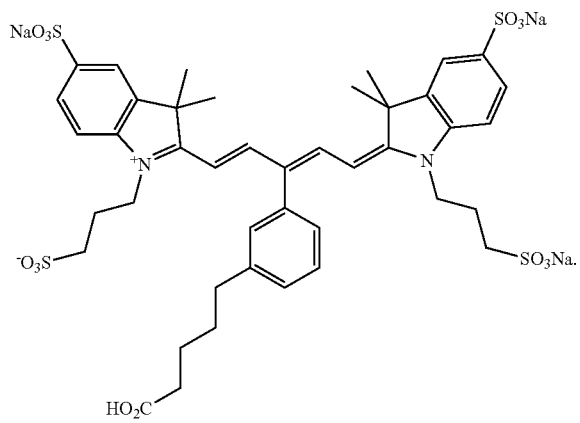

7. The compound of claim 1, wherein $R^{16}$ is maleimidyl.

8. The compound of claim 1, wherein $R^{16}$ is alkynyl or azido.

9. The compound of claim 1, having Formula Ia:

Ia

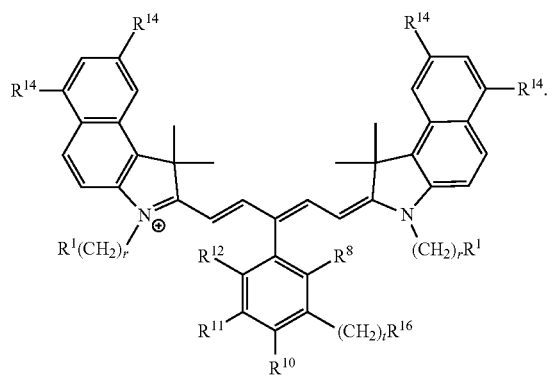

10. The compound of claim 9, wherein $R^{16}$ is maleimidyl.

11. The compound of claim 9, wherein $R^{16}$ is alkynyl or azido.

12. The compound of claim 9, wherein $R^8$, $R^{10}$, $R^{11}$, and $R^{12}$ are each a member independently selected from the group consisting of hydrogen, alkyl, halo, and sulfonato.

13. The compound of claim 12, having the formula:

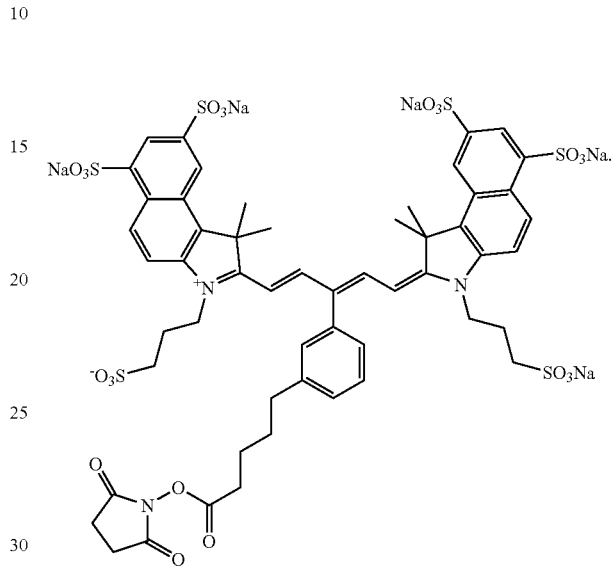

14. The compound of claim 12, having the formula:

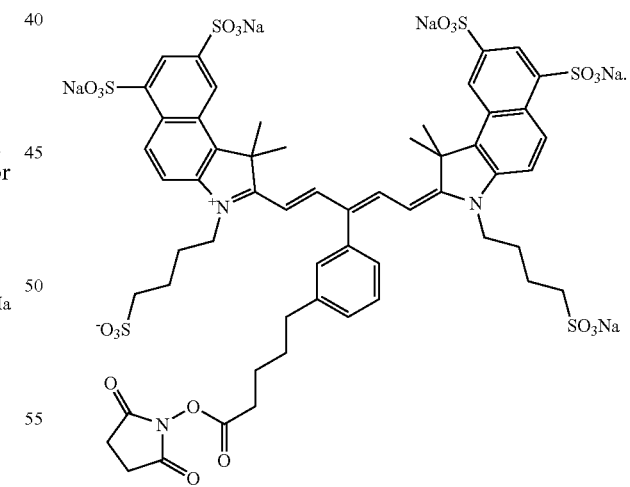

15. The compound of claim 12,
wherein t is 4; wherein $R^{16}$ is carboxyl; and wherein each $R^{14}$ is a member independently selected from the group consisting of hydrogen and sulfonato.

16. The compound of claim 15, having the formula:

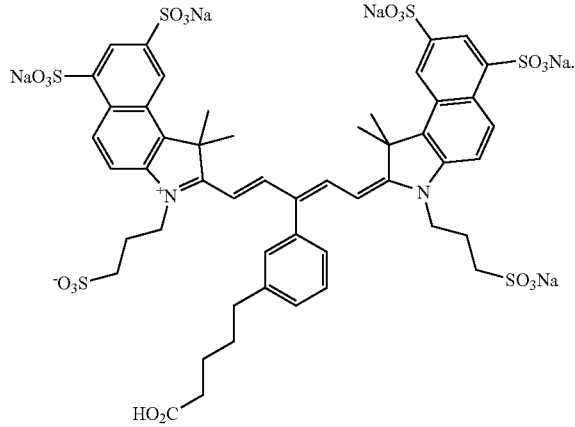

17. The compound of claim 15, having the formula:

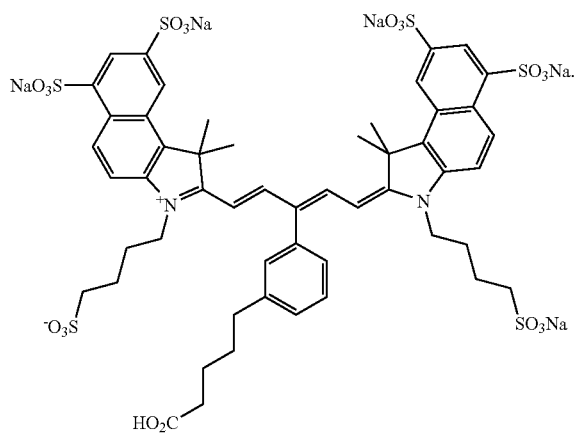

18. The compound of claim 1, wherein the compound fluoresces at a wavelength within the range of about 550 nm to about 1000 nm.

19. The compound of claim 1, wherein the compound fluoresces at a wavelength within the range of about 600 nm to about 850 nm.

20. The compound of claim 1, wherein the compound fluoresces at a wavelength within the range of about 600 nm to about 725 nm.

21. The compound of claim 1, wherein the compound fluoresces at a wavelength within the range of about 725 nm to about 850 nm.

22. A bioconjugate compound of Formula II:

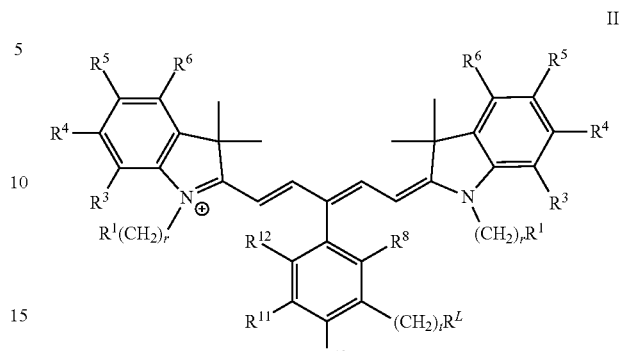

wherein
$R^1$ is sulfonato;
r is 2, 3, or 4;
$R^3$, $R^4$, $R^5$, and $R^6$ are each a member independently selected from the group consisting of hydrogen, alkyl, halo, alkoxy, sulfonato, alkoxyalkyl, and sulfonatoalkyl; or, alternatively, a pair of said members that is $R^5$ and $R^6$, together with a pair of atoms to which they are bonded, join to form an aryl ring, wherein each said aryl ring is additionally substituted with from 1 to 2 $R^{14}$;
$R^8$, $R^{10}$, $R^{11}$, and $R^{12}$ are each a member independently selected from the group consisting of hydrogen, alkyl, alkenyl, halo, alkoxy, and sulfonato;
each $R^{14}$ is a member independently selected from the group consisting of alkyl, halo, hydroxyl, alkoxy, amino, carboxyl, and sulfonato;
t is an integer from 1 to 10;
$R^L$ comprises a linking group and a biomolecule connected thereby;
wherein at least one substituent that is selected from the group consisting of $R^3$, $R^4$, $R^5$, $R^6$, and $R^{14}$ is sulfonato; and
wherein said compound has a balanced charge.

23. A method of labeling a biomolecule, said method comprising reacting a compound of claim 1 with a biomolecule.

24. A method of labeling a biomolecule, said method comprising:
reacting a compound of claim 1 with the biomolecule;
wherein said biomolecule is selected from the group consisting of somatostatin, endostatin, a carbohydrate, an oligosaccharide, an aptamer, a liposome, PEG, an angiopoietin, angiostatin, angiotensin II, α₂-antiplasmin, annexin V, β-cyclodextrin tetradecasulfate, endoglin, endosialin, endostatin, epidermal growth factor, fibrin, fibrinopeptide β, fibroblast growth factor, FGF-3, basic fibronectin, fumagillin, heparin, hepatocycte growth factor, hyaluronan, an insulin-like growth factor, an interferon-α, β inhibitor, IL inhibitor, laminin, leukemia inhibitory factor, linomide, a metalloproteinase, a metalloproteinase inhibitor, an antibody, an antibody fragment, an acyclic RGD peptide, a cyclic RGD peptide, placental growth factor, placental proliferin-related protein, plasminogen, plasminogen activator, plasminogen activator inhibitor-1, a platelet activating factor antagonist, platelet-derived growth factor, a platelet-derived growth factor receptor, a platelet-derived growth factor receptor, platelet-derived endothelial cell growth factor, pleiotropin, proliferin, proliferin-related protein, a selectin, SPARC, a snake venom, substance P, suramin, a tissue inhibitor of a metalloproteinase, thalidomide, thrombin, thrombin-receptor-activating tetradecapeptide, transformin growth factor-α, β, transforming growth factor receptor, tumor growth factor-α, tumor necrosis factor, vitronectin, and calcein.

25. A method of imaging, said method comprising: administering a compound of claim 1 to a tissue or an organism.

26. A method of imaging, said method comprising administering a compound of claim 22 to a tissue or an organism.

27. A compound of Formula I':

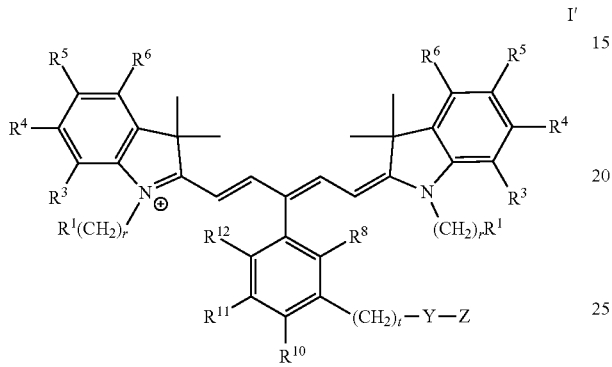

wherein $R^1$ is sulfonato;

r is 2, 3, or 4;

$R^3$, $R^4$, $R^5$, and $R^6$ are each a member independently selected from the group consisting of hydrogen, alkyl, halo, alkoxy, sulfonato, alkoxyalkyl, and sulfonatoalkyl; or, alternatively, $R^5$ and $R^6$, together with a pair of atoms to which they are bonded, join to form an aryl ring, wherein each said aryl ring is additionally substituted with from 1 to 2 $R^{14}$;

$R^8$, $R^{10}$, $R^{11}$, and $R^{12}$ are each a member independently selected from the group consisting of hydrogen, alkyl, halo, alkoxy, and sulfonato;

each $R^{14}$ is a member independently selected from the group consisting of alkyl, halo, hydroxyl, alkoxy, amino, carboxyl, and sulfonato;

t is an integer from 1 to 10;

Y is selected from the group consisting of —O—, —S—, —NH—, —NHC(O)—, —C(O)NH—, —$NR^{15}$—, —$NR^{15}$C(O)—, -and —C(O)$NR^{15}$—;

$R^{15}$ is selected from the group consisting of alkyl and alkoxycarbonylalkyl; wherein the alkyl is optionally interrupted by at least one heteroatom;

Z is a $C_1$-$C_{10}$ alkyl that is substituted with $R^{16}$; wherein the alkyl is optionally interrupted by at least one heteroatom;

$R^{16}$ is carboxyl, maleimidyl, alkynyl, azido, or activated acyl;

wherein at least one substituent that is selected from the group consisting of $R^3$, $R^4$, $R^5$, $R^6$, and $R^{14}$ is sulfonato; and wherein said compound has a balanced charge.

28. The compound of claim 27, wherein Y is selected from the group consisting of —NHC(O)—, —C(O)NH—, —$NR^{15}$C(O)—, -and —C(O)$NR^{15}$—;

$R^{15}$ is alkyl optionally interrupted by at least one heteroatom; and

Z is a $C_1$-$C_{10}$ alkyl that is substituted with $R^{16}$; wherein Z is optionally interrupted by at least one ether group.

29. The compound of claim 28, wherein Y is selected from the group consisting of —NHC(O)—, —C(O)NH—, —$NR^{15}$C(O)—, —and —C(O)$NR^{15}$—;

$R^{15}$ is alkyl; and

Z is a $C_1$-$C_{10}$ alkyl that is substituted with $R^{16}$.

* * * * *